US007556939B2

(12) United States Patent
Minoprio et al.

(10) Patent No.: US 7,556,939 B2
(45) Date of Patent: Jul. 7, 2009

(54) IDENTIFICATION AND CHARACTERIZATION OF RACEMASES, DEFINITION OF PROTEIN SIGNATURES, AND A TEST FOR DETECTING D-AMINO ACID AND FOR SCREENING MOLECULES CAPABLE OF INHIBITING THE ACTIVITY OF RACEMASE, ESPECIALLY PROLINE RACEMASE

(75) Inventors: Paola Minoprio, Villiers sur Marne (FR); Nathalie Chamond, Paris (FR); Wim Degrave, Paris cedex (FR); Armand Berneman, Paris (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 10/545,149

(22) PCT Filed: Feb. 11, 2004

(86) PCT No.: PCT/IB2004/000861

§ 371 (c)(1),
(2), (4) Date: Aug. 15, 2006

(87) PCT Pub. No.: WO2004/072223

PCT Pub. Date: Aug. 26, 2004

(65) Prior Publication Data

US 2007/0128601 A1    Jun. 7, 2007

Related U.S. Application Data

(60) Provisional application No. 60/446,263, filed on Feb. 11, 2003.

(51) Int. Cl.
*C12P 21/06* (2006.01)
*C12Q 1/68* (2006.01)
*C12N 15/00* (2006.01)

(52) U.S. Cl. .................. 435/69.1; 435/6; 435/320.1; 536/23.1

(58) Field of Classification Search .............. None
See application file for complete search history.

(56) References Cited

U.S. PATENT DOCUMENTS

| 6,459,996 | B1 | 10/2002 | Somers et al. |
| 6,524,589 | B1 | 2/2003 | Reichert et al. |
| 6,546,074 | B1 | 4/2003 | Blundell et al. |
| 2005/0250195 | A1 | 11/2005 | Minoprio et al. |
| 2006/0014162 | A1 | 1/2006 | Minoprio et al. |

FOREIGN PATENT DOCUMENTS

| JP | 55-081595 | 6/1980 |
| WO | WO-01/40449 A2 | 6/2001 |
| WO | WO 01/40449 A2 | 6/2001 |
| WO | WO-01/40449 A3 | 6/2001 |
| WO | WO-2004/106506 A2 | 12/2004 |

OTHER PUBLICATIONS

Delvecchio, V. G. et al., "The Genome Sequence of the Facultative Intracellular Pathogen *Brucella melitensis*," Abstract of Proc. Natl. Acad. Sci. U.S.A., vol. 99, No. 1, pp. 443-448, XP002290326, (2002).
Matsushita Elec. Ind. Co. Ltd., "Quantitative Qualitative Determination of Aminoacid by Converting One Optical Active Isomer to Another Using Amino acid Racemase and Oxidation," Patent Abstract of JP. No. 55-081595, (Jun. 19, 1980).
Reina-San-Martin, B. et al., "A B-Cell Mitogen From a Pathogenic Trypanosome is a Eukaryotic Proline Racemase," Nature Medicine, vol. 6, No. 8, pp. 890-897, (Aug. 2000).
Delvecchio, V. G. et al., "The Genome Sequence of the Facultative Intracellular Pathogen *Brucella melitensis*," Proc. Natl. Acad. Sci. U.S.A., vol. 99, No. 1, pp. 443-448, (Jan. 8, 2002).
Chamond, N. et al., "Biochemical Characterization of Proline Racemases from the Human Protozoan Parasite *Trypanosoma Cruzi* and Definition of Putative Protein Signatures," The Journal of Biological Chemistry, vol. 278, No. 18, pp. 15484-15494, (May 2, 2003).
Rudnick, G. et al., "Reaction Mechanism and Structure of the Active Site of Proline Racemase," Biochemistry, vol. 14, No. 20, pp. 4515-4522, (1975).
Cardinale, G. J. et al., "Purification and Mechanism of Action of Proline Racemase," Biochemistry, vol. 7, No. 11, pp. 3970-3978, (1968).
Chamond et al.; "Immunotherapy of *Trypanosoma Cruzi* Infections"; Current Drug Targets—Immune, Endocrine & Metabollic Disorders, vol. 2, No. 3, pp. 247-254, (2002).
Minoprio, P. et al., U.S. Appl. No. 10/558,371, filed Nov. 29, 2005, as a national stage application of PCT/IB04/002062, filed Feb. 11, 2004, and published as WO 2004/106506 A2.
Delvecchio, V. G. et al., "The Genome Sequence of the Facultative Intracellular Pathogen *Brucella melitensis*," Abstract of Proc. Natl. Acad. Sci. U.S.A., vol. 99, No. 1, pp. 443-448, XP002290326, (2002).
Office Action mailed Dec. 10, 2004, in U.S. Appl. No. 11/008,570, filed Dec. 10, 2004 (published as US-2006-0014162-A1).

*Primary Examiner*—Nashaat T Nashed
*Assistant Examiner*—Younus Meah
(74) *Attorney, Agent, or Firm*—Finnegan, Henderson, Farabow, Garrett & Dunner L.L.P.

(57) ABSTRACT

This invention relates to the identification and characterization of racemases and definition of protein signatures of these racemases. More particularly, this invention relates to the identification of nucleic acid molecules encoding a peptide consisting of a motif characteristic of the protein signatures, and to the peptides consisting of these motifs and more specifically SEQ ID NOS: 1-4. This invention also relates to antibodies specific for the peptides and to immune complexes of these antibodies with the peptides. Further, the invention relates to methods and kits for detecting racemases using the nucleic acid molecules of the invention, as well as the peptides consisting of the motifs and antibodies to these peptides.

8 Claims, 20 Drawing Sheets

IDENTIFICATION AND CHARACTERIZATION OF RACEMASES, DEFINITION OF PROTEIN SIGNATURES, AND A TEST FOR DETECTING D-AMINO ACID AND FOR SCREENING MOLECULES CAPABLE OF INHIBITING THE ACTIVITY OF RACEMASE, ESPECIALLY PROLINE RACEMASE

CROSS-REFERENCE TO RELATED APPLICATION

This application is based on and claims the benefit of U.S. Provisional Application Ser. No. 60/446,263, filed Feb. 11, 2003. The entire disclosure of this Provisional application is relied upon and incorporated by reference herein

BACKGROUND OF THE INVENTION

This invention relates to the identification and characterization of racemases and definition of protein signatures of these racemases. More particularly, this invention relates to the identification of nucleic acid molecules encoding a peptide consisting of a motif characteristic of the protein signatures, and to the peptides consisting of these motifs. This invention also relates to antibodies specific for the peptides and to immune complexes of these antibodies with the peptides. Further, the invention relates to methods and kits for detecting racemases using the nucleic acid molecules of the invention, as well as the peptides consisting of the motifs and antibodies to these peptides.

D-amino acids have long been described in the cell wall of gram-positive and especially gram-negative bacteria, where they constitute essential elements of the peptidoglycan and as substitutes of cell wall techoic acids (1). Moreover, various types of D-amino acids were discovered in a number of small peptides made by a variety of microorganisms through non-ribosomal protein synthesis (2), that function mainly as antibiotic agents. However, these examples were considered exceptions to the rule of homochirality and a dogma persisted that only L-amino acid enantiomers were present in eukaryotes, apart from a very low level of D-amino acids from spontaneous racemization due to aging (3).

Recently, an increasing number of studies have reported the presence of various D-amino acids (D-aa) either as protein bound (4) or under free forms (5) in a wide variety of organisms, including mammals. The origin of free D-aa, is less clear than that of protein bound D-aa. For instance, in mammals, free D-aa may originate from exogenous sources (as described in (6), but the recent discovery of amino acid racemases in eukaryotes has also uncovered an endogenous production of D-aa, questioning their specific functions. Thus, the level of D-aspartate is developmentally regulated in rat embryos (7); the binding of D-serine to NMDA mouse brain receptors promotes neuromodulation (8),(9), and D-aspartate appears to be involved in hormonal regulation in endocrine tissues (10).

All amino acid racemases require pyridoxal phosphate as a cofactor, except proline and hydroxyproline racemases, which are cofactor-independent enzymes. For example, two reports have been published addressing the biochemical and enzymatic characteristics of the proline racemase from the gram-positive bacterium Clostridium sticklandii (11,12). A reaction mechanism was proposed whereby the active site $Cys^{256}$ forms a half-reaction site with the corresponding cysteine of the other monomer in the active, homodimeric enzyme.

Although a variety of racemases and epimerases has been demonstrated in bacteria and fungi, the first eukaryotic amino acid (proline) racemase isolated from the infective metacyclic forms of the parasitic protozoan Trypanosoma cruzi, the causative agent of Chagas' disease in humans (13), was recently described. This parasite-secreted proline racemase (TcPRAC) was shown to be a potent mitogen for host B cells and to play an important role in T. cruzi immune evasion and persistence through polyclonal lymphocyte activation (13). This protein, previously annotated as TcPA45, with monomer size of 45 kDa, is only expressed and released by infective metacyclic forms of the parasite (13).

The genomic organization and transcription of TcPRAC proline racemase gene indicated the presence of two homologous genes per haploid genome (TcPRACA and TcPRACB). Furthermore, localization studies using specific antibodies directed to 45 kDa-TcPRAC protein revealed that an intracellular and/or membrane associated isoform, with monomer size of 39 kDa is expressed in non-infective epimastigote forms of the parasite.

Computer-assisted analysis of the TcPRACA gene sequence suggested that it could give rise to both isoforms (45 kDa and 39 kDa) of parasite proline racemases through a mechanism of alternative trans-splicing, one of which would contain a signal peptide (13). In addition, preliminary analysis of putative TcPRACB gene sequences had revealed several differences that include point mutations as compared to TcPRACA, but that also suggest that TcPRACB gene could only encode an intracellular isoform of the enzyme as the gene lacks the export signal sequence. Any of these molecular mechanisms per se would ensure the differential expression of intracellular and extracellular isoforms of proline racemases produced in different T. cruzi developmental stages.

The process of production of a D-amino acid by using a L-amino acid source comprises the use of an amino acid racemase specific for the amino acid of interest, the racemase being produced from a recombinant expression system containing a vector having a polynucleotide sequence encoding the enzyme. In prokaryotic hosts, the racemases are known to be implicated in the synthesis of D-amino acids and/or in the metabolism of L-amino acids. For instance, the presence of free D-amino acids in tumors and in progressive autoimmune and degenerative diseases suggests the biological importance of eukaryotic amino acid racemases. It is well known that proteins or peptides containing D-amino acids are resistant to proteolysis by host enzymes. In addition, such proteins containing D-amino acids, at least one D-amino acid residue, can display antibiotic or immunogenic properties.

There is a growing interest in the biological role of D-amino acids, either as free molecules or within polypeptide chains in human brain, tumors, anti-microbial and neuropeptides, suggesting widespread biological implications. Research on D-amino acids in living organisms has been hampered by their difficult detection. There exists a need in the art for the identification of racemases and the identification of their enzymatic properties and their specificity for other compounds.

Although much progress has been made concerning prophylaxis of Chagas' disease, particularly vector eradication, additional cases of infection and disease development still occur every day throughout the world. Whilst infection was largely limited in the past to vector transmission in endemic areas of Latin America, its impact has increased in terms of congenital and blood transmission, transplants and recrudescence following immunosuppressive states. Prevalence of Chagas' disease in Latin America may reach 25% of the population, as is the case of Bolivia, or yet 1%, as observed in Mexico. From the 18-20 million people already infected with the parasite *Trypanosoma cruzi*, more than 60% live in Brazil and WHO estimates that 90 million individuals are at risk in South and Central America.

Some figures obtained from a recent census in USA, for instance, revealed that the net immigration from Mexico is about 1000 people/day, of those 5-10 individuals are infected by Chagas' disease. The disease can lie dormant for 10-30 years and as an example of many other progressive chronic pathologies it is characterized by being "asymptomatic". Although at the 1990's, blood banks increased their appeals to Hispanics (50% of Bolivian blood is contaminated), panels of Food and Drug Administration (FDA) have recommended that all donated blood be screened for Chagas. Today, FDA has not yet approved an 'accurate' blood test to screen donor blood samples. This allegation seriously contrasts with the more than 30 available tests used in endemic countries. Additionally, recent reports on new insect vectors adapted to the parasite and domestic animals infected in more developed countries like USA, and the distributional predictions based on Genetic Algorithm for Rule-set Prediction models indicate a potentially broad distribution for these species and suggest additional areas of risk beyond those previously reported emphasizing the continuing worldwide public health issue.

To date, two drugs are particularly used to treat *Trypanosoma cruzi* infections. Nifurtimox (3-methyl-4-5'-nitrofurfurylidene-amino tetrahydro 4H-1,4-thiazine-1,1-dioxide), a nitrofurane from Bayer, known as Lampit, was the first drug to be used since 1967. After 1973, Benznidazol, a nitroimidazole derivative, known as Rochagan or Radanyl (N-benzyl-2-nitro-1-imidazol acetamide) was produced by Hoffman-La-Roche and is consensually the drug of choice. Both drugs are trypanosomicides and act against intracellular or extracellular forms of the parasite. Adverse side-effects include a localized or generalized allergic dermopathy, peripheral sensitive polyneuropathy, leukopenia, anorexia, digestive manifestations and rare cases of convulsions which are reversible by interruption of treatment. The most serious complications include agranulocytosis and thrombocytopenic purpura.

Unquestionably, the treatment is efficient and should be applied in acute phases of infection, in children, and in cases where reactivation of parasitaemia is observed following therapy with immunosuppressive drugs or organ transplantation procedures. Some experts recommend that patients in indeterminate and chronic phases should also be treated. However, close to a hundred years after the discovery of the infection and its consequent disease, researchers still maintain divergent points of view concerning therapy against the chronic phases of the disease. As one of the criteria of cure is based on the absence of the parasite in the blood, it is very difficult to evaluate the efficacy of the treatment in indeterminate or chronic phases. Because the indeterminate form is asymptomatic, it is impossible to clinically evaluate the cure. Furthermore, a combination of serology and more sensitive advanced molecular techniques will be required and still may not be conclusive. The follow-up of patients for many years is then inevitable to objectively ascertain the cure.

Chagas' disease was recently considered as a neglected disease and DND-initiative (Drug for Neglected Diseases Initiative, DNDi) wishes to support drug discovery projects focused on the development of effective, safe and affordable new drugs against trypanosomiosis. Since current therapies remain a matter of debate, may be inadequate in some circumstances, are rather toxic and may be of limited effectiveness, the characterization of new formulations and the discovery of parasite molecules capable of eliciting protective immunity are absolutely required and must be considered as priorities.

SUMMARY OF THE INVENTION

This invention aids in fulfilling these needs in the art. It has been discovered that the TcPRAC genes in *T. cruzi* encode functional intracellular or secreted versions of the enzyme exhibiting distinct kinetic properties that may be relevant for their relative catalytic efficiency. While the $K_M$ of the enzyme isoforms were of a similar order of magnitude (29-75 mM), $V_{max}$ varied between $2 \times 10^{-4}$ to $5.3 \times 10^{-5}$ mol of L-proline/sec/0.125 µM of homodimeric recombinant protein. Studies with the enzyme specific inhibitor and abrogation of enzymatic activity by site-directed mutagenesis of the active site $Cys^{330}$ residue, reinforced the potential of proline racemase as a critical target for drug development against Chagas' disease.

This invention provides a purified nucleic acid molecule encoding a peptide consisting of a motif selected from SEQ ID NOS: 1, 2, 3, or 4.

This invention also provides a purified nucleic acid molecule that hybridizes to either strand of a denatured, double-stranded DNA comprising this nucleic acid molecule under conditions of moderate stringency.

In addition, this invention provides a recombinant vector that directs the expression of a nucleic acid molecule selected from these purified nucleic acid molecules.

Further, this invention provides a purified polypeptide encoded by a nucleic acid molecule selected from the group consisting of a purified nucleic acid molecule coding for:

(a) a purified polypeptide consisting of Motif I (SEQ ID NO:1);

(b) a purified polypeptide consisting of Motif II (SEQ ID NO:2);

(c) a purified polypeptide consisting of Motif III (SEQ ID NO:3); and (d) a purified polypeptide consisting of Motif III* (SEQ ID NO:4).

Purified antibodies that bind to these polypeptides are provided. The purified antibodies can be monoclonal antibodies. An immunological complex comprises a polypeptide and an antibody that specifically recognizes the polypeptide of the invention.

A host cell transfected or transduced with the recombinant vector of the invention is provided.

A method for the production of a polypeptide consisting of SEQ ID NOS: 1, 2, 3, or 4, comprises culturing a host cell of the invention under conditions promoting expression, and recovering the polypeptide from the host cell or the culture medium. The host cell can be a bacterial cell, parasite cell, or eukaryotic cell.

A method of the invention for detecting a racemase encoded by a nucleotide sequence containing a subsequence encoding a peptide selected from SEQ ID NO: 1, 2, 3, or 4, comprises:

(a) contacting the nucleotide sequence with a primer or a probe, which hybridizes with the nucleic acid molecule of the invention;

(b) amplifying the nucleotide sequence using the primer or the probe; and (c) detecting a hybridized complex formed between the primer or probe and the nucleotide sequence.

This invention provides a method of detecting a racemase encoded by a nucleotide sequence containing a subsequence encoding a peptide selected from SEQ ID NO: 1, 2, 3, or 4. The method comprises:

(a) contacting the racemase with antibodies of the invention; and
(b) detecting the resulting immunocomplex.

A kit for detecting a racemase encoded by a nucleotide sequence containing a subsequence encoding a peptide selected from SEQ ID NO: 1, 2, 3, or 4, comprises:

(a) a polynucleotide probe or primer, which hybridizes with the polynucleotide of the invention; and
(b) reagents to perform a nucleic acid hybridization reaction.

This invention also provides a kit for detecting a racemase encoded by a nucleotide sequence containing a subsequence encoding a peptide selected from SEQ ID NO: 1, 2, 3, or 4. The kit comprises:

(a) purified antibodies of the invention;
(b) standard reagents in a purified form; and
(c) detection reagents.

An in vitro method of screening for an active molecule capable of inhibiting a racemase encoded by a nucleotide sequence containing a subsequence encoding a peptide selected from SEQ ID NO: 1, 2, 3, or 4, comprises:

(a) contacting the active molecule with the racemase;
(b) testing the capacity of the active molecule, at various concentrations, to inhibit the activity of the racemase; and
(c) choosing the active molecule that provides an inhibitory effect of at least 80% on the activity of any proline racemase.

In a preferred embodiment of the invention the racemase is a proline racemase.

An immunizing composition of the invention contains at least a purified polypeptide of the invention, capable of inducing an immune response in vivo, and a pharmaceutical carrier.

This invention also provides a method for detecting a D-amino acid. The method comprises:

(A) providing a reaction medium containing the D-amino acid;
(B) reacting the D-amino acid with a D-amino oxidase with a prosthetic group to form a reduced prosthetic group by oxidative deamination of the D-amino acid with a primary amine or oxidation of the D-amino acid with a secondary amine;
(C) reacting the reduced prosthetic group with oxygen to form hydrogen peroxide; and
(D) detecting the hydrogen peroxide thus formed.

In embodiments of the method, the prosthetic group can be flavin-adenin-dinucleotide (FAD) or flavin-mononucleotide (FMN). In embodiments of the method, the hydrogen peroxide can be detected by reaction with a catalase. In other embodiments of the method, the hydrogen peroxide is detected by reaction with a peroxidase. In embodiments of the method, the D-amino acid is a D-Proline, D-Tyrosine, D-Valine, D-Threonine, D-Glutamic acid, D-Lysine, or D-Tryptophane. The method can further comprise quantifying the D-amino acid in the reaction medium after the formation of the hydrogen peroxide. In embodiments of the method, the reaction medium can comprise a biological sample from a subject afflicted with Alzheimer's disease, Parkinson's disease, renal disease, or schizophrenia. In embodiments of the method, the biological sample can comprise a fluid or tissue sample from the subject. In embodiments of the method the biological sample can comprise cells from the subject.

The invention also provides a method for detecting racemase activity in a reaction medium. The method comprises:

(A) providing a reaction medium containing a D-amino acid specific to the racemase to be detected;
(B) reacting the D-amino acid with a D-amino oxidase with a prosthetic group to form a reduced prosthetic group by oxidation of the D-amino acid;
(C) reacting the reduced prosthetic group with oxygen to form hydrogen peroxide; and
(D) detecting the hydrogen peroxide thus formed.

wherein the detection of hydrogen peroxide indicates racemase activity in the reaction medium.

In embodiments of the method the hydrogen peroxide can be detected by reaction with catalase. In other embodiments of the method, the hydrogen peroxide can be detected with a chromogenic reagent. The chromogenic reagent can be ortho-phenylalaninediamine (OPO), 3,3',5,5'-tetramethylbenzadine (TMB), or 5-aminosalicyclic acid (ASA).

The invention also provides a kit for screening for inhibitors of TcPRAC. The kit comprises:

(A) L-proline, D-proline, and a proline-racemase;
(B) a peroxidase and a substrate of a peroxidase, or a catalase and a reagent sensitive to oxygen;
(C) a D-amino acid oxidase; and
(D) optionally, one or more molecules to be screened for inhibitory activity of TcPRAC.

The invention also provides a kit for detecting a D-amino acid in a sample. The kit comprises:

(A) a D-amino acid;
(B) a peroxidase and a substrate of a peroxidase;
(C) a D-amino acid oxidase; and
(D) optionally, a L-amino acid enantiomer as control.

The invention also provides a method for detecting a D-amino acid in a sample.

The Method Comprises:

(A) oxidatively deaminating a D-amino acid by reaction with a D-amino acid oxidase in a prosthetic group; and
(B) detecting the hydrogen peroxide generated by the oxidative deamination;

wherein the presence of hydrogen peroxide is indicative of the presence of a D-amino acid in the sample.

In embodiments of the method, the D-amino acid can be D-Proline, D-Tyrosine, D-Valine, D-Threonine, D-Glutamic acid, D-Lysine, or D-Tryptophane.

The invention also provides a method for screening a molecule, which can modulate a racemase activity. The method comprises:

(A) modulating a racemase activity by means of a molecule being tested in the presence of an equimolar mixture of a L- and D-amino acid and of a racemase to be modulated;
(B) oxidatively deaminating the D-amino acid generated in step (A) by means of a D-amino oxidase in a prosthetic group; and
(C) detecting the hydrogen peroxide generated by the oxidative deamination;

wherein modulation of the hydrogen peroxide is indicative of the capability of the tested molecule to modulate racemase activity.

In embodiments of the method, the molecule inhibits the racemase activity. In embodiments of the method, the racemase is a proline racemase. In embodiments of the method, the proline racemase is *Tripanosoma cruzi* proline racemase.

The invention also provides a molecule identified by one of these methods.

The invention also provides a technological platform and all reagents and devices necessary to perform a method of the invention. The technology platform can comprise:

a) L-amino acid, D-amino acid, and a racemase;
b) a peroxidase and a substrate of a peroxidase, or a catalase and a reagent sensitive to oxygen;
c) a D-amino acid oxidase; and
d) optionally, one or more molecules to be screened for inhibitory activity of said racemase.

In embodiments of the technological platform, the racemase is a proline racemase and the L-amino acid and D-amino acid are L-proline and D-proline, respectively.

The invention also provides a molecule that inhibits a proline racemase containing a subsequence selected from the SEQ ID NO: 1, 2, 3 or 4.

BRIEF DESCRIPTION OF THE DRAWINGS

This invention will be understood with reference to the drawings in which:

Figure 6:
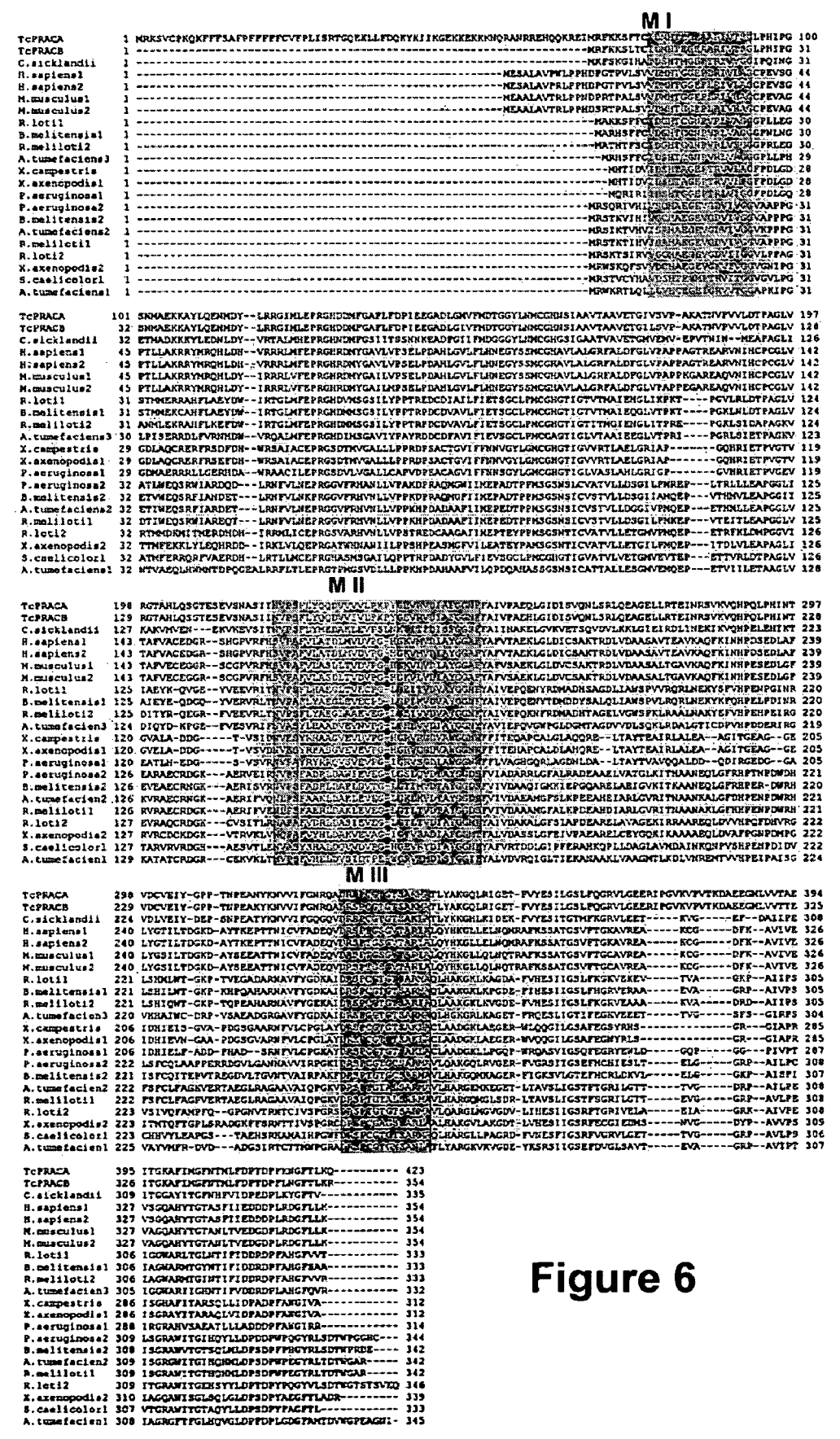

FIG. 6: Sequence alignments of proteins (Clustal X) obtained by screening SWISS-PROT and TrEMBL databases using motifs I, II and III (SEQ ID NOS 30, 52, and 32-51, respectively in order of appearance). Amino acids involved in MI, MII and MIII are shaded in dark grey and light grey figures the 13-14 unspecific amino acids involved in M II. SWISS-PROT accession numbers of the sequences are in Table IV.

DETAILED DESCRIPTION OF THE INVENTION

Figure 1C:
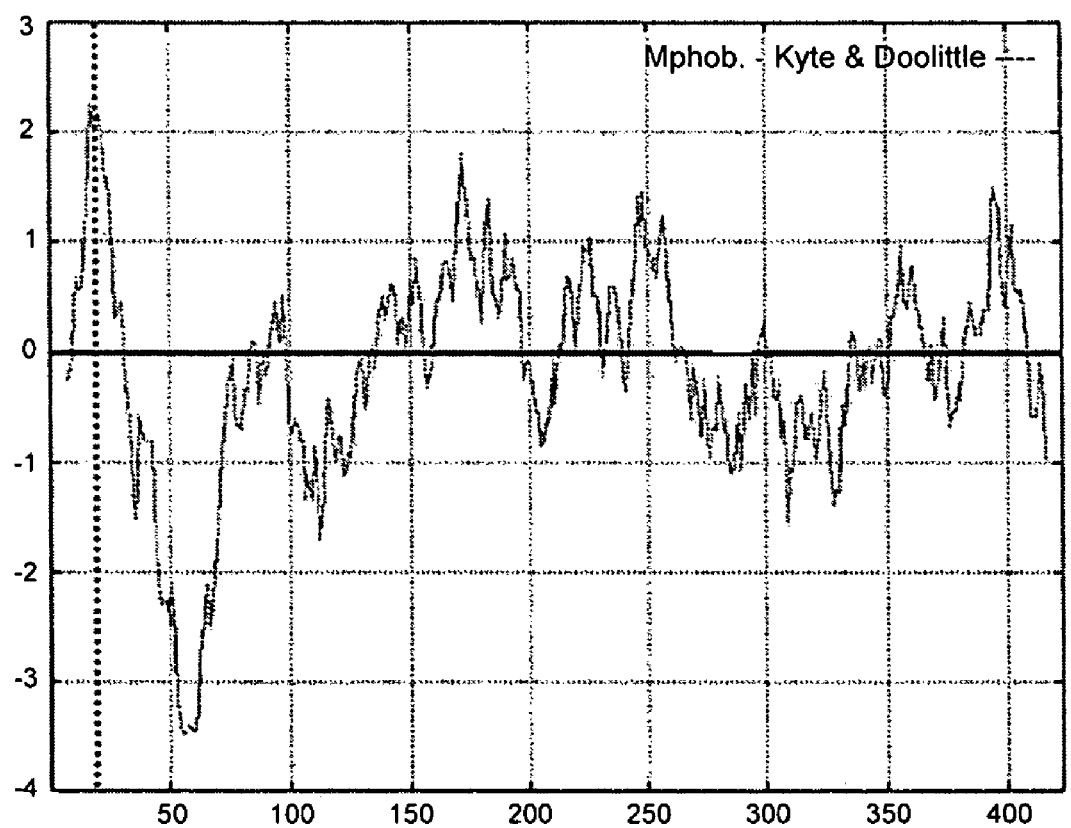
FIG. 1: Comparative analysis of sequences of *T. cruzi* TcPRACA and TcPRACB proline racemase isoforms. A. Alignment of TcPRACA (Tc-A) (SEQ ID NO: 28) and TcPRACB (Tc-B) (SEQ ID NO: 29) nucleotide sequences: non coding sequences are shown in italics; trans-splicing signals are underlined and putative spliced leader acceptor sites are double-underlined; the region encoding the computer-predicted signal peptide is indicated by double-headed arrow; initiation of translation for TcPRACA and TcPRACB are shown by single-headed arrows; nucleotides shaded in light and dark grey, represent respectively silent mutations or point mutations; box, proline racemase active site; UUA triplets are underlined in bold and precede polyadenylation sites that are double-underlined. B. Schematic representation of amino acid sequence alignments of *T. cruzi* TcPRACA (Tc-A), TcPRACB (Tc-B) proline racemases (SEQ ID NOS 30-32, respectively in order of appearance). The common scale is in amino acid residue positions along the linear alignment and represent the initiation codons for TcPRACA and TcPRACB proteins, respectively; ∇ represents an alternative TcPRACA putative initiation codon; Amino acid differences are indicated above and below the vertical lines and their positions in the sequence are shown in parenthesis. SP: signal peptide; the N-terminal domain of TcPRACA extends from positions 1 to 69; SPCGT: conserved active sites of TcPRACA and TcPRACB proline racemases; N-terminus and C-terminus are indicated for both proteins. C. Hydrophobicity profile of TcPRACA: dotted line depicts the cleavage site as predicted by Von Heijne's method (aa 31-32). D. Ethidium bromide-stained gel of chromosomal bands of *T. cruzi* CL Brener clone after separation by PFGE (lane 1) and Southern blot hybridization with TcPRAC probe (lane 2). The sizes (Mb) of chromosomal bands are indicated, as well as the region chromosome numbers in roman numerals.

Proline racemase catalyses the interconversion of L- and D-proline enantiomers and has to date been described in only two species. Originally found in the bacterium *Clostridium sticklandii*, it contains cysteine residues in the active site and does not require cofactors or other known coenzymes. The first eukaryotic amino acid (proline) racemase, after isolation and cloning of a gene from the pathogenic human parasite *Trypanosoma cruzi*, has been described. While this enzyme is intracellularly located in replicative non-infective forms of *T. cruzi*, membrane-bound and secreted forms of the enzyme are present upon differentiation of the parasite into non-dividing infective forms. The secreted isoform of proline racemase is a potent host B-cell mitogen supporting parasite evasion of specific immune responses.

Primarily it was essential to elucidate whether TcPRACB gene could encode a functional proline racemase. To answer this question, TcPRACA and TcPRACB paralogue genes were expressed in *Escherichia coli* and detailed studies were performed on biochemical and enzymatic characteristics of the recombinant proteins. This invention demonstrates that TcPRACB indeed encodes a functional proline racemase that exhibits slightly different kinetic parameters and biochemical characteristics when compared to TcPRACA enzyme. Enzymatic activities of the respective recombinant proteins showed that the 39 kDa intracellular isoform of proline racemase produced by TcPRACB construct is more stable and has higher rate of D/L-proline interconversion than the 45 kDa isoform produced by TcPRACA. Additionally, the dissociation constant of the enzyme-inhibitor complex ($K_i$) obtained with pyrrole-2-carboxylic acid, the specific inhibitor of proline racemases, is lower for the recombinant TcPRACB enzyme.

Moreover, this invention demonstrates that $Cys^{330}$ and $Cys^{160}$ are key amino acids of the proline racemase active site since the activity of the enzyme is totally abolished by site-direct mutagenesis of these residues. Also, multiple alignment of proline racemase amino acid sequences allowed the definition of protein signatures that can be used to identify putative proline racemases in other microorganisms. The significance of the presence of proline racemase in eukaryotes, particularly in *T. cruzi*, is discussed, as well as the consequences of this enzymatic activity in the biology and infectivity of the parasite.

This invention provides amino acid motifs, which are useful as signatures for proline racemaces. These amino acid motifs are as follows:

```
MOTIF I
                                              [SEQ ID NO: 1]
[IVL][GD]XHXXG[ENM]XX[RD]X[VI]XG

MOTIF II
                                              [SEQ ID NO: 2]
[NSM][VA][EP][AS][FY]X(13,14)[GK]X[IVL]XXD[IV][AS]
[YWF]GGX[FWY]

MOTIF III
                                              [SEQ ID NO: 3]
DRSPXGXGXXAXXA

MOTIF III*
                                              [SEQ ID NO: 4]
DRSPCGXGXXAXXA
``` where X is an amino acid in each of these sequences.

This invention also provides polynucleotides encoding amino acid motifs, which are also referred to herein as the "polynucleotides of the invention" and the "polypeptides of the invention."

Databases were screened using these polynucleotide or polypeptide sequences of TcPRACA. Motifs I to III were searched. M I corresponds to [IVL][GD]XHXXG[ENM]XX[RD]X[VI]XXG (SEQ ID NO: 23), M II to of [NSM][VA][EP][AS][FY]X(13,14)[GK]X[IVL]XXD[IV][AS][YWF]GGX[FWY] (SEQ ID NO: 2)M III to DRSPXGXGXX-AXXA (SEQ ID NO: 3) and M III* to DRSPCGXGXX AXXA (SEQ ID NO: 4). Sequences presented in the annex, where the conserved regions of 2 Cysteine residues of the active site are squared, are presented in Table V in bold with corresponding Accession numbers. The two cysteine residues are $Cys^{330}$ and its homologue $Cys^{160}$, where residue $Cys^{160}$ mutation by a serine by site directed mutagenesis also induces a drastic loss of the enzymatic activity as for residue $Cys^{330}$.

Proline racemase, an enzyme previously only described in protobacterium *Clostridium sticklandii* (11), was shown to be encoded also by the eukaryote *Trypanosoma cruzi*, a highly pathogenic protozoan parasite (13). The *Trypanosoma cruzi* proline racemase (TcPRAC), formerly called TcPA45, is an efficient mitogen for host B cells and is secreted by the meta-cyclic forms of the parasite upon infection, contributing to its immune-evasion and persistence through non-specific polyclonal lymphocyte activation (13). Previous results suggested that TcPRAC is encoded by two paralogous genes per haploid genome. Protein localization studies have also indicated that *T. cruzi* can differentially express intracellular and secreted versions of TcPRAC during cell cycle and differentiation, as the protein is found in the cytoplasm of non-infective replicative (epimastigote) forms of the parasite, and bound to the membrane or secreted in the infective, non-replicative (metacyclic trypomastigote) parasites (13).

This invention characterizes the two TcPRAC paralogues and demonstrates that both TcPRACA and TcPRACB give rise to functional isoforms of co-factor independent proline racemases, which display different biochemical properties that may well have important implications in the efficiency of the respective enzymatic activities. As suggested before by biochemical and theoretical studies for the bacterial proline racemase (11,17,18), TcPRAC activities rely on two monomeric enzyme subunits that perform interconversion of L- and/or D-proline enantiomers by a two base mechanism reaction in which the enzyme removes an α-hydrogen from the substrate and donates a proton to the opposite side of the α-carbon. It has been predicted that each subunit of the homodimer furnishes one of the sulfhydryl groups (18).

The present invention demonstrates that TcPRAC enzymatic activities are bona fide dependent on the Cys$^{330}$ residue of the active site, as site-specific $^{330}$Cys>Ser mutation totally abrogates L- and D-proline racemization, in agreement with a previous demonstration that TcPRAC enzymatic activity is abolished through alkylation with iodoacetate or iodoacetamide (13), similarly to the *Clostridium* proline racemase, where carboxymethylation was shown to occur specifically with the two cysteines of the reactive site leading to enzyme inactivation (12). The present invention demonstrates also that the residue Cys$^{160}$ is also a critical residue of the active site and that TcPRAC possesses two active sites in its homodimer. These observations make it possible to search for inhibitors by means of assays based on the native and mutated sequences.

While gene sequence analysis predicted that, by a mechanism of alternative splicing, TcPRACA could generate both intracellular and secreted versions of parasite proline racemase, the present invention demonstrates that TcPRACB gene sequence per se codes for a protein lacking the amino acids involved in peptide signal formation and an extra N-terminal domain present in TcPRACA protein, resembling more closely the CsPR. Thus, TcPRACB can only generate an intracellular version of TcPRAC proline racemase. This discovery makes it possible to carry out a search of one putative inhibitor of an intracellular enzyme should penetrate the cell.

Interestingly, the presence of two homologous copies of TcPRAC genes in the *T. cruzi* genome, coding for two similar polypeptides but with distinct specific biochemical properties, could reflect an evolutionary mechanism of gene duplication and a parasite strategy to ensure a better environmental flexibility. This assumption is comforted by the potential of TcPRACA gene to generate two related protein isoforms by alternative splicing, a mechanism that is particularly adept for cells that must respond rapidly to environmental stimuli. Primarily, trans-splicing appears indeed to be an ancient process that may constitute a selective advantage for split genes in higher organisms (19) and alternative trans-splicing was only recently proven to occur in *T. cruzi* (20). As an alternative for promoter selection, the regulated production of intracellular and/or secreted isoforms of proline racemase in *T. cruzi* by alternative trans-splicing of TcPRACA gene would allow the stringent conservation of a constant protein domain and/or the possibility of acquisition of an additional secretory region domain. As a matter of fact, recent investigations using RT-PCR based strategy and a common 3' probe to TcPRACA and TcPRACB sequences combined to a 5' spliced leader oligonucleotide followed by cloning and sequencing of the resulting fragments have indeed proved that an intracellular version of TcPRAC may also originate from the TcPRACA gene, corroborating this hypothesis.

Gene duplication is a relatively common event in *T. cruzi* that adds complexity to parasite genomic studies. Moreover, TcPRAC chromosomal mapping revealed two chromosomal bands that possess more than 3 chromosomes each and that may indicate that proline racemase genes are mapped in size-polymorphic homologous chromosomes, an important finding for proline racemase gene family characterization. Preliminary results have, for instance, revealed that *T. cruzi* DM28c type I strain maps proline racemase genes to the same chromoblot regions identified with *T. cruzi* CL type II strain used in the present invention.

It is well known that proline constitutes an important source of energy for several organisms, such as several hemoflagellates (21),(22),(23), and for flight muscles in insects (24). Furthermore, a proline oxidase system was suggested in trypanosomes (25) and the studies reporting the abundance of proline in triatominae guts (26) have implicated proline in metabolic pathways of *Trypanosoma cruzi* parasites as well as in its differentiation in the digestive tract of the insect vector (27). Thus, it is well accepted that *T. cruzi* can use L-proline as a principal source of carbon (25).

Moreover, preliminary results using parasites cultured in defined media indicate that both epimastigotes, found in the vector, and infective metacyclic trypomastigote forms can efficiently metabolize L- or D-proline as the sole source of carbon. While certain reports indicate that biosynthesis of proline occurs in trypanosomes, i.e. via reduction of glutamate carbon chains or transamination reactions, an additional and direct physiological regulation of proline might exist in the parasite to control amino acid oxidation and its subsequent degradation or yet to allow proline utilization. In fact, a recent report showed two active proline transporter systems in *T. cruzi* (28). *T. cruzi* proline racemase may possibly play a consequential role in the regulation of intracellular proline metabolic pathways, or else, it could participate in mechanisms of post-translational addition of D-amino acid to polypeptide chains.

On one hand, these hypotheses would allow for an energy gain and, on the other hand, would permit the parasite to evade host responses. In this respect, it was reported that a single D-amino acid addition in the N-terminus of a protein is sufficient to confer general resistance to lytic reactions involving host proteolytic enzymes (29). The expression of proteins containing D-amino acids in the parasite membrane would benefit the parasite inside host cell lysosomes, in addition to the contribution to the initiation of polyclonal activation, as already described for polymers composed of D-enantiomers (30), (31). Although D-amino acid inclusion in *T. cruzi* proteins would benefit the parasite, this hypothesis remains to be proven and direct evidence is technically difficult to obtain.

It is worth noting that metacyclogenesis of epimastigotes into infective metacyclic forms involves parasite morphologic changes that include the migration of the kinetoplast, a structure that is physically linked to the parasite flagellum, and many other significant metabolic alterations that combine to confer infectivity/virulence to the parasite (13,32). Proline racemase was shown to be preferentially localized in the flagellar pocket of infective parasite forms after metacyclogenesis (13), as are many other known proteins secreted and involved in early infection (33).

It is also conceivable that parasite proline racemase may function as an early mediator for *T. cruzi* differentiation through intracellular modification of internalized environmental free proline, as suggested above and already observed in some bacterial systems. As an illustration, exogenous alanine has been described as playing an important role in bacterial transcriptional regulation by controlling an operon formed by genes coding for alanine racemase and a smaller subunit of bacterial dehydrogenase (34).

In bacteria, membrane alanine receptors are responsible for alanine and proline entry into the bacterial cell (35). It can then be hypothesized that the availability of proline in the insect gut milieu associated to a mechanism of environmental sensing by specific receptors in the parasite membrane would stand for parasite proline uptake and its further intracellular racemization. Proline racemase would then play a fundamental role in the regulation of parasite growth and differentiation by its participation in both metabolic energetic pathways and the expression of proteins containing D-proline, as described above, consequently conferring parasite infectivity and its ability to escape host specific responses.

Thus far, and contrasting to the intracellular isoform of TcPRAC found in epimastigote forms of *T. cruzi*, the ability of metacyclic and bloodstream forms of the parasite to express and secrete proline racemase may have further implications in host/parasite interaction. In fact, the parasite-secreted isoform of proline racemase participates actively in the induction of non-specific polyclonal B-cell responses upon host infection (13) and favors parasite evasion, thus ensuring its persistence in the host.

As described for other mitogens and parasite antigens (36), (37), (38), and in addition to its mitogenic property, TcPRAC could also be involved in modifications of host cell targets enabling better parasite attachment to host cell membranes in turn assuring improved infectivity. Since several reports associate accumulation of L-proline with muscular dysfunction (39) and inhibition of muscle contraction (40), the release of proline racemase by intracellular parasites could alternatively contribute to the maintenance of infection through regulation of L-proline concentration inside host cells, as proline was described as essential for the integrity of muscular cell targets. Therefore, it has recently been demonstrated that transgenic parasites hyperexpressing TcPRACA or TcPRACB genes, but not functional knock outs, are 5-10 times more infective to host target cells pointing to a critical role of proline racemases in the ongoing of the infectious process. Likewise, previous reports demonstrated that genetic inactivation of *Lysteria monocytogenes* alanine racemase and D-amino acid oxidase genes abolishes bacterial pathogenicity, since the presence of D-alanine is required for the synthesis of the mucopeptide component of the cell wall that protects virtually all bacteria from the external milieu (41).

Present analysis using identified critical conserved residues in TcPRAC and *C. sticklandii* proline racemase genes and the screening of SWISS-PROT and TrEMBL databases led to the discovery of a minimal signature for proline racemases, DRSPXGX[GA]XXAXXA (SEQ ID NO: 24), and to confirm the presence of putative proteins in at least 10 distinct organisms. Screening of unfinished genome sequences showed highly homologous proline racemase candidate genes in an additional 8 organisms, amongst which are the fungus *Aspergillus fumigatus* and the bacteria *Bacillus anthracis* and *Clostridium botulinum*. This is of particular interest, since racemases, but not proline racemases, are widespread in bacteria and only recently described in more complex organisms such as *T. cruzi*, 42,43). These findings may possibly reflect cell adaptive responses to extracellular stimuli and uncover more general mechanisms for the regulation of gene expression by D-amino acids in eukaryotes. The finding of similar genes in human and mouse genome databases using less stringent signatures for proline racemase is striking. However, the absence of the crucial amino acid cysteine in the putative active site of those predicted proteins suggests a different functionality than that of a proline racemase.

This invention shows that TcPRAC isoforms are highly stable and have the capacity to perform their activities across a large spectrum of pH. In addition, the affinity of pyrrolcarboxylic acid, a specific inhibitor of proline racemase, is higher for TcPRAC enzymes than for CsPR.

The invention also provides amino acid or nucleic acid sequences substantially similar to specific sequences disclosed herein.

The term "substantially similar" when used to define either amino acid or nucleic acid sequences means that a particular subject sequence, for example, a mutant sequence, varies from a reference sequence by one or more substitutions, deletions, or additions, the net effect of which is to retain activity. Alternatively, nucleic acid subunits and analogs are "substantially similar" to the specific DNA sequences disclosed herein if: (a) the DNA sequence is derived from a region of the invention; (b) the DNA sequence is capable of hybridization to DNA sequences of (a) and/or which encodes active molecules; or DNA sequences that are degenerate as a result of the genetic code to the DNA sequences defined in (a) or (b) and/or which encode active molecules.

In order to preserve the activity, deletions and substitutions will preferably result in homologously or conservatively substituted sequences, meaning that a given residue is replaced by a biologically similar residue. Examples of conservative substitutions include substitution of one aliphatic residue for another, such as Ile, Val, Leu, or Ala for one another, or substitution of one polar residue for another, such as between Lys and Arg; Glu and Asp; or Gln and Asn. Other such conservative substitutions, for example, substitutions of entire regions having similar hydrophobicity characteristics, are well known. When said activity is proline racemase activity, $Cys^{330}$ and $Cys^{160}$ must be present.

The polynucleotides of the invention can be used as probes or to select nucleotide primers notably for an amplification reaction. PCR is described in the U.S. Pat. No. 4,683,202 granted to Cetus Corp. The amplified fragments can be identified by agarose or polyacrylamide gel electrophoresis, or by a capillary electrophoresis, or alternatively by a chromatography technique (gel filtration, hydrophobic chromatography, or ion exchange chromatography). The specificity of the amplification can be ensured by a molecular hybridization using as nucleic acid probes the polynucleotides of the invention, oligonucleotides that are complementary to these polynucleotides, or their amplification products themselves.

Amplified nucleotide fragments are useful as probes in hybridization reactions in order to detect the presence of one polynucleotide according to the present invention or in order to detect the presence of a gene encoding racemase activity, such as in a biological sample. This invention also provides the amplified nucleic acid fragments ("amplicons") defined herein above. These probes and amplicons can be radioactively or non-radioactively labeled using, for example, enzymes or fluorescent compounds.

Other techniques related to nucleic acid amplification can also be used alternatively to the PCR technique. The Strand Displacement Amplification (SDA) technique (Walker et al., 1992) is an isothermal amplification technique based on the ability of a restriction enzyme to cleave one of the strands at a recognition site (which is under a hemiphosphorothioate form), and on the property of a DNA polymerase to initiate the synthesis of a new strand from the 3' OH end generated by the restriction enzyme, and on the property of this DNA polymerase to displace the previously synthesized strand being localized downstream.

The SDA amplification technique is more easily performed than PCR (a single thermostated water bath device is necessary), and is faster than the other amplification methods. Thus, the present invention also comprises using the nucleic acid fragments according to the invention (primers) in a method of DNA or RNA amplification, such as the SDA technique.

The polynucleotides of the invention, especially the primers according to the invention, are useful as technical means for performing different target nucleic acid amplification methods, such as:

TAS (Transcription-based Amplification System), described by Kwoh et al. in 1989;

SR (Self-Sustained Sequence Replication), described by Guatelli et al. in 1990;

NASBA (Nucleic acid Sequence Based Amplification), described by Kievitis et al. in 1991; and TMA (Transcription Mediated Amplification).

The polynucleotides of the invention, especially the primers according to the invention, are also useful as technical means for performing methods for amplification or modification of a nucleic acid used as a probe, such as:

LCR (Ligase Chain Reaction), described by Landegren et al. in 1988 and improved by Barany et al. in 1991, who employ a thermostable ligase;

RCR (Repair Chain Reaction), described by Segev et al. in 1992;

CPR (Cycling Probe Reaction), described by Duck et al. in 1990; and

Q-beta replicase reaction, described by Miele et al. in 1983 and improved by Chu et al. in 1986, Lizardi et al. in 1988, and by Burg et al. and Stone et al. in 1996.

When the target polynucleotide to be detected is RNA, for example mRNA, a reverse transcriptase enzyme can be used before the amplification reaction in order to obtain a cDNA from the RNA contained in the biological sample. The generated cDNA can be subsequently used as the nucleic acid target for the primers or the probes used in an amplification process or a detection process according to the present invention.

The oligonucleotide probes according to the present invention hybridize specifically with a DNA or RNA molecule comprising all or part of the polynucleotide of the invention under stringent conditions. As an illustrative embodiment, the stringent hybridization conditions used in order to specifically detect a polynucleotide according to the present invention are advantageously the following:

Prehybridization and hybridization are performed as follows in order to increase the probability for heterologous hybridization:

The prehybridization and hybridization are done at 50° C. in a solution containing 5×SSC and 1× Denhardt's solution.

The washings are performed as follows:

2×SSC at 60° C. 3 times during 20 minutes each.

The non-labeled polynucleotides of the invention can be directly used as probes. Nevertheless, the polynucleotides can generally be labeled with a radioactive element ($^{32}P$, $^{35}S$, $^{3}H$, 125I) or by a non-isotopic molecule (for example, biotin, acetylaminofluorene, digoxigenin, 5-bromodesoxyuridin, fluorescein) in order to generate probes that are useful for numerous applications. Examples of non-radioactive labeling of nucleic acid fragments are described in the French Patent No. FR 78 10975 or by Urdea et al. or Sanchez-Pescador et al. 1988.

Other labeling techniques can also be used, such as those described in the French patents 2 422 956 and 2 518 755. The hybridization step can be performed in different ways. A general method comprises immobilizing the nucleic acid that has been extracted from the biological sample on a substrate (nitrocellulose, nylon, polystyrene) and then incubating, in defined conditions, the target nucleic acid with the probe. Subsequent to the hybridization step, the excess amount of the specific probe is discarded, and the hybrid molecules formed are detected by an appropriate method (radioactivity, fluorescence, or enzyme activity measurement).

Advantageously, the probes according to the present invention can have structural characteristics such that they allow signal amplification, such structural characteristics being, for example, branched DNA probes as those described by Urdea et al. in 1991 or in the European Patent No. 0 225 807 (Chiron).

In another advantageous embodiment of the present invention, the probes described herein can be used as "capture probes", and are for this purpose immobilized on a substrate in order to capture the target nucleic acid contained in a biological sample. The captured target nucleic acid is subsequently detected with a second probe, which recognizes a sequence of the target nucleic acid that is different from the sequence recognized by the capture probe.

The oligonucleotide probes according to the present invention can also be used in a detection device comprising a matrix library of probes immobilized on a substrate, the sequence of each probe of a given length being localized in a shift of one or several bases, one from the other, each probe of the matrix library thus being complementary to a distinct sequence of the target nucleic acid. Optionally, the substrate of the matrix can be a material able to act as an electron donor, the detection of the matrix positions in which hybridization has occurred being subsequently determined by an electronic device. Such matrix libraries of probes and methods of specific detection of a target nucleic acid are described in European patent application No. 0 713 016, or PCT Application No. WO 95 33846, or also PCT Application No. WO 95 11995 (Affymax Technologies), PCT Application No. WO 97 02357 (Affymetrix Inc.), and also in U.S. Pat. No. 5,202,231 (Drmanac), said patents and patent applications being herein incorporated by reference.

The present invention also pertains to recombinant plasmids containing at least a nucleic acid according to the invention. A suitable vector for the expression in bacteria, and in particular in *E. coli*, is pET-28 (Novagen), which allows the production of a recombinant protein containing a 6×His affinity tag (SEQ ID NO: 129). The 6×His tag (SEQ ID NO: 129) is placed at the C-terminus or N-terminus of the recombinant polypeptide.

The polypeptides according to the invention can also be prepared by conventional methods of chemical synthesis, either in a homogenous solution or in solid phase. As an illustrative embodiment of such chemical polypeptide synthesis techniques, the homogenous solution technique described by Houbenweyl in 1974 may be cited.

The polypeptides of the invention are useful for the preparation of polyclonal or monoclonal antibodies that recognize the polypeptides (SEQ ID NOS: 1, 2, 3, and 4) or fragments thereof. The monoclonal antibodies can be prepared from hybridomas according to the technique described by Kohler and Milstein in 1975. The polyclonal antibodies can be prepared by immunization of a mammal, especially a mouse or a rabbit, with a polypeptide according to the invention, which is combined with an adjuvant, and then by purifying specific antibodies contained in the serum of the immunized animal on a affinity chromatography column on which has previously been immobilized the polypeptide that has been used as the antigen.

A method of detecting a racemase encoded by a nucleotide sequence containing a subsequence encoding a peptide selected from SEQ ID NOS: 1, 2, 3, or 4.

Consequently, the invention is also directed to a method for detecting specifically the presence of a polypeptide according to the invention in a biological sample. The method comprises:

a) bringing into contact the biological sample with an antibody according to the invention; and b) detecting antigen-antibody complex formed.

Also part of the invention is a diagnostic kit for in vitro detecting the presence of a polypeptide according to the present invention in a biological sample. The kit comprises:
- a polyclonal or monoclonal antibody as described above, optionally labeled; and
- a reagent allowing the detection of the antigen-antibody complexes formed, wherein the reagent carries optionally a label, or being able to be recognized itself by a labeled reagent, more particularly in the case when the above-mentioned monoclonal or polyclonal antibody is not labeled by itself.

The present invention is also directed to bioinformatic searches in data banks using the whole sequences of the polypeptides using the whole sequences of the polypeptides (SEQ ID NOS: 1, 2, 3, or 4). In this case the method detects the presence of at least a subsequence encoding a peptide selected from SEQ ID NOS: 1, 2, 3, or 4 wherein the said at least subsequence is indicative of a racemase.

The invention also pertains to:
A purified polypeptide or a peptide fragment having at least 10 amino acids, which is recognized by antibodies directed against a polynucleotide or peptide sequence according to the invention.
A monoclonal or polyclonal antibody directed against a polypeptide or a peptide fragment encoded by the polynucleotide sequences according to the invention.
A method of detecting a racemase in a biological sample comprising:
  a) contacting DNA or RNA of the biological sample with a primer or a probe from a polynucleotide according to the invention, which hybridizes with a nucleotide sequence;
  b) amplifying the nucleotide sequence using the primer or said probe; and
  c) detecting the hybridized complex formed between the primer or probe with the DNA or RNA.
A kit for detecting the presence of a racemase in a biological sample, comprises:
  a) a polynucleotide primer or probe according to the invention; and
  b) reagents necessary to perform a nucleic acid hybridization reaction.
An in vitro method of screening for an active molecule capable of inhibiting a racemase encoded by a nucleic acid containing a polynucleotide according to the invention, wherein the inhibiting activity of the molecule is tested on at least said racemase, comprises:
  a) providing racemase containing a polypeptide according to the invention;
  b) contacting the active molecule with said racemase;
  c) testing the capacity of the active molecule, at various concentrations, to inhibit the activity of the racemase; and
  d) choosing the active molecule that provides an inhibitory effect of at least 80% on the activity of the racemase.

The term "recombinant" as used herein means that a protein or polypeptide employed in the invention is derived from recombinant (e.g., microbial or mammalian) expression systems. "Microbial" refers to recombinant proteins or polypeptides made in bacterial or fungal (e.g., yeast) expression systems. As a product, "recombinant microbial" defines a protein or polypeptide produced in a microbial expression system, which is essentially free of native endogenous substances. Proteins or polypeptides expressed in most bacterial cultures, e.g. E. coli, will be free of glycan. Proteins or polypeptides expressed in yeast may have a glycosylation pattern different from that expressed in mammalian cells.

The polypeptide or polynucleotide of this invention can be in isolated or purified form. The terms "isolated" or "purified", as used in the context of this specification to define the purity of protein or polypeptide compositions, means that the protein or polypeptide composition is substantially free of other proteins of natural or endogenous origin and contains less than about 1% by mass of protein contaminants residual of production processes. Such compositions, however, can contain other proteins added as stabilizers, excipients, or co-therapeutics. These properties similarly apply to polynucleotides of the invention.

The platform of the invention relates to reagents, systems and devices for performing the process of screening of D-amino acid tests.

Appropriate carriers, diluents, and adjuvants can be combined with the polypeptides and polynucleotides described herein in order to prepare the compositions of the invention. The compositions of this invention contain the polypeptides or polynucleotides together with a solid or liquid acceptable nontoxic carrier. Such carriers can be sterile liquids, such as water an oils, including those of petroleum, animal, vegetable, or synthetic origin. Examples of suitable liquids are peanut oil, soybean oil, mineral oil, sesame oil and the like. Water is a preferred carrier. Physiological solutions can also be employed as liquid carriers.

This invention will now be described with reference to the following Examples.

EXAMPLE 1

Cloning and Automated Sequencing

Lambda phage and plasmid DNA were prepared using standard techniques and direct sequencing was accomplished with the Big dye Terminator Kit (Perkin Elmer, Montigny-le Bretonneux, France) according to the manufacturer's instructions. Extension products were run for 7 h in an ABI 377 automated sequencer. Briefly, to obtain the full length of the TcPRAC gene, $^{32}$P-labeled 239 bp PCR product was used as a probe to screen a T. cruzi clone CL-Brener Iamba Fix II genomic library (see details in (13)). There were isolated 4 independent positive phages. Restriction analysis and Southern blot hybridization showed two types of genomic fragments, each represented by 2 phages. Complete sequence and flanking regions of representative phages for each pattern was done. Complete characterization of TcPRACA gene, representing the first phage type, was previously described in (13). Full sequence of the putative TcPRACB gene, representing the second phage type was then performed and primers internal to the sequence were used for sequencing, as described before (13).

EXAMPLE 2

Chromoblots

Epimastigote forms T. cruzi (clone CL Brener) are maintained by weekly passage in LIT medium. Agarose (0.7%) blocks containing $1 \times 10^7$ cultured parasites were lysed with 0.5 M EDTA/10 mM Tris/1% sarcosyl pH 8.0, digested by proteinase K and washed in 10 mM Tris/1 mM EDTA, pH 8.0. Pulsed field gel electrophoresis (PFGE) was carried out at 18° C. using the Gene Navigator apparatus (Pharmacia, Upsala, Sweden) in 0.5×TBE. Electrophoresis were performed, as described in (14). Gels were then stained with ethidium bromide, photographed, exposed to UV light (265 nm) for 5 min and further blotted under alkaline conditions to a nylon filter (HybondN+, Amersham Life Science Inc., Cleveland, USA). DNA probe, obtained by PCR amplification of TcPRACA gene with Hi-45 (5' CTC TCC CAT GGG GCA GGA AAA GCT TCT G 3') [SEQ ID NO:5] and Bg-45 (5' CTG AGC TCG ACC AGA T(CA)T ACT GC 3') [SEQ ID NO:6] oligonucleotides (as described in (13)) was labelled with $\alpha dATP^{32}$ using Megaprime DNA labelling system (Amersham). The chromoblot was hybridized overnight in 2× Denhart's/5× SSPE/1.5% SDS at 55° C. and washed in 2×SSPE/0.1% SDS followed by 1×SSPE at 60° C. Autoradiography was obtained by overnight exposure of the chromoblot using a Phosphorimager cassette (Molecular Dynamics, UK).

EXAMPLE 3

Plasmid Construction and Protein Purification

TcPRACA gene fragment starting at codon 30 was obtained by PCR, using Hi- and Bg-45 primers, and cloned in frame with a C-terminal six-histidine tag into the pET28b(+) expression vector (Novagen-Tebu, Le Perray en Yvelines, France). The fragment encoding for the TcPRACB consisted of a HindIII digestion of TcPRACB gene fragment obtained by similar PCR and cloned in frame with a C-terminal six-histidine tag into the pET28b(+) expression vector. Respective recombinant proteins TcPRACA and TcPRACB were produced in *E coli* BL21 (DE3) (Invitrogen, Cergy Pontoise, France) and purified using Immobilized Metal Affinity Chromatography on nickel columns (Novagen-Tebu, Le Parrayen Yvelines, France) following the manufacturer's instructions.

EXAMPLE 4

Size Exclusion Chromatography rTcPRACA and rTcPRACB proteins were purified as described here above and dialysed against PBS pH 7.4 or 0.2 M NaOAc pH 6.0 elution buffers in dialysis cassettes (Slide-A-lyzer 7K Pierce), overnight at 4° C. The final protein concentration was adjusted to 2 mg/ml and 0.5 ml of the solution were loaded onto Pharmacia Superdex 75 column (HR10× 30), previously calibrated with a medium range protein calibration kit (Pharmacia). Size exclusion chromatography (SEC) was carried out using an FPLC system (AKTA Purifier, Pharmacia). Elution was performed at a constant flow rate of 0.5 ml/min, protein fractions of 0.5 ml were collected and the absorbance was monitored at 280 nm. Each fraction was assayed in racemization assays as described here below. Fractions B1 and B5, were reloaded in the Superdex 75 column and submitted to a further SEC to verify the purity of the fractions.

EXAMPLE 5

Racemization Assays

The percent of racemization with different concentrations of L-proline, D-proline, L-hydroxy (OH)-proline, D-hydroxy (OH)-proline was calculated, as described in (13), by incubating a 500 μl mixture of 0.25 μM of dimeric protein and 40 mM substrate in 0.2 M sodium acetate pH 6.0 for 30 min or 1 h at 37° C. The reaction was stopped by incubating for 10 min at 80° C. and freezing. Water (1 ml) was then added, and the optical rotation was measured in a polarimeter 241 MC (Perkin Elmer, Montigny le Bretonneux, France) at a wavelength of 365 nm, in a cell with a path length of 10 cm, at a precision of 0.001 degree. The percent of racemization of 40 mM L-proline as a function of pH was determined using 0.2 M sodium acetate, potassium phosphate and Tris-HCl buffers; reactions were incubated 30 min at 37° C., as described above. All reagents were purchased from Sigma.

EXAMPLE 6

Kinetic Assays

Concentrations of L- and D-proline were determined polarimetrically from the optical rotation of the solution at 365 nm in a cell of 10 cm path length, thermostated at 37° C. Preliminary assays were done with 40 mM of L-proline in 0.2 M sodium acetate pH 6 in a final volume of 1.5 ml. Optical rotation was measured every 5 sec during 10 min and every 5 min to 1 hour. After determination of the linear part of the curve, velocity in 5-160 mM substrate was measured every 30 sec during 10 min to determine $K_M$ and $V_{max}$. Calculations were done using the Kaleïdagraph program. Inhibition assays were done by incubating 0.125 μM dimeric protein, 6,7 μM-6 mM pyrrole-2-carboxylic acid (PAC), 20 to 160 mM L-proline, as described above. Graphic representation and linear curve regression allowed the determination of $K_i$ as [PAC]/ [(slope with PAC/slope without PAC)–1]. All reagents were purchased from Sigma.

EXAMPLE 7

Site-directed Mutagenesis of $^{C330S}$TcPRACA

Figure 5:
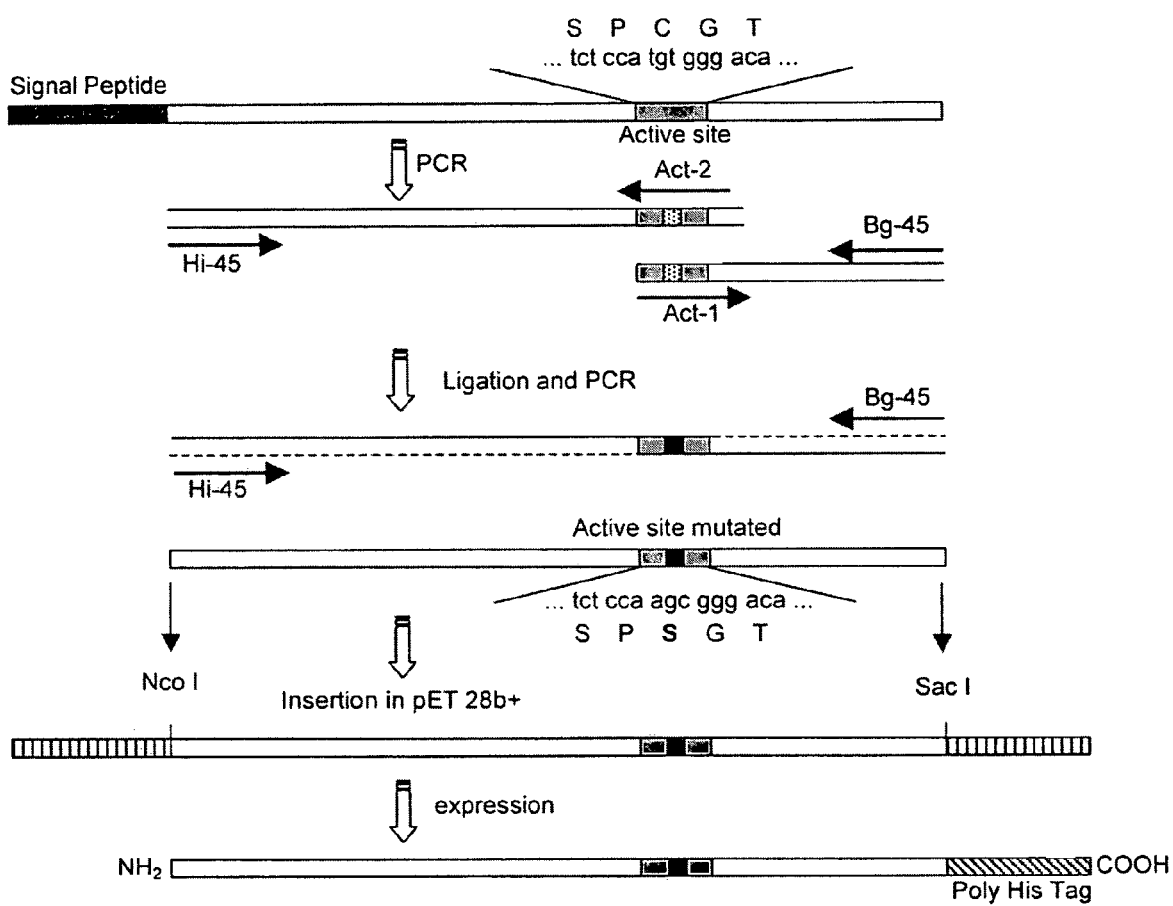
FIG. 5: Site-directed mutagenesis of TcPRACA proline racemase. Schematic representation of the active site mutagenesis of proline racemase of TcPRACA gene (SEQ ID NO: 53 encodes SEQ ID NO: 54, and SEQ ID NO: 55 encodes SEQ ID NO: 56).

Site-directed mutagenesis was performed by PCR, adapting the method of Higuchi et al. (15). Briefly, mutation of $Cys^{330}$ of the proline racemase active site was produced by two successive polymerase chain reactions based on site-directed mutagenesis using two overlapping mutagenic primers: (act-1) 5' GCG GAT CGC TCT CCA <u>AGC</u> GGG ACA GGC ACC 3' [SEQ ID NO:7] and (act-2) 5' GGT GCC TGT CCC <u>GCT</u> TGG AGA GCG ATC CGC 3', [SEQ ID NO:8] designed to introduce a single codon mutation in the active site by replacement of the cysteine (TGT) at the position 330 by a serin (AGC). A first step standard PCR amplification was performed using the TcPRACA DNA as template and a mixture of act-1 primer and the reverse C-terminus primer (Bg-45) 5' CTG AGC TCG ACC AGA T(CA)T ACT GC 3' (SEQ ID NO: 6) (codon 423), or a mixture of act-2 primer and the forward N-terminus primer (Hi-45) 5' CTC TCC CAT GGG GCA GGA AAA GCT TCT G 3' (SEQ ID NO: 5) (codon –53) (see FIG. 5). Resulting amplified fragments of, respectively, 316 bp and 918 bp were purified by Qiagen PCR extraction kit (Qiagen, Courtaboeuf, France), as prescribed, and further ligated by T4 ligase to generate a template consisting of the full length of a potentially mutated TcPRACA* coding sequence used for the second step PCR. Amplification of this template was performed using forward Hi-45 and reverse Bg-45 primers and the resulting TcPRACA* fragment encoding for the mature proline racemase was purified and cloned in pCR®2.1-TOPO® vector (Invitrogen). TOP10 competent *E. coli* were transformed with the pCR®2.1-TOPO®-TcPRACA* construct and plasmid DNA isolated from individual clones prepared for DNA sequencing. Positive mutants were then sub-cloned in frame with a C-terminal six-histidine tag into the Nco I/Sac I sites of the pET 28b(+) expression vector (Novagen-Tebu, Le Parrayen Yvelines, France). Sub-clones of pET28b(+)-TcPRACA* produced in *E. coli* (DH5α) were sequenced again to confirm the presence of the mutation. Soluble recombinant $^{C330S}$TcPRACA protein was produced in *E. coli* BL21(DE3) (Invitrogen) and purified using a nickel column (Novagen-Tebu), according the manufacturer's instructions.

EXAMPLE 8

Mutagenesis

To verify the implication of the residue Cys160 in the reaction mechanism of the proline racemase, a site specific mutagenesis was performed to replace the residue Cys160 by a Serine, similarly to mutation described for Cys330 residue (see Example 7). Briefly, the site specific mutagenesis was performed by PCR using the following primers:

```
Ser160-Forward:
5'GGCTATTTAAATATGTCTGGACATAACTCAATTGCAGCG3'

Ser160-Reverse:
5'CGCTGCAATTGAGTTATGTCCAGACATATTTAAATAGC3'
```

The presence of the mutation Cystein-Serine was verified by sequencing of the respective plasmids containing the PCR products, as shown here below. The plasmid pET-C160S was used to transform *E. coli* BL21(DE3) and to produce the corresponding recombinant mutated protein.

(SEQ ID NOS 12, 11, 13-16, 18, 17, and 19-22, respectively in order of appearance)

```
            139 M  D  T  C  G  Y  L  N  M  C  G  H  N  G  I  A  A
            145 pET-TcPRAC  499 ATCGATACCGCTGGCTATTTAAATATGTGTGGACATAACTCAATTGCAGCG
            550

Ser160-F/R      GGCTATTTAAATATGTCTGGACATAACTCAATTGCAGCG
            550 pET-C160S   499 ATGGATACCGGTGGCTATTTAAATATGTCTGGACATAACTCAATTGCAGCG
            550 pET-C330S   499 ATGGATACCGGTGGCTATTTAAATATGTGTGGACATAACTCAATTGCAGCG
            550

139 M  D  T  C  G  Y  L  N  M  S  G  H  N  G  I  A  A
            145

318 V  I  F  G  N  R  Q  A  D  R  S  P  C  G  T  C  T
            334 pET-TcPRAC  999 GTGATATTTGGCAATCGCCAGGCGGATCGCTCTCCATGTGGGACAGGCACC
            1050

Ser330-F/R      GCGGATCGCTCTCCAAGCGGGACAGGCACC
            1050 pET-C160S   999 GTGATATTTGGCAATCGCCAGGCGGATCGCTCTCCATGTGGGACAGGCACC
            1050 pET-C330S   999 GTGATATTTGGCAATCGCCAGGCGGATCGCTCTCCAAGCGGGACAGGCACC
            1050

318 V  I  F  G  N  R  Q  A  D  R  S  P  S  G  T  C  T
            334
```

Underlined are the primer sequences used for the site specific mutageneses. The mutations Cys→Ser are represented in bold and underlined for both Cys160 and Cys330 residues.

EXAMPLE 9

Expression of a Functional Intracellular Isoform of Proline Racemase

Figure 1D:
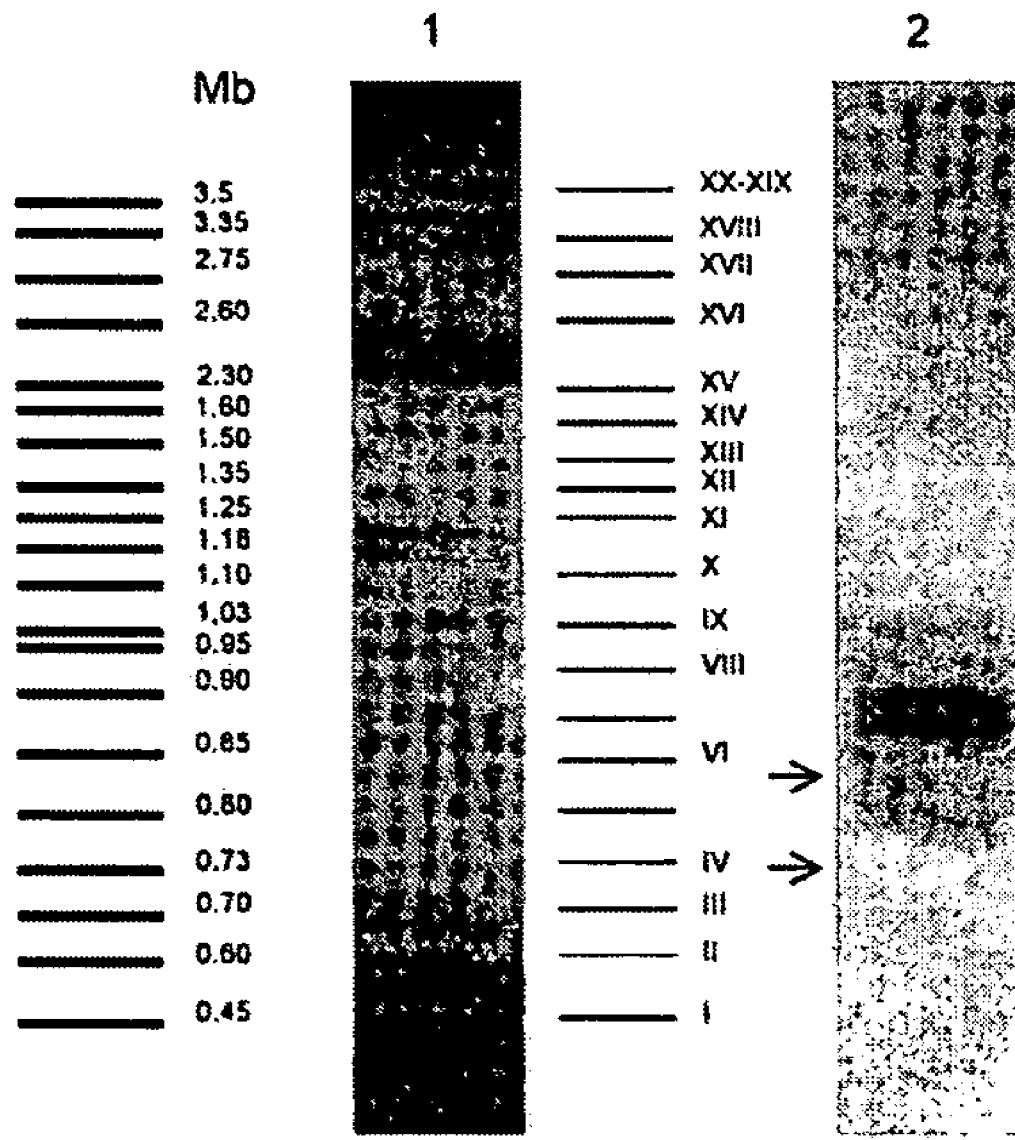

Previously characterized was a TcPRAC gene from *T. cruzi*, and it was demonstrated in vivo and in vitro that it encodes a proline racemase enzyme (13). Analysis of the genomic organization and transcription of the TcPRAC gene indicated the presence of two paralogue gene copies per haploid genome, named TcPRACA[1] and TcPRACB[2]. It was shown that TcPRACA encodes a functional co-factor independent proline racemase, closely resembling the *C. sticklandii* proline racemase (CsPR) (11). Now sequenced was the full length of TcPRACB and, as can be observed in FIG. 1A, TcPRACA and TcPRACB genes both possess the characteristic trypanosome polypyrimidine-rich motifs in the intergenic region that are crucial trans-splicing signals when located upstream of an (AG)-dinucleotide used as acceptor site. As in other *T. cruzi* genes, UUA triplets are found at the end of the 3' untranslated region preceding the polyadenylation site. Comparison between the two sequences revealed 14 point mutations (resulting in 96% identity) giving rise to 7 amino acid differences. When expressed, the TcPRACB is predicted to produce a shorter protein (39 kDa) whose translation would start at the ATG codon at position 274 located downstream of the (AG)-spliced leader acceptor site (at position 175). In comparison, TcPRACA has an open reading frame that encodes a peptide with an apparent molecular mass of 45 kDa. The schematic protein sequence alignment of the two proteins TcPRACA and TcPRACB depicted in FIG. 1B reveals that TcPRACB proline racemase lacks the amino acid sequence corresponding to the signal peptide observed in the TcPRACA protein (hatched box in the figure; see predicted cleavage site in FIG. 1C). Therefore the TcPRACB would produce a 39 kDa, intracellular and non-secreted isoform of the protein. As with CsPR (11) and TcPRACA (13 and FIG. 1B), the active site of proline racemase is conserved in TcPRACB sequence. Furthermore, while differing by only 7 amino acids, both the TcPRACA and TcPRACB sequences display around 50% homology to the CsPR (13). In accordance with other protein-coding genes in *T. cruzi*, TcPRAC genes are located on two different chromosomal bands of which one contains three or more chromosomes of similar size, see FIG. 1D. Thus, hybridization of blots containing *T. cruzi* CL Brener chromosomal bands separated by pulsed field gel electrophoresis revealed that sequences recognized by an homologous probe to both TcPRACA and TcPRACB are mapped in neighboring migrating bands of approximately 0.9 Mb and 0.8 Mb, corresponding respectively to regions VII and V, according to Cano et al. numbering system (14).

Figure 2A:
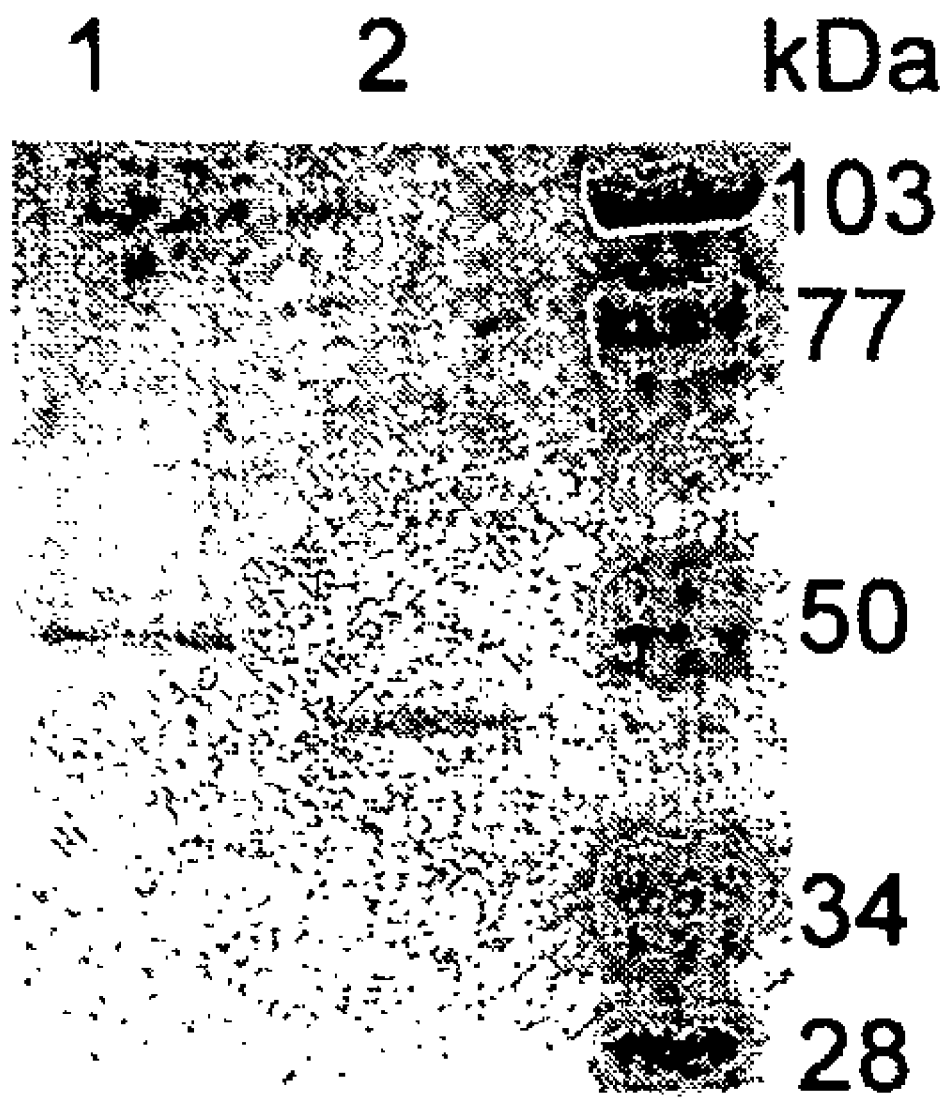
FIG. 2: Biochemical characterization of *T. cruzi* proline racemase isoforms and substrate specificities. A. SDS-PAGE analysis of purified rTcPRACA (lane 1) and rTcPRACB (lane 2) recombinant proteins. A 8% polyacrylamide gel was stained with Coomassie blue. Right margin, molecular weights. B. Percent of racemization of L-proline, D-proline, L-hydroxy (OH) proline and D-hydroxy (OH) proline substrates by rTcPRACB (open bar) as compared to rTcPRACA (closed bar). Racemase activity was determined with 0.25 µM of each isoform of proline racemase and 40 mM substrate in sodium acetate buffer pH 6.0. C. Percent of racemization as a function of pH: Racemase assays were performed in buffer containing 0.2 M Tris-HCl (squares), sodium acetate (triangles) and sodium phosphate (circles), 40 mM L-proline and 0.25 µM of purified rTcPRACA (closed symbols) and rTcPRACB (open symbols). After 30 min at 37° C., the reaction was stopped by heat inactivation and freezing. D. 39 kDa intracellular isoform was isolated from soluble (Ese) extracts of non-infective epimastigote forms of the parasite. Western-blots of serial dilutions of the soluble suspension was compared to known amounts of rTcPRACB protein and used for protein quantitation using Quantity One® software. Racemase assays were performed in sodium acetate buffer pH6, using 40 mM L-proline and the equivalent depicted amounts of 39 kDa (ng) contained in Ese extract.
Figure 2B:
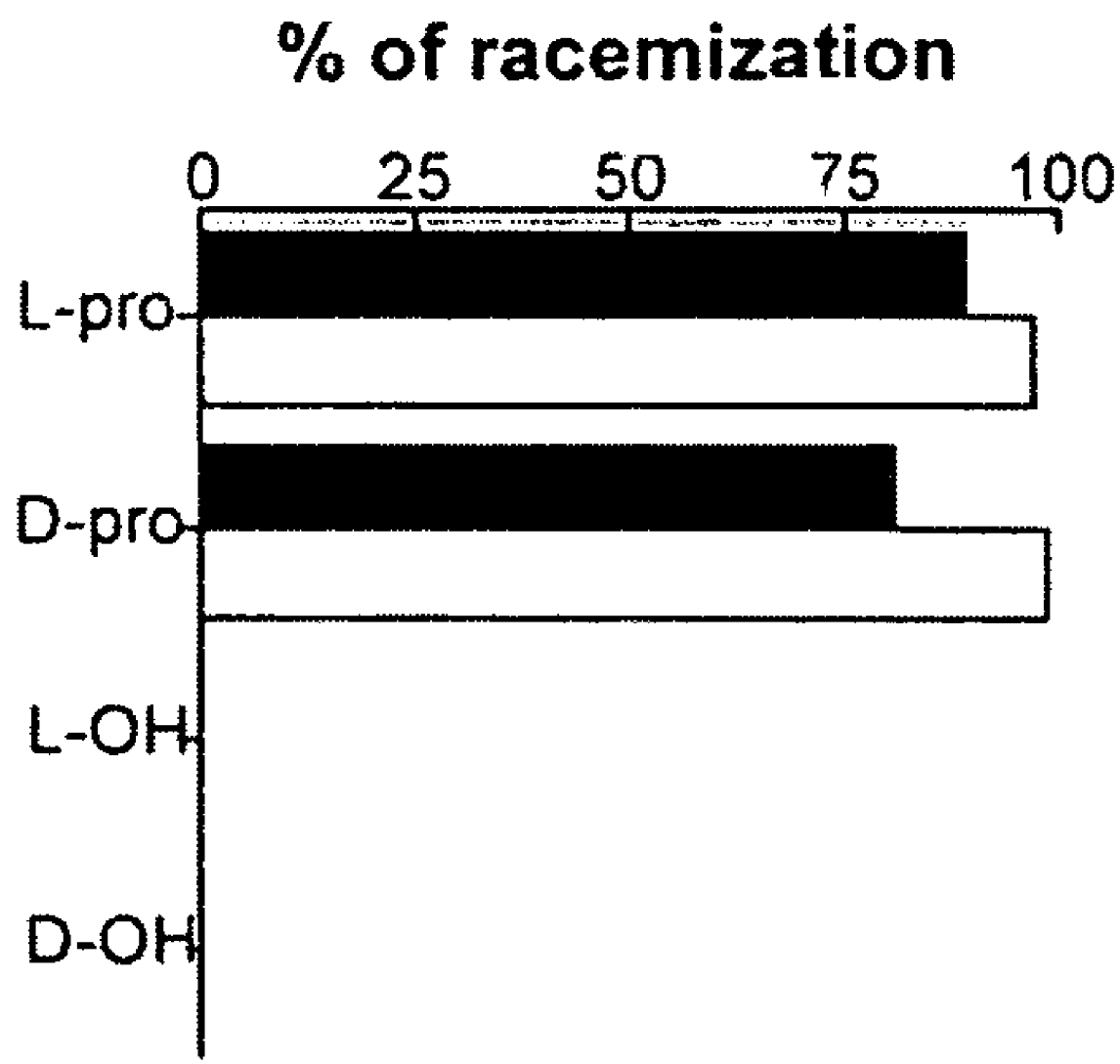
Figure 2C:
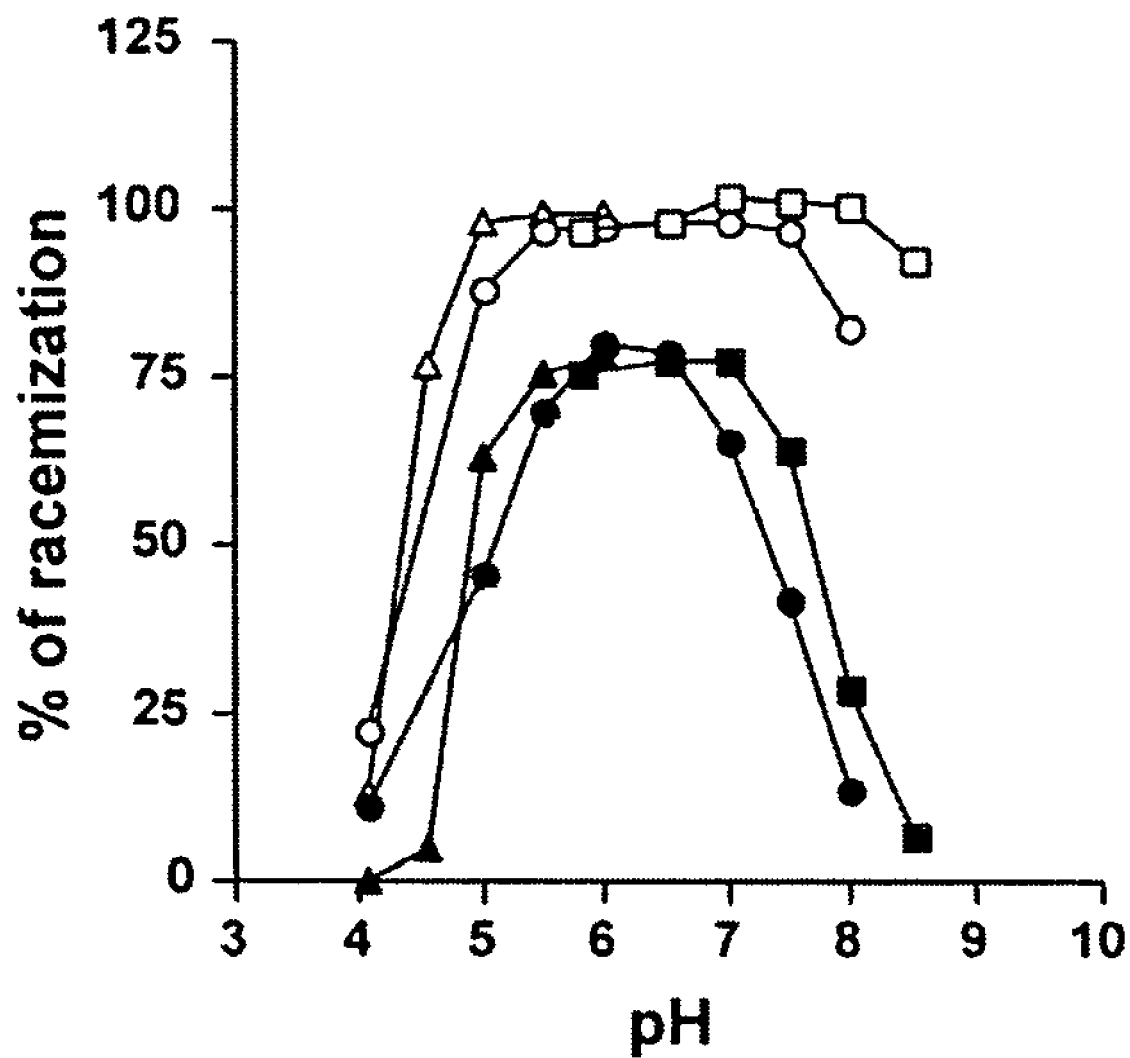
Figure 2D:
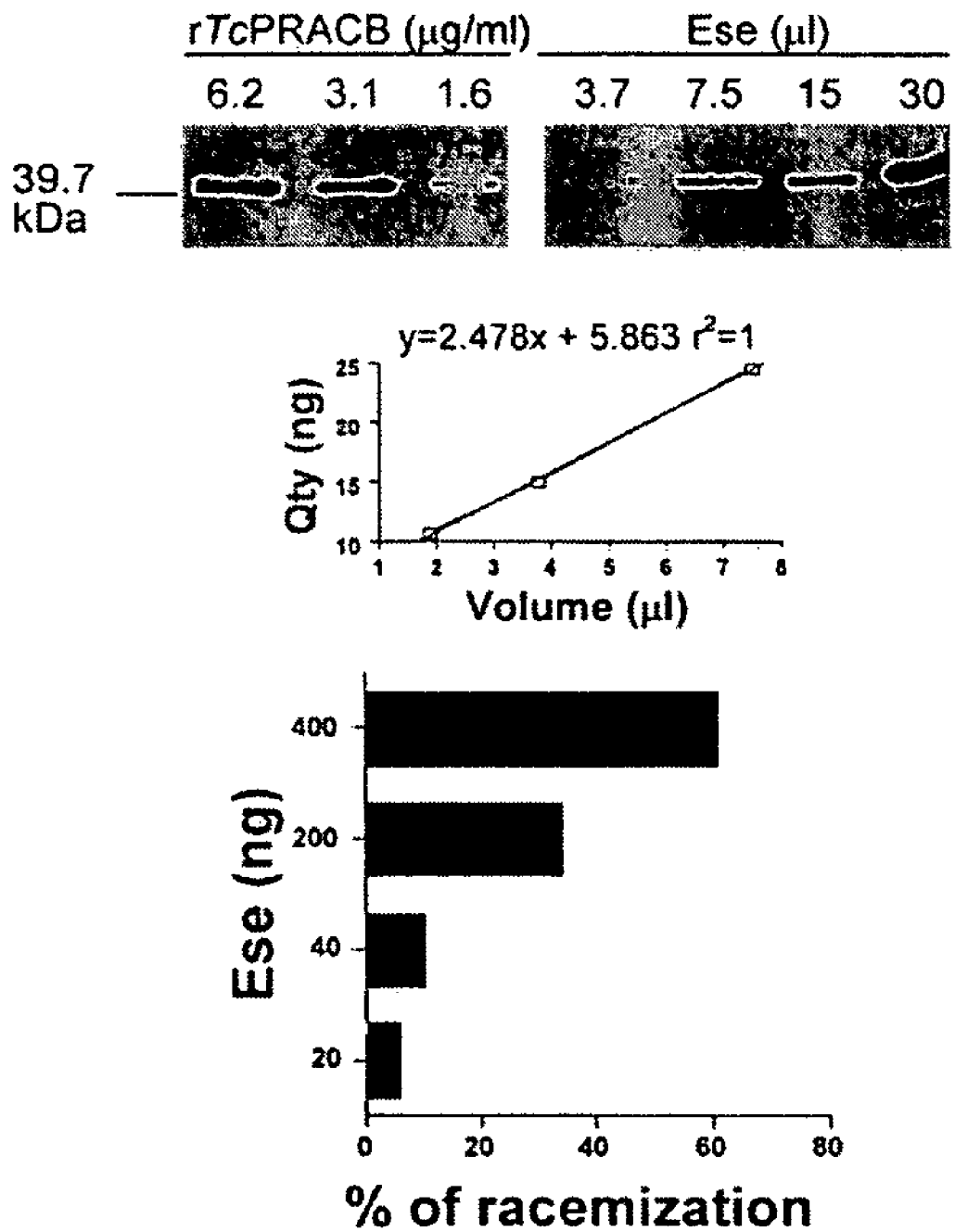

In order to verify if the TcPRACB gene could encode a functional proline racemase, both *T. cruzi* paralogues were expressed in *E. coli* to produce C-terminal His$_6$-tagged recombinant proteins. After purification by affinity chromatography on nickel-nitrilotriacetic acid agarose column, recombinant proteins were separated by SDS gel electrophoresis revealing single bands with the expected sizes of 45.8 and 40.1 kDa, respectively, for the rTcPRACA and rTcPRACB proteins (FIG. 2A). To determine whether rTcPRACB displays proline racemase enzymatic activity, biochemical assays were employed to measure the shift in optical rotation of L- and D-proline substrates, as described (13). As can be seen in FIG. 2B, rTcPRACB racemizes both L- and D-proline but not L-hydroxy-proline, like rTcPRACA. In a similar manner, rTcPRACB is a co-factor independent proline racemase as described for CsPR (11) and rTcPRACA (13) proline racemases. The rate of conversion of L- into D-proline was measured at various pH values using both recombinant enzymes. As illustrated in FIG. 2C, rTcPRACA activity clearly shows a pH dependency with an optimal activity from pH 5.5 to 7.0. In contrast, the optimum activity of rTcPRACB can be observed in a large pH spectrum varying from pH 4.5 to 8.5. These results revealed that translation of the open reading frame of both TcPRAC genes copies result in functional proline racemase isoforms. As previously described, Western blot analysis of non-infective epimastigote parasite extracts using antibodies raised against the 45 kDa secreted proline racemase had previously revealed a 39 kDa protein mostly in the soluble cellular fraction, only weakly in the cellular insoluble fraction and absent from culture medium (13). To demonstrate that the intracellular 39 kDa isoform of the protein was equally functional in vivo, soluble cellular extracts were obtained from 5×10$^8$ epimastigotes, non-infective parasites and the levels of 39 kDa soluble protein quantified by Western blot comparatively to known amounts of rTcPRACB enzyme. As can be observed in FIG. 2D, the intracellular isoform of the protein is indeed functional in vivo, since proline racemase enzymatic activity was displayed and levels of racemization were dependent on protein concentration. This discovery is useful for specific inhibitors reaching the intracellular compartment.

EXAMPLE 10

Functional Analysis and Kinetic Properties of Recombinant *T. cruzi* Proline Racemases Since the TcPRAC gene copies encode for secreted and non-secreted isoforms of proline racemase with distinct pH requirements for activity, our investigation was made to determine whether other biochemical properties differ between rTcPRACA and rTcPRACB proteins. Such differences might reflect the cellular localization of the protein during parasite differentiation and survival in the host. Both rTcPRACA and rTcPRACB enzyme activities are maximal at 37° C. and can be abolished by heating for 5 min at 80° C. However, the stability of the two recombinant enzymes differs considerably, when analyzed under different storage conditions. Thus, as shown in Table 1, purified rTcPRACB is highly stable, since its activity is maintained for at least 10 days at room temperature in 0.5 M imidazol buffer pH 8.0, as compared to rTcPRACA that loses 84% of its activity under such conditions. In contrast, most of the enzymatic activity of rTcPRACA is maintained at 4° C. (65%), compared to that of rTcPRACB (34%). Both enzymes can be preserved in 50% glycerol at −20° C., or diluted in sodium acetate buffer at pH 6.0, but under these storage conditions rTcPRACA activity is impaired. However, best preservation of both recombinant proline racemases was undoubtedly obtained when proteins were kept at −20° C. as ammonium sulfate precipitates. Preservation is important for a kit.

TABLE I

Stability of recombinant TcPRACA and TcPRACB proline racemases under different storage conditions
% of preservation of proline racemase activity

| Protein | Column | | | | NaOAc pH 6 | $(NH_4)_2SO_4$ | |
|---|---|---|---|---|---|---|---|
|  | CTRL | RT | +4° C. | Gly/−20° C. | 4° C. | 4° C. | −20° C. |
| rTcPRACA | 100.0 | 16.0 | 66.5 | 62.9 | 31.0 | 53.9 | 100.0 |
| rTcPRACB | 100.0 | 100.0 | 34.0 | 93.6 | 77.6 | 98.4 | 100.0 |

After purification on nickel-nitrilotriacetic acid agarose column, recombinant proteins were kept for 10 days in nickel column buffer (20 mM Tris/500 mM NaCl/500 mM imidazol, pH 8.0) at room temperature (RT) or at +4° C., or either diluted in 50% glycerol and maintained at −20° C. (Gly/−20° C.) or in optimum pH buffer (NaOAc, pH 6.0) at 4° C. Recombinant enzymes were precipitated in $(NH4)_2SO_4$ and kept in solution at 4° C. or pellet dried at −20° C. Racemase assays were performed for 30 min at 37° C. Percent of preservation was determined polarimetrically using 0.25 μM of either purified rTcPRACA or rTcPRACB enzymes and 40 mM of L-proline, as compared to results obtained with freshly purified proteins (CTRL). These results are representative of at least two independent experiments.

Figure 3A:
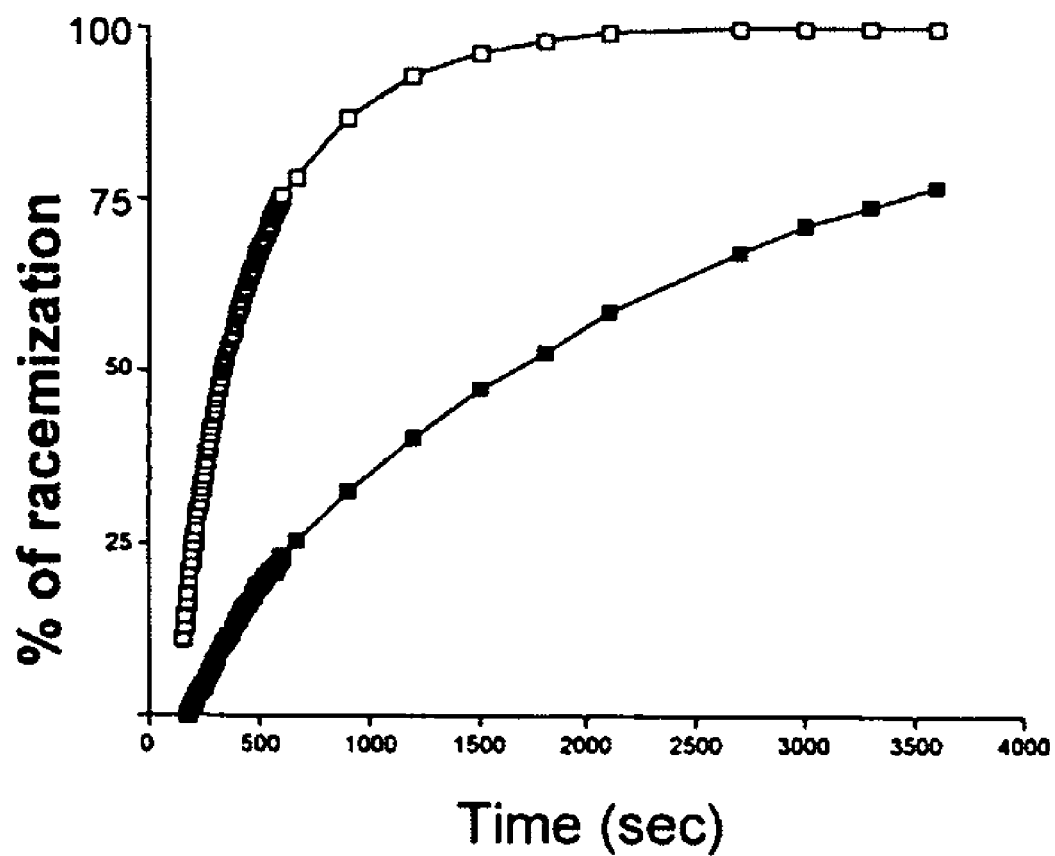
FIG. 3: Kinetic parameters of L-proline racemization catalyzed by rTcPRACA and rTcPRACB proline racemase isoforms. The progress of racemization reaction was monitored polarimetrically, as previously described (13). A. The determination of the linear part of the curve was performed at 37° C. in medium containing 0.2 M sodium acetate, pH 6.0; 0.25 µM purified enzyme and 40 mM L-proline. rTcPRACA reactions are represented by black squares and rTcPRACB reactions by white squares. B. Initial rate of racemase activity was assayed at 37° C. in medium containing 0.2 M sodium acetate, pH 6.0, 0.125 µM of rTcPRACA (solid squares) or rTcPRACB (open squares) purified enzymes and different concentrations of L-proline. Lineweaver-Burk double reciprocal plots were used to determine values for $K_M$ and $V_{max}$ where 1/V is plotted in function of 1/[S] and the slope of the curve represents $K_M/V_{max}$. Values obtained were confirmed by using the Kaleïdagraph® program and Michaelis-Menten equation. The values are representative of six experiments with different enzyme preparations. C. Double reciprocal plot kinetics of 0.125 µM rTcPRACA proline racemase isoform in the presence (open) squares or absence (solid) squares of 6.7 µM PAC competitive inhibitor in function of L-proline concentration. For comparison: $K_M$ reported for the proline racemase of *C. sticklandii* was 2.3 mM; kinetic assays using the native protein obtained from a soluble epimastigote fraction revealed a $K_M$ of 10.7 mM and a $K_i$ of 1.15 µM.
Figure 3B:
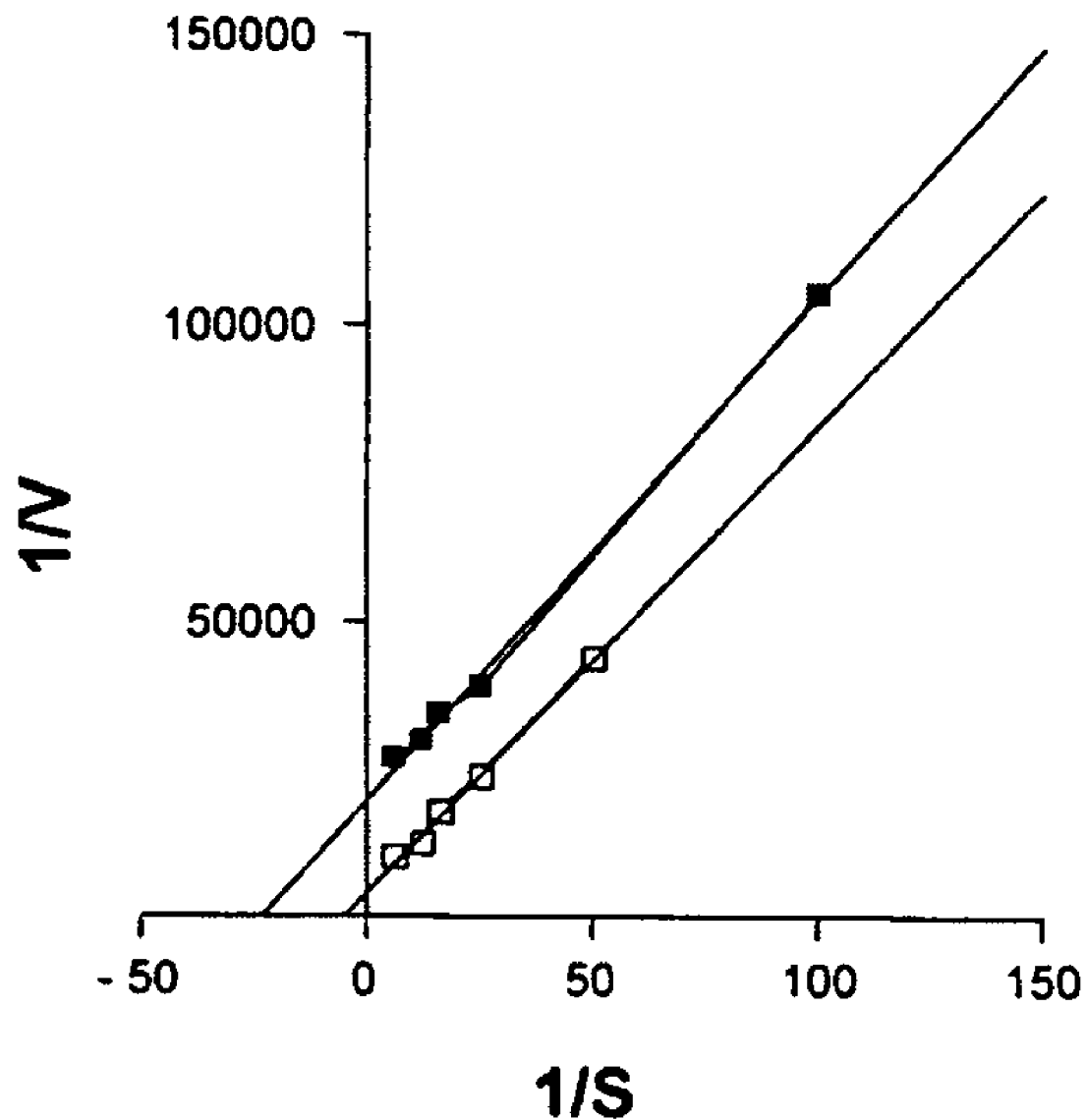
Figure 3C:
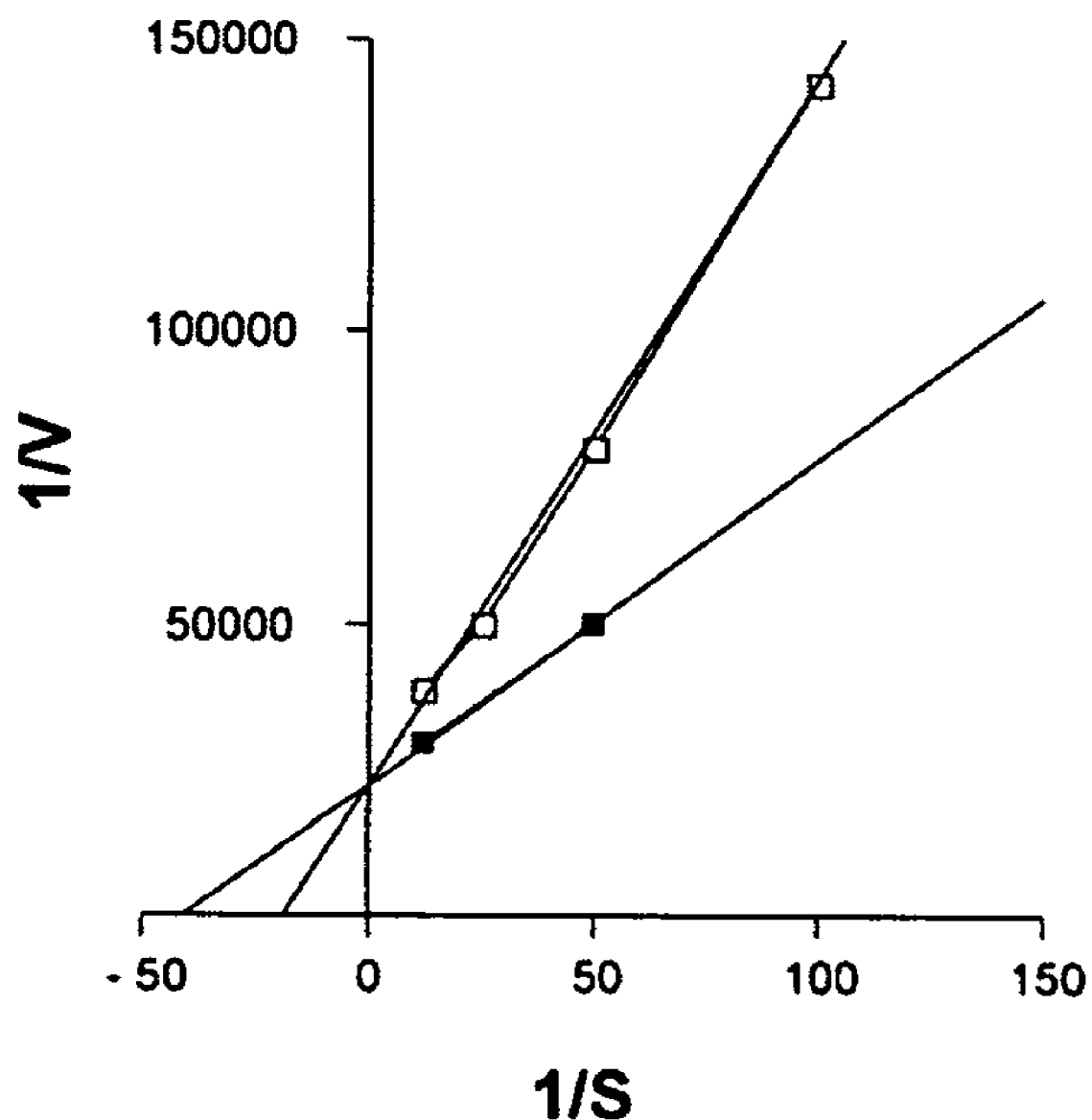

Both recombinant enzymes exhibited Michaelis-Menten kinetics (FIG. 3A) and rTcPRACB had a higher activity than rTcPRACA. Indeed, as can be observed in FIG. 3B, analysis of L>D conversion of serial dilutions of L-proline catalyzed by a constant amount of each enzyme showed that rTcPRACB enzyme ($K_M$ of 75 mM and $V_{max}$ of $2 \times 10^{-4}$ mol.sec$^{-1}$) has a higher velocity as compared to rTcPRACA ($K_M$ of 29 mM and $V_{max}$ of $5.3 \times 10^{-5}$ mol.sec$^{-1}$). In order to determine the $K_i$ values for pyrrole-2-carboxylic acid (PAC), the specific and competitive inhibitor of CsPR (16), assays were performed with both recombinant proteins. These assays revealed that PAC is comparably effective as inhibitor of rTcPRACA (FIG. 3C) and rTcPRACB, and $K_i$ values obtained were, respectively, 5.7 μM and 3.6 μM. The difference in $K_i$ values reflects almost perfectly the difference in $K_M$ values reported for both enzymes, which are similar to that of the native protein. These $K_i$ values indicate that the affinity of PAC inhibitor is higher for rTcPRACA and rTcPRACB than for CsPR ($K_i$ of 18 μM). The $K_M$ and $K_i$ values are important for an inhibitor.

EXAMPLE 11

Requirement of a Dimeric Structure for Proline Racemase Activity

Figure 4:
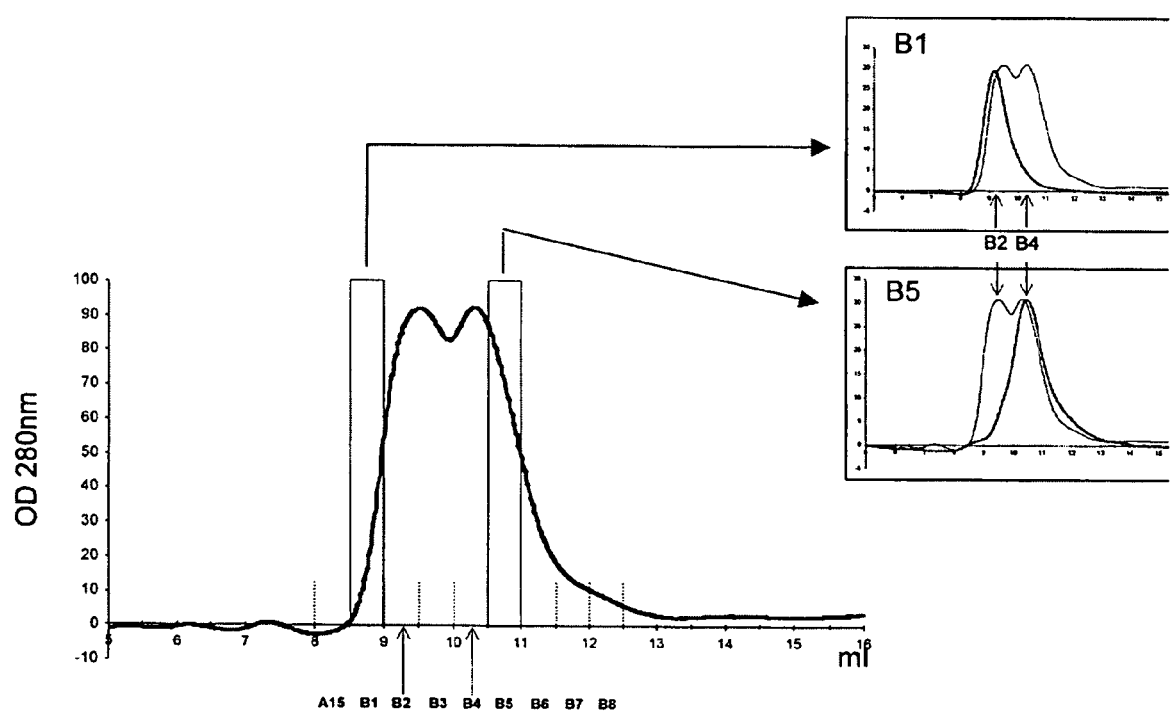
FIG. 4: Size exclusion chromatography of rTcPRACA protein using a Superdex 75 column. Fractions were eluted by HPLC at pH 6.0, B2 and B4 peaks correspond to rTcPRACA dimer and monomer species respectively. B1 and B5 eluted fractions were reloaded into the column (bold, see inserts) using the same conditions and compared to previous elution profile (not bold).

When rTcPRACA was submitted to size exclusion chromatography on a Superdex 75 column at pH 6.0, two peaks of protein were eluted, respectively, around 80 kDa (B2 fraction) and 43 kDa (B4 fraction), presumably corresponding to dimeric and monomeric forms of the enzyme (FIG. 4). Western blot analysis of whole T. cruzi epimastigote extracts using non-denaturing PAGE had previously indicated a molecular mass of 80 kDa for the native protein while a 45 kDa band was obtained by SDS-PAGE (13). In order to eliminate cross-contamination, B1 and B5 fractions, eluted, respectively, at the start and at the end of the predicted dimer (B2) or monomer (B4) peaks, were reloaded on the column and the profiles obtained (see FIG. 4 inserts) confirmed the purity of the fractions. Enzyme activity resides in the 80 kDa peak, but not in the 43 kDa peak (Table II). These results corroborated that two subunits of the protein are necessary for racemase activity. At neutral pH (7.4 or above), the rTcPRACA gives rise to high molecular weight aggregates which are not observed with rTcPRACB, consistently with its broader optimal pH spectrum. The enzyme should be in optimal pH conditions for a kit buffer, for example.

TABLE II

Racemase activity of recombinant TcPRACA fractions after size exclusion chromatography

|  | Fractions | | | | | | | |
|---|---|---|---|---|---|---|---|---|
|  | A15 | B1 | B2 | B3 | B4 | B5 | B6 | B7 |
| % racemization | 1.3 | 35.5 | 62.9 | 42.8 | 0.7 | 0 | 0 | 0 |

After elution from Superdex 75 column, 20 μl of each peak (A15 to B7, see FIG. 4) corresponding to 1 μg of protein were incubated 1 h at 37° C. with 40 mM of L-proline in 0.2 M NaOAc, pH 6.0. Optical rotation was measured and % of racemization was determined as described in Example 5.

EXAMPLE 11

Figure 12:
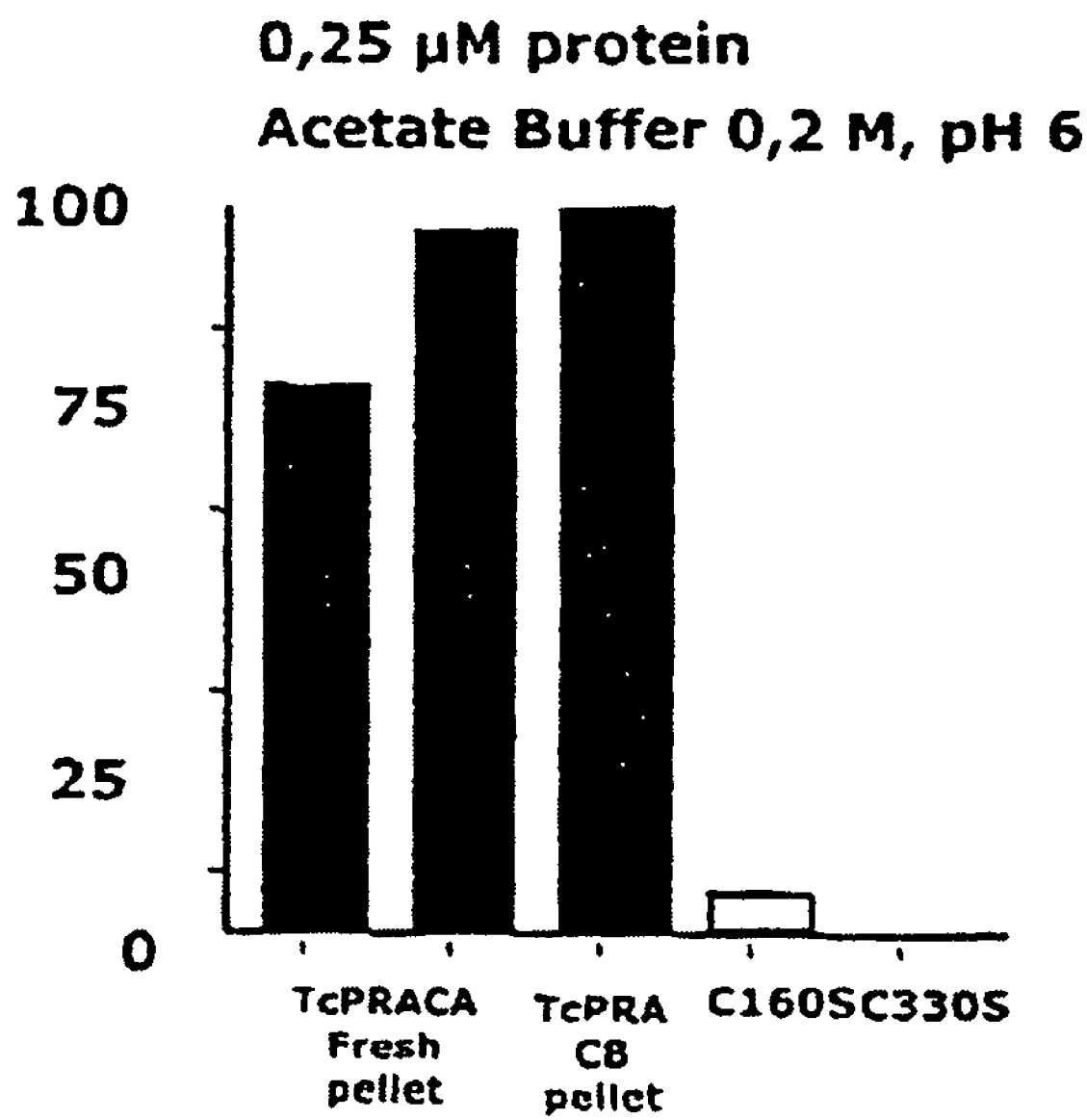
FIG. 12 shows the loss of the enzymatic activity of proline racemase after mutagenesis of the residue $Cys^{160}$ or the residue $Cys^{330}$. The loss of the enzymatic activity of proline racemase after mutagenesis of the Cys160 or the Cys330 residues is shown in the figure below. The results confirm that both residues of a same homodimer unit are implicated in the enzymatic active site of the proline racemase. Furthermore, these results challenge the previous proposed mechanism of proline racemization predicted for the protobacterium *Clostridium sticklundii*, as TcPRAC possesses two active sites per homodimer.

Abrogation of Proline Racemase Activity by Mutation of Cys$^{330}$ and Alternately Cys$^{160}$ of the Catalytic Site C. sticklandii proline racemase is described as a homodimeric enzyme with subunits of 38 kDa and a single proline binding site for every two subunits, where two cysteines at position 256 might play a crucial role in catalysis by the transfer of protons from and to the bound substrate (12). It has previously been shown that mitogenic properties of the T. cruzi proline racemase are dependent on the integrity of the enzyme active site, as inhibition of B-cell proliferation is obtained by substrate competition and specific use of analogues (PAC) resembling the structure assumed by the substrate proline in its transition state (16). To verify the potential role of the cysteine residues at the active site of the T. cruzi proline racemase, Cys$^{330}$ and alternately Cys$^{160}$ were replaced by a serine residue through site specific mutation of TcPRACA. The choice of serine as the substituting amino acid was made to avoid further major disturbances on three dimensional structure of the protein (see strategy in FIG. 5 above). After confirmation of the single codon mutation through sequencing of the construct, the $^{C330S}$ or $C^{160S}$ rTcPRACA mutant proline racemase was expressed in E. coli and purified in the same manner as wild type rTcPRACA. Then used were $^{C330S}$ or $C^{160S}$ rTcPRACA in racemization assays to verify the effects of the mutation on the enzymatic activity of the protein. As can be observed in Table III (and in FIG. 12) a total loss of proline racemase activity is observed as compared to the wild type enzyme, establishing that proton transfer during proline racemization is specifically dependent on the presence of the cysteine residue in the active site.

TABLE III

Loss of racemase enzymatic activity in the site direct $^{C330S}$rTcPRACA

| Data set | rTcPRACA | | | | $^{C330S}$rTcPRACA | | | |
|---|---|---|---|---|---|---|---|---|
| Time (min) | 0 | 10 | 30 | 60 | 0 | 10 | 30 | 60 |
| Optical rotation | −0.385 | −0.300 | −0.162 | −0.088 | −0.385 | −0.382 | −0.391 | −0.387 |
| % racemization | 0 | 22 | 58 | 77 | 0 | 0 | 0 | 0 |

After purification, 5 μg of rTcPRACA or $^{C330S}$rTcPRACA were incubated at 37° C. with 40 mM of L-proline in NaOAc buffer, pH 6.0. Optical rotation was measured at different times and % of racemization was determined as described in Example 5.

EXAMPLE 12

Figure 7:
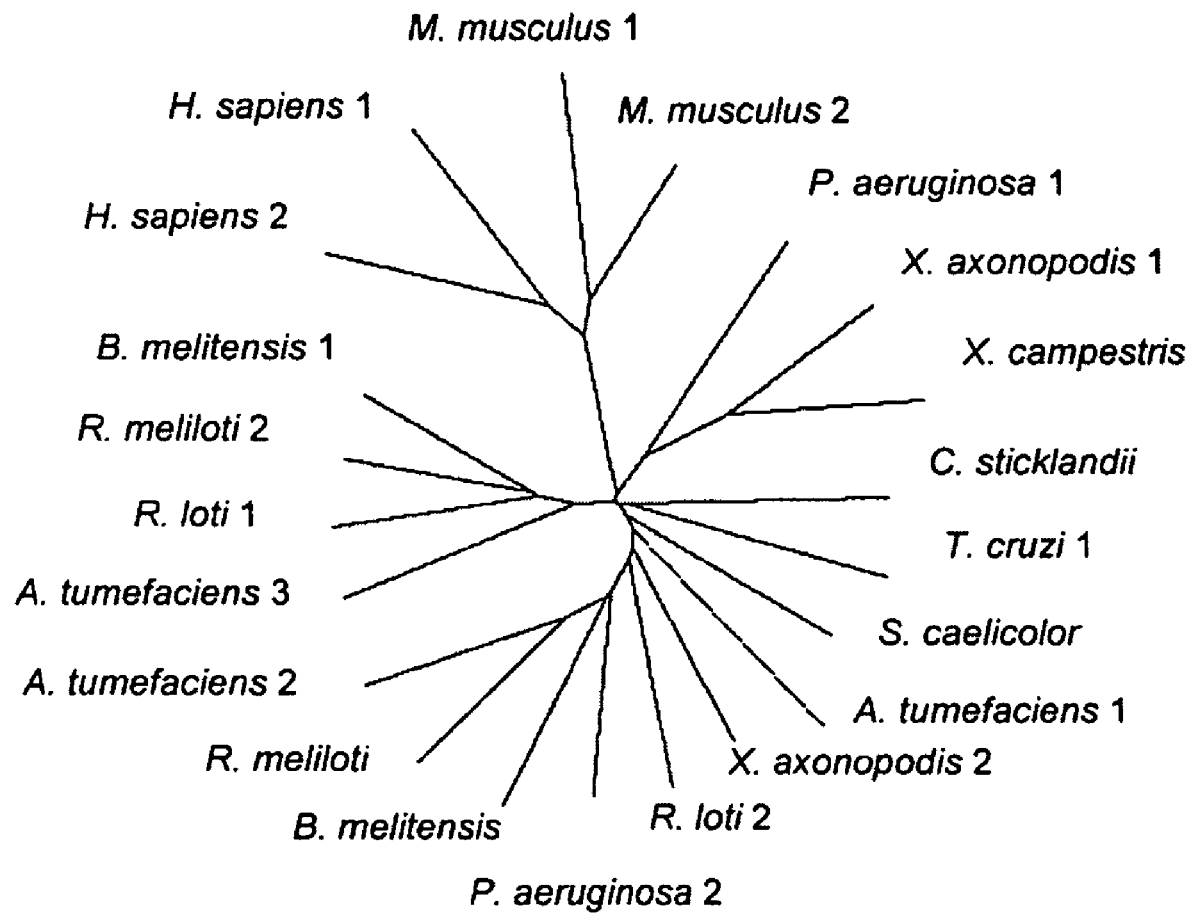
FIG. 7: Cladogram of protein sequences obtained by T-coffee alignment radial tree. See Table IV for SWISS-PROT protein accession numbers.

Proline Racemase Protein Signatures and Putative Proline Racemases in Sequence Databases The conservation of critical residues between parasite and bacterial proline racemases prompted a search for similarities between TcPRAC and other protein sequences in SWISS-PROT and TrEMBL databases. Twenty one protein sequences yielded significant homologies, from 11 organisms, such as several proteobacteria of the alpha subdivision (*Agrobacterium*, *Brucella*, *Rhizobium*) and gamma subdivision (*Xanthomonas* and *Pseudomonas*), as well as of the fermicutes (*Streptomyces* and *Clostridium*). Within the eukaryote, besides in *T. cruzi*, homologous genes were detected in the human and mouse genomes, where predicted proteins show overall similarities with proline racemase. Except for *Clostridium sticklandii* and *Xantomonas campestri*, each other organism encodes 2 paralogues, and *Agrobacterium tumefaciens* contains 3 genes. The multiple alignment also allowed for the definition of three signatures of proline racemase, which are described here in PROSITE format. As can be seen in Table IV, when using a minimal motif of proline racemase protein (M I), [IVL][GD]XHXXG[ENM]XX[RD]X[VI]XXG (SEQ ID NO: 23), located immediately after the start codon at position 79, the inventors obtained 9 hits. A second motif (M II), consisting of [NSM][VA][EP][AS][FY]X(13,14)[GK]X[IVL]XXD[IV][AS][YWF]GGX[FWY] (SEQ ID NO: 2), starting at position 218, gave 14 hits; however, the first or the second half of this motif is not sufficiently stringent to be restrictive for putative proline racemases, but gives hits for different protein families. A third motif (M III), from positions 326 to 339, namely DRSPXGX[GA]XX-AXXA (SEQ ID NO: 24), was considered as a minimal pattern. Note that in position 330, the cysteine of the active site was replaced by an X. As shown in Table IV, this minimal pattern yields all 21 hits. Curiously, both genes in human as well as in mouse encode threonine instead of cysteine at the X position in motif III, while in *Brucella*, *Rhizobium* and *Agrobacterium* species each encode one protein with C and one with T in this position. One cannot hypothesize the implications of this substitution for the functionality of these putative proteins. If the residue at position 330 is maintained as a cysteine in motif III, a reduced number of 12 hits from 9 organisms is thus obtained, which can probably be considered as true proline racemases. The alignment of the 21 protein sequences and derived cladogram are shown in FIG. 6 and FIG. 7, respectively, the three boxes depicted correspond to motifs I, II and III described here above. This invention thus shows that DRSPCGXGXXAXXA (SEQ ID NO: 4) is the minimal signature for proline racemases. Blast searches against unfinished genomes yielded, at present, an additional 13 predicted protein sequences from 8 organisms, with high similarity to proline racemases, all containing motif III. Organisms are *Clostridium difficile*, *C. botulinum*, *Bacillus anthracis*, *Brucella suis*, *Pseudomonas putida*, *Rhodobacter sphaeroides*, *Burkholderia pseudomallei*, *B. mallei*, and the fungus *Aspergillus fumigatus*. These results indicate that proline racemases might be quite widespread.

TABLE IV

SWISS-PROT and TrEMBL databases screening using PROSITE motifs

| Organism | Seq | Access. nb | M I | M II | M III | M III* |
|---|---|---|---|---|---|---|
| Agrobacterium tumefaciens | 1 | Q8UIA0 | + | + | + | + |
| Agrobacterium tumefaciens | 2 | Q8U6X2 | − | − | + | − |
| Agrobacterium tumefaciens | 3 | Q8U8Y5 | − | − | + | − |
| Brucella melitensis | 1 | QBYJ29 | − | + | + | + |
| Brucella melitensis | 2 | Q8YFD6 | + | + | + | − |
| Clostridium stickilandii | | Q9L4Q3 | − | + | + | + |
| Homo sapiens | 1 | Q96EM0 | + | + | + | − |
| Homo sapiens | 2 | Q96LJ5 | + | + | + | − |
| Mus musculus | 1 | Q9CXA2 | + | + | + | − |
| Mus musculus | 2 | Q99KB5 | + | + | + | − |
| Pseudomonas aeruginosa | 1 | Q9I476 | − | + | + | + |
| Pseudomonas aeruginosa | 2 | Q9I489 | − | − | + | + |
| Rhizobium loti | 1 | Q98F20 | − | + | + | + |
| Rhizobium loti | 2 | Q988B5 | + | + | + | − |
| Rhizobium meliloti | 1 | Q92WR9 | − | − | + | − |
| Rhizobium meliloti | 2 | Q92WSI | − | + | + | − |
| Streptomyces coelicolor | | Q93RX9 | + | − | + | + |
| Trypanosoma cruzi | 1 | Q9NCP4 | + | + | + | + |
| Trypanosoma cruzi | 2 | Q868H8 | + | + | + | + |
| Xanthomonas axonopodis | 1 | Q8PJI1 | − | + | + | + |
| Xanthomonas axonopodis | 2 | Q8PKE4 | − | − | + | + |

TABLE IV-continued

SWISS-PROT and TrEMBL databases screening using PROSITE motifs

| Organism | Seq | Access. nb | M I | M II | M III | M III* |
|---|---|---|---|---|---|---|
| Xanthomonas campestris | | Q8P833 | − | + | + | + |
| Bacillus anthracis (Ames) | 1 | Q81UH1 | + | − | + | + |
| Bacillus anthracis (Ames) | 2 | QB1PH1 | − | − | + | + |
| Bacillus cereus | 1 | Q81HBI | + | − | + | + |
| Bacillus cereus | 2 | Q81CD7 | − | − | + | + |
| Brucella suis | 1 | Q8FYSO | + | + | + | + |
| Brucella suis | 2 | Q8G213 | + | − | + | − |
| Chromobacterium violaceum | | Q7NU77 | + | + | + | + |
| Photorhabdus luminescens | | Q7N4S6 | + | + | + | + |
| Pseudomonas putida | | Q88NF3 | + | + | + | + |
| Rhodopirella baltica | | Q7UWF3 | − | − | + | + |
| Streptomyces avermitilis | | Q82MDO | + | − | + | + |
| Vibrio parahaemolyticus | | Q87Q20 | + | + | + | + |

SWISS-PROT and TrEMBL databases were screened using motifs I to III (M I, M II and M III). M I corresponds to [IVL][GD]XHXXG[ENM]XX[RD]X[VI]XXG (SEQ ID NO: 23), M II to of [NSM][VA][EP][AS][FY]X (13, 14)[GK]X[IVL]XXD[IV][AS][YWF]GGX[FWY] (SEQ ID NO: 2) M III to DRSPXGXGXXAXXA (SEQ ID NO: 3) and M III* to DRSPCGXGXXAXXA (SEQ ID NO: 4) Access. nb, SWISS-PROT accession number of the sequence; seq, sequence number according to FIG. 6; + and −, presence or absence respectively of hit using the corresponding motif.

Finally, Table V summarizes the genes in which the proline racemase signature has been identified and the sequences including both crucial residues $Cys^{330}$ and $Cys^{160}$ of the catalytic site are present.

TABLE V

Results of screening using nucleotide or peptide sequence of TcPRACA

| Organism | Accession number | Database | M I | M II | M III | M III* $Cys^{330}$ | MCGH $Cys^{160}$ | common sequence EPRGH (SEQ ID NO: 25) |
|---|---|---|---|---|---|---|---|---|
| Aspergillus fumigatus | Af0787f05.p1c | TIGR | + | − | + | − | + | + |
| Aspergillus fumigatus | TIGR 5085 | TIGR | + | + | + | + | ? | + |
| Bacillus anthracis str. Ames | AE017027 | EMBL | + | + | + | + | + | + |
| Bacillus anthracis str. Ames (minus strand) | AE017033 | EMBL | + | + | + | + | + | + |
| Bacillus anthracis | TIGR 1392 | TIGR | + | + | + | + | + | + |
| Bacillus cereus ATCC14579 (minus strand) | AE017007 | EMBL | + | + | + | + | + | + |
| Brucella suis 1330 (minus strand) | AE014469 | EMBL | + | + | + | + | + | + |
| Brucella suis | TIGR 29461 | TIGR | + | + | + | + | + | + |
| Burkholderia mallei | contig:33162:b_mallei | TIGR | + | + | + | + | + | EPRGSD (SEQ ID NO: 26) |
| Burkholderia mallei | TIGR 13373 | TIGR | + | ? | + | + | + | EPRGSD (SEQ ID NO: 26) |
| Burkholderia pseudomallei | SANGER 28450 | Sanger | + | ? | + | + | + | EPRGSD (SEQ ID NO: 26) |
| Clostridium botulinum | Cbot12g05.q1c | Sanger | ? | + | + | + | + | + |
| Clostridium botulinum | SANGER 36826 | Sanger | + | + | + | + | + | + |
| Clostridium difficile | Clostridium difficile 630 | Sanger | ? | + | + | + | + | + |
| Clostridium difficile | SANGER 1496 | Sanger | + | + | + | + | + | + |
| Clostridium sticklandii | CST130879 | EMBL | + | + | + | + | + | + |
| Leishmania major | LM16BINcontig2054 | Sanger | ? | + | + | + | + | EPRGND (SEQ ID NO: 27) |
| Leishmania major | LM16W5b02.q1c | Sanger | ? | + | ? | ? | + | EPRGND (SEQ ID NO: 27) |
| Pseudomonas putida KT2440 | AE016778 | EMBL | + | + | + | + | + | EPRGND (SEQ ID NO: 27) |
| Pseudomonas putida KT2440 | TIGRpputida 13538 | TIGR | + | ? | + | + | + | EPRGND (SEQ ID NO: 27) |
| Rhodobacter sphaeroides | UTHSC 1063 | UTHSC | + | ? | − | − | + | + |
| Trypanosoma brucei | TbKIX28b06.qlc | Sanger | ? | + | ? | ? | + | + |
| Trypanosoma brucei | TbKIX28b06.plc | Sanger | ? | + | ? | ? | + | + |
| Trypanosoma vivax | Tviv655d02 | Sanger | + | + | + | + | ? | ? |
| Trypanosoma vivax | Tviv380d6 | Sanger | + | ? | ? | ? | + | + |

TABLE V-continued

Results of screening using nucleotide or peptide sequence of TcPRACA

| | | | Motifs | | | | | common |
|---|---|---|---|---|---|---|---|---|
| | | | | | | M III* | MCGH | sequence EPRGH |
| Organism | Accession number | Database | M I | M II | M III | $Cys^{330}$ | $Cys^{160}$ | (SEQ ID NO: 25) |
| *Trypanosoma congolense* | congo208e06 | Sanger | ? | + | + | + | ? | ? |
| *Vibrio parahaemolyticus* | AP005077 | EMBL | + | + | + | + | + | + |

Databases were screened using nucleotide or peptide sequences of TcPRACA. Motifs I to III (M I, M II and M III) were searched. M I corresponds to [IVL][GD]XHXXG[ENM]XX[RD]X[VI]XXG (SEQ ID NO: 23), M II to of [NSM][VA][EP][AS][FY]X(13, 14)[GK]X[IVL]XXD[IV][AS][YWF]GGX[FWY](SEQ ID NO: 2) M III to DRSPXGXGXXAXXA (SEQ ID NO: 3) and M III* to DRSPCGXGXXAXXA (SEQ ID NO: 4).Access. nbs, TIGR, EMBL or SANGER accession numbers of the sequence; + and −, presence or absence respectively of the corresponding motif.
Others,extremelyconservedregionsoutsidethemotifs,includingNMCGH(SEQIDNO:128)whichcontainsoneoftheactivesitecysteine.Sequences presented in annexe pages where the conserved regions of 2 Cysteine residues of the active site are squared, are presented in the table in bold with corresponding Accession numbers.

A variety of free D-amino acids can be found in different mammalian tissues in naturally occurring conditions. Some examples include the presence of D-serine in mammalian brain, peripheral and physiological fluids, or else D-asp that can be also detected in endocrine glands, testis, adrenals and pituitary gland. D-pro and D-leu levels are also very high in some brain regions, pineal and pituitary glands. Some reports attribute to D-amino acids a crucial role as neuromodulators (receptor-mediated neurotransmission), as is the case of D-ser, or as regulators of hormonal secretion, oncogeny and differentiation (i.e. D-asp). It is believed that the most probable origin of naturally occurring D-amino acids in mammalian tissues and fluids is the synthesis by direct racemization of free L-enantiomers present in situ. However, a part from the cloning of serine racemase genes from rat brain and human no other amino acid racemases were identified until now in man. Some others report that D-amino acids present in mammalian tissues are derived from nutrition and bacteria.

The increasing number of reports associating the presence of D-amino acids and pathological processes indicate that the alteration of their level in biological samples would be of some diagnostic value as, for instance, the identification of changes in free levels of D-asp and D-Ala in brain regions of individuals presenting Alzheimer. The amounts of D-asp seems to decrease in brain regions bearing neuropathological changes and is paralleled by an increase of D-ala. Overall, total amounts of D-amino acids increase in the brain of individuals presenting memory deficits in Alzheimer, as compared to normal brains, offering new insights towards the development of new simple methods of D-amino acid detection. In the same line, D-ser concentrations in the brain are altered in Parkinson disease and schizophrenia but other findings clearly associate significant higher concentrations of D-amino acids in plasma of patients with renal diseases or else in plasma of elderly people.

Previous results determined that the polyclonal B cell activation by parasite mitogens contributes to the mechanisms leading to parasite evasion and persistence in the mammalian host. It has also been demonstrated that TcPRAC is a potent B cell mitogen released by the infective forms of the parasite. The TcPRAC inhibition by pyrrole carboxylic acid induces a total loss of TcPRAC B cell mitogenic ability.

It has also been shown that the overexpression of TcPRACA and TcPRACB genes by mutant parasites are able to confer to these mutants a better invasion ability of host cells in vitro. This contrasts to the inability of parasites to survive if these TcPRAC genes are inactivated by genetic manipulation. In addition, the immunization of mice with sub-mitogenic doses of TcPRAC, or with appropriate TcPRAC-DNA vector vaccine preparations, was shown to trigger high levels of specific antibody responses directed to TcPRAC and high levels of immunoprotection against an infectious challenge with live *Trypanosoma cruzi*.

Altogether, these data suggest that TcPRAC enzyme isoforms are essential elements for parasite survival and fate and also support that parasite proline racemase is a good target for both vaccination and chemotherapy. In fact, the addition of pyrrole carboxylic acid at TcPRAC neutralizing doses to non-infected monkey cell cultures do not interfere with cellular growth. Besides, the utilization of a proline racemase inhibitor in humans would be a priori possible since the absence of the two critical active site cysteine residues (Cys 330 and Cys 160) for the PRAC enzyme activity has been observed in the single sequence that displays some peptide homologies with TcPRAC that was identified by blasting the Human Genome available data with the TcPRAC gene sequence.

Figure 8:
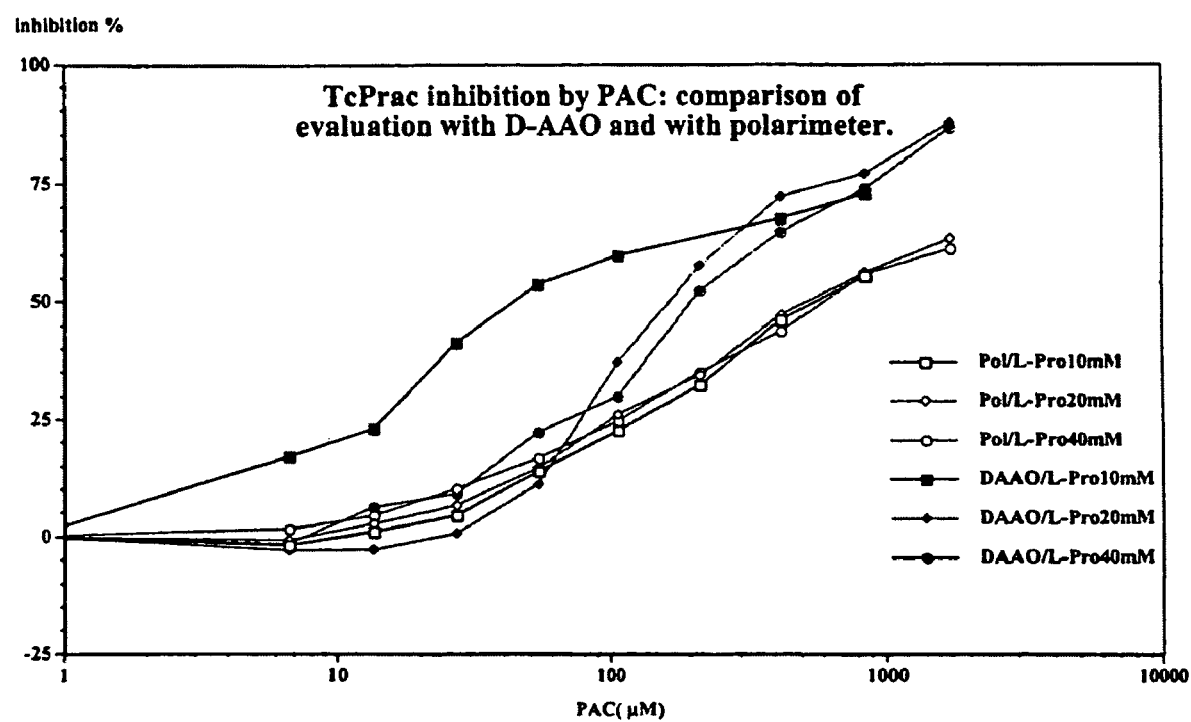
FIG. 8 shows the percent of racemisation inhibition of different L-proline concentrations (ranging from 10-40 mM) using the D-AAO (D-AA0/L-) microtest as compared to conventional detection using a polarimeter (Pol/L-).

As observed by data mining using TcPRAC gene sequences, it has been possible to identify putative proline racemases in other microrganisms of medical and agricultural interest. As can be seen in FIG. 8, the presence of MI, MII and most particularly Mil stringent motif (the signature for proline racemases) indicates the potentiality of those proteins to be functional proline racemases. On the one hand, it can be observed that critical residues necessary for the enzyme activity are displayed in those sequences and, on the other hand, that the open reading frames (ORF) are highly homologous to the ORF of the parasite PRAC.

In order to search for putative molecules that could be used as inhibitors of TcPRAC, or other proline racemases, it would be necessary to develop a microtest able to specifically reveal the inhibition of proline racemization performed by TcPRAC and consequently the blockage of a given proline stereoisomer generation. For instance, this could be done by analysing the ability of any potential inhibitory molecule to hinder the generation of D-proline in a reaction where L-proline is submitted to TcPRAC enzymatic activity.

At present, the available analyses to detect D- (or L-) amino acids are very challenging and methods to differentiate L-stereoisomers from D-stereoisomers are time-consuming, i.e.

gas chromatography, thin layer chromatography using chiral plates, high-performance capillary electrophoretic methods, HPLC, and some enzymatic methods. Some of those techniques also require the use of columns and/or heavy equipment, such as polarimeters or fluorescence detectors.

With the aim of developing a simple test that is useful to rapidly screen putative inhibitors of TcPRAC, TcPRAC constructs allowing for the production of high amounts of the recombinant active enzyme were used together with the knowledge of a specific inhibitor of proline racemases (pyrrole carboxylic acid, PAC) to develop a medium/high throughput microplate test that can be used to easily screen a high number of inhibitor candidates (i.e. 100-1000). Such a test is based on colorimetric reactions that are certainly a simpler alternative to polarimetry and other time-consuming tests. Thus, the evaluation of light deviation of L- or D-proline enantiomers by a polarimeter to quantify the inhibition of proline racemization to test such an elevated number of molecules is impracticable, offers a low sensibility, and would require greater amounts of reagents as compared to a microplate test that would additionally be of an affordable price.

Accordingly, this invention is based on the detection of D-proline originated through racemization of L-proline by TcPRAC, in the presence or in the absence of known concentrations of PAC inhibitor as positive and negative controls of racemization, respectively. For that purpose, this invention utilizes another enzyme, D-amino acid oxidase (D-AAO), that has the ability to specifically oxidize D-amino acids in the presence of a donor/acceptor of electrons and yield hydrogen peroxide. The advantage of this strategy is that hydrogen peroxide can be classically quantified by peroxidase in a very sensitive reaction involving ortho-phenylenediamine, for example, ultimately offering a chromogenic reaction that is visualized by colorimetry at 490 nm.

Since D-amino acid oxidase reacts indiscriminately with any "D-amino acid", and not with their L-stereoisomers, such a test is not only helpful to identify proline racemase inhibitors, but also applicable, if slightly modified, to detect any alterations in levels of free D-aa in various fluids to make a diagnosis of some pathogenic processes.

I—Basics for a D-amino-acid Quantitative Test

The following method of the invention allows detection and quantitation of D-Amino acids. A first reaction involves a D-amino-oxidase. This enzyme specifically catalyses an oxidative deamination of D-amino-acids, together with a prosthetic group, either Flavin-Adenin-Dinucleotide (FAD) or Flavin-Mononuclotide (FMN), according to the origin of the Enzyme. (Obs. FAD if the enzyme comes from porcine kidney).

The general reaction is as follows:

In (1), the D-amino acid is deaminated and oxidized, releasing ammonia and the reduced prosthetic group. If the amino group is not a primary group, the amino group remains untouched and no ammonia is released.

In (2), the reduced prosthetic group reduces oxygen, and generates hydrogen peroxide.

Either a catalase or a peroxidase can decompose hydrogen peroxide.

A catalase activity is written as:

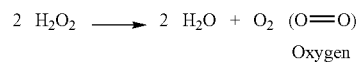

whereas a peroxidase activity is

wherein R' is any carbon chain

Thus, detection of hydrogen peroxide can be done with the use of catalase and a reagent sensitive to oxygen such as by destaining reduced methylene blue for instance with oxygen or with the use of peroxidase with a change in color of the reagent indicated by:

II—Application of Such a Test for Evaluating the *T. Cruzi* Racemase Activity and the Inhibition of this Racemase.

II-1—Test for Racemase Activity

The *T. cruzi* racemase activity converts reversibly L-Pro into D-Pro. Since these two forms can induce polarized light deviation, this conversion can be measured by optical polarized light deviation. But the presence of the D-form allows also the use of D-amino-acid oxidase in order to assess the amount of D-Proline in racemase kinetics. In this test the following reactions are involved:

1) Proline-Racemase activity.

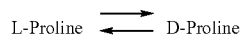

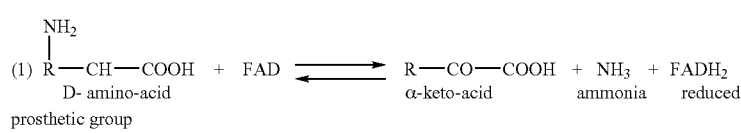

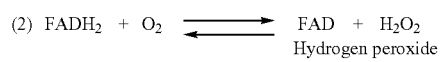

-continued

2) D-amino-acid oxidase (1) D-Proline + FAD ⇌ 1-Pyrroline2-carboxylic acid + FADH$_2$ (2) FADH$_2$ + O$_2$ ⇌ FAD + H$_2$O$_2$ 3) Detection of hydrogen peroxide with peroxidase H$_2$O$_2$ + chromogenic reagent ⇌ reduced chromogenic reagent + H$_2$O
(no color)                        (colored)

(Obs: There is no ammonia formed in the case of Proline, because the nitrogen of Proline is involved in a secondary amine.)

The chromogenic reagent can be, for example, orthophenylenediamine (OPD), or 3,3',5,5' tetramethyl benzidine (TMB), or 5-aminosalicylic acid (ASA).

These reactions can be carried out using the following exemplary, but preferred, materials and methods.

II-1-1—Materials

| Materials | Comments |
|---|---|
| Proline-racemase (TcPRAC) (1 mg/ml Stock) | |
| L-Proline, Sigma, Ref. P-0380 (1 M Stock) | An equimolar of D-and L-Proline is made by |
| D-Proline, Aldrich, ref. 85 891-9 (1 M Stock) | mixing equal volumes of 2 M D-Proline with 2 M L-Proline |
| Orthophenylenediamine (OPD) Sigma refP-8287 lot 119H8200 | 10 mg tablets. Extemporaneously used as a 20 mg/ml stock solution in water. |
| D-AAO from swine kidney (Sigma) ref. A-5222 lot 102K1287 | Powder dissolved into 1 ml Buffer* + 1 ml 100% glycerol. The resulting activity is 50 U/ml. Stored at −20° C. |
| Horse radish peroxidase (HRP) Sigma ref P8375 lot 69F95002 | Powder dissolved into 2, 5 ml Buffer* + 2, 5 ml 100% glycerol. The resulting activity is 5042 U/ml. Stored at −20° C. |
| Sodium acetate 0.2 M Ph6.0 | |
| Flavine-adenine-dinucleotide (FAD) (Sigma) ref. F-6625 | Stock solution of $10^{-1}$ M in water. Stored at −20° C. Used as a $10^{-3}$ M sub-stock solution. |
| Sodium pyrophosphate (Pop) 0.235 M | Not soluble at a higher concentration. Must be stored at 4° C. and gently heated before use in order to solubilize crystals which may occur. |
| Buffer* = 10 ml of 0.2 M sodium acetate buffer pH6.0 + 680 µl 0.235 M Pop | The final pH is 8.3. |
| Microplates (96 wells) | With adhesive coverlid |
| ELISA reader for microplates | With a wavelength filter at 490 nm for OPD substrate. |

II-1-2—Methods

II-1-2.1—Racemisation in Microplates:

(1) The volumes are indicated for a single well, but duplicates are mandatory. Leave enough raws of the microplate empty for standard and controls to be used in further steps. Distribute the following volumes per well reactions:

a) without inhibitor (Vol=QS 81 µl)

| | | | | |
|---|---|---|---|---|
| TcPRAC 1 mg/ml | 2 µl | 2 µl | 2 µl | 2 µl |
| L-Proline 0.1 M | 32 µl | 16 µl | 8 µl | 4 µl |
| Proline Final concentration | (40 mM) | (20 mM) | (10 mM) | (5 mM) |
| Sodium acetate buffer 0.2 M pH6 | 47 µl | 63 µl | 71 µl | 75 µl | b) with inhibitor (Vol=QS 81 µl)

A range of concentrations between 5 mM and 1 mM can be planned for the inhibitor. It should be diluted in sodium acetate buffer 0.2 M pH 6.0. Hence, the volume of inhibitor is substracted from the volume of buffer added in order to reach a final volume of 81 µl. For instance, 50% inhibition of racemisation of 10 mM L-proline is obtained with 45 µM Pyrrole carboxylic acid (PAC, specific inhibitor of proline racemase), when 36.5 µl PAC+44.5 µl buffer are used (see results in FIG. 8).

Table VI is provided for 10 mM L-Proline as a substrate.

TABLE VI

| | | | | | | | | | | |
|---|---|---|---|---|---|---|---|---|---|---|
| TcPrac 1 mg/ml | 2 µl | 2 µl | 2 µl | 2 µl | 2 µl | 2 µl | 2 µl | 2 µl | 2 µl | 2 µl |
| L-Proline 0.1 M | 8 µl | 8 µl | 8 µl | 8 µl | 8 µl | 8 µl | 8 µl | 8 µl | 8 µl | 8 µl |
| PAC 0.1 mM/1 mM**/10 mM*** | 0 µl | 5.4 µl | 11 µl | 22 µl | 43 µl | 9 µl ** | 17 µl ** | 35 µl ** | 69 µl ** | 14 µl ** |
| Final concentration (µM) | 0 | 6.7 | 13.5 | 27 | 54 | 107 | 214 | 429 | 858 | 1715 |
| Sodium acetate buffer 0.2 M pH6 QS 81 µl | 71 µl | 65.6 µl | 60 µl | 49 µl | 28 µl | 62 µl | 54 µl | 36 µl | 2 µl | 57 µl |

(2) Cover the microplate with an adhesive coverlid and leave for 30 nm at 37° C.
(3) At the end of racemisation, 5.5 µl of 0.235M Pop are added in each reaction well of the microplate in order to shift pH from pH6.0 to pH 8.3.

II-1-2.1-2—Quantitation of Formed D-Proline: Standards and Controls.

(1) Prepare standard and controls:
Standard: An equimolar mixture of L- and D-Proline is used as a standard in a range from 0.05 mM to 50 mM (final concentration in the assay). It is used for assessing the amount of D-Proline formed after racemization. The standard range is made in microtubes, as follows:
In tube 1, mix Proline and buffer according to the described proportions.
Then, add 500 µl of the obtained mixture to 500 µl of buffer in next tube, and so on.

This mixture is kept in the ice until use.
(4) The quantitation reaction starts when 13 µl of D-AAO/HRP mix is added to the reaction well.
(5) The microplate is covered with an adhesive coverlid and it is left in the dark at 37° C. between 30 nm and 2 hours. The reaction can be monitored by eye whenever a color gradient matches the D-amino acid concentration of the standard dilutions.
(6) The microplate is read with a microplate spectrophotometer using a filter of at 490 nm.

EXAMPLE 13

D-AOO Microplate Test is More Sensitive than D-amino Acid Detection by Detection in Polarimeter In order to compare the D-Proline quantitation by polarimeter and by D-amino-oxidase/HRP a comparison was per-

| Tube # | 1 | 2 | 3 | 4 | 5 | 6 | 7 | 8 | 9 | 10 | 11 | 12 |
|---|---|---|---|---|---|---|---|---|---|---|---|---|
| L- & D-Pro 1M | 250 µl | 500 µl | 500 µl | 500 µl | ... | | | | | | | 0 |
| Final Concentration (mM) in assay | 50 | 25 | 12.5 | 6.25 | 3.125 | 1.56 | 0.78 | 0.39 | 0.19 | 0.097 | 0.049 | 0 |
| Buffer* | 750 µl | 500 µl | 500 µl | 500 µl | ... | | | | | | | 1 ml |

Negative control: is prepared in an other microtube, as follows:

| | |
|---|---|
| L-Proline (1 M) | 200 µl |
| Buffer* | 800 µl |
| Final concentration | 40 ml |

Blank = Buffer*.

(2) Dispense in the empty wells of the microplate (see step II-1-2.1):

| | |
|---|---|
| Buffer* | 67 µl |
| Standard dilutions or negative control | 20 µl |

Obs: For the blank dispense 87 µl of Buffer* only (3) Prepare a mixture containing the enzymes (D-AAO/HRP Mix), as follows:

The amounts are given for one well, provided that the final volume will be 100 µl with the racemase products or the substrate:

| | For 13 µl: |
|---|---|
| Buffer* | 6.5 µl |
| D-AAO 50 U/ml | 1.7 µl |
| OPD (20 mg/ml) | 2.5 µl |
| HRP 5000 U/ml | 0.75 µl |
| FAD $10^{-3}$ M (4.5 µl $10^{-1}$ M + 446 µl buffer) | 1.5 µl | formed between the two tests using different concentrations of L-proline and different concentrations of PAC, the specific inhibitor of proline racemases. FIG. 8 shows the percent of racemisation inhibition of different L-proline concentrations (ranging from 10-40 mM) using the D-AAO (D-AA0/L-) microtest as compared to conventional detection using a polarimeter (Pol/L-).

With the polarimeter, there seems to be no difference of PAC inhibition of TcPRAC with the three concentrations of L-Proline. Therefore, 50% inhibition is obtained with 1 mM PAC, whether 10 mM or 40 mM L-Proline is used. In contrast, when using D-AAO/HRP test, it can be seen that inhibition by PAC is somewhat higher with a low concentration of L-Proline (10 mM for example) than with an increased one (20 mM or 40 mM). Therefore, 50% inhibition is obtained:
with 50 µM PAC when 10 mM L-Proline is used,
with 170 µM PAC when 20 mM L-Proline is used and
with 220 µM PAC when 40 mM L-Proline is used.

In conclusion, D-AAO/HRP evaluation is more sensitive since it can discriminate PAC inhibition at a lower concentration than evaluation with the polarimeter. Furthermore, inhibition is logically conversely proportional to L-Proline concentration, which can be assessed with the D-AAO/HRP method, but not with the polarimeter measurement. Such a test is useful for the screening of new inhibitors of TcPRAC in a medium/high throughput test.

A preferred technological platform to perform the above test and to select appropriate inhibitors contains at least the following products:
L-Proline, D-Proline, a proline-racemase
A peroxidase, a substrate of a peroxidase
A D-amino-acid oxidase
And optionally a battery of potential inhibitory molecules.

EXAMPLE 14

L-Proline Inhibits D-amino-oxidase Activity

Figure 9:
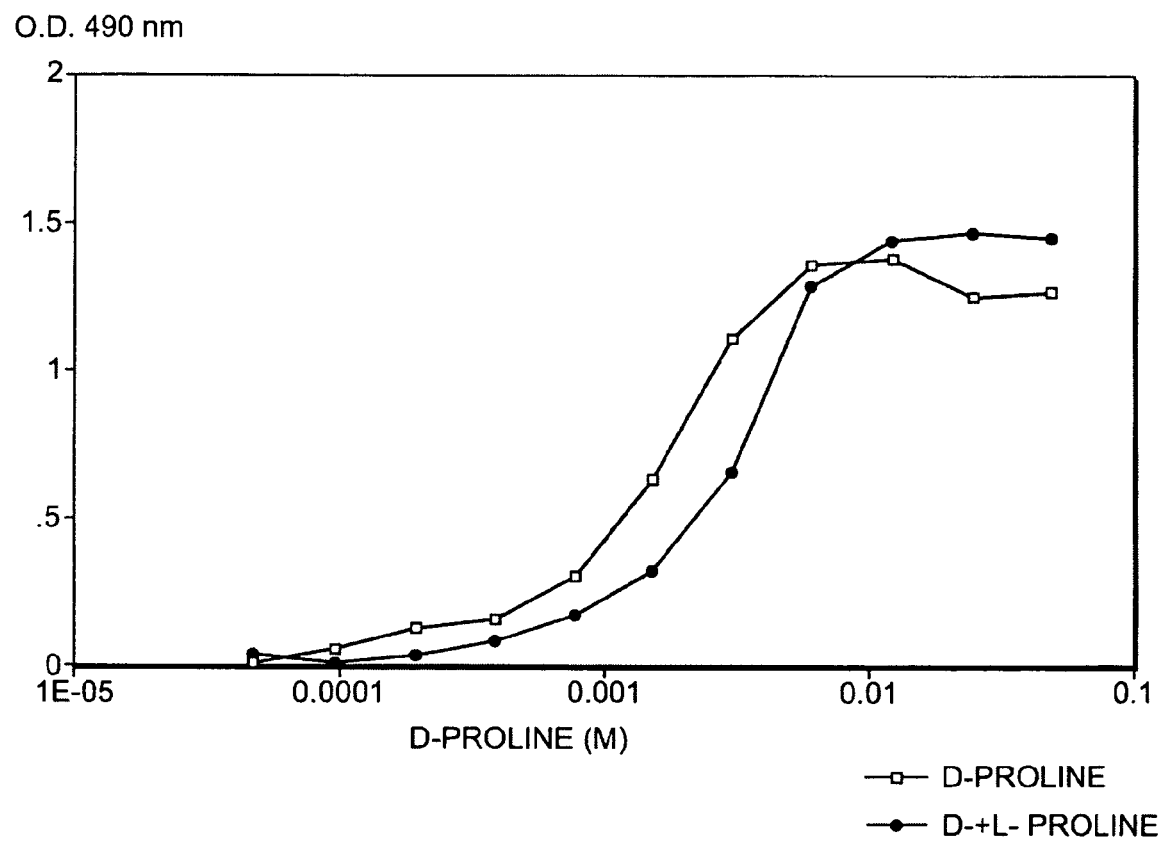
FIG. 9 shows the comparison of D-AAO/HRP reaction using D-Proline alone or an equimolar mixture of D- and L-Proline as standard.

FIG. 9 shows the comparison of D-AAO/HRP reaction using D-Proline alone or an equimolar mixture of D- and L-Proline as standard. It can be seen that the amount of D-Proline required to obtain a given optical density is higher when a mixture of L- and D-Proline are used as compared to a standard using D-proline alone. Since Proline-racemase activity ends when both L- and D-Proline are in equal amounts, it was also adequate to use an equimolar mixture of both enantiomers of Proline as standard for D-Proline determination.

EXAMPLE 15

PAC does not Interfere with DAAO/HRPactivity

Figure 10:
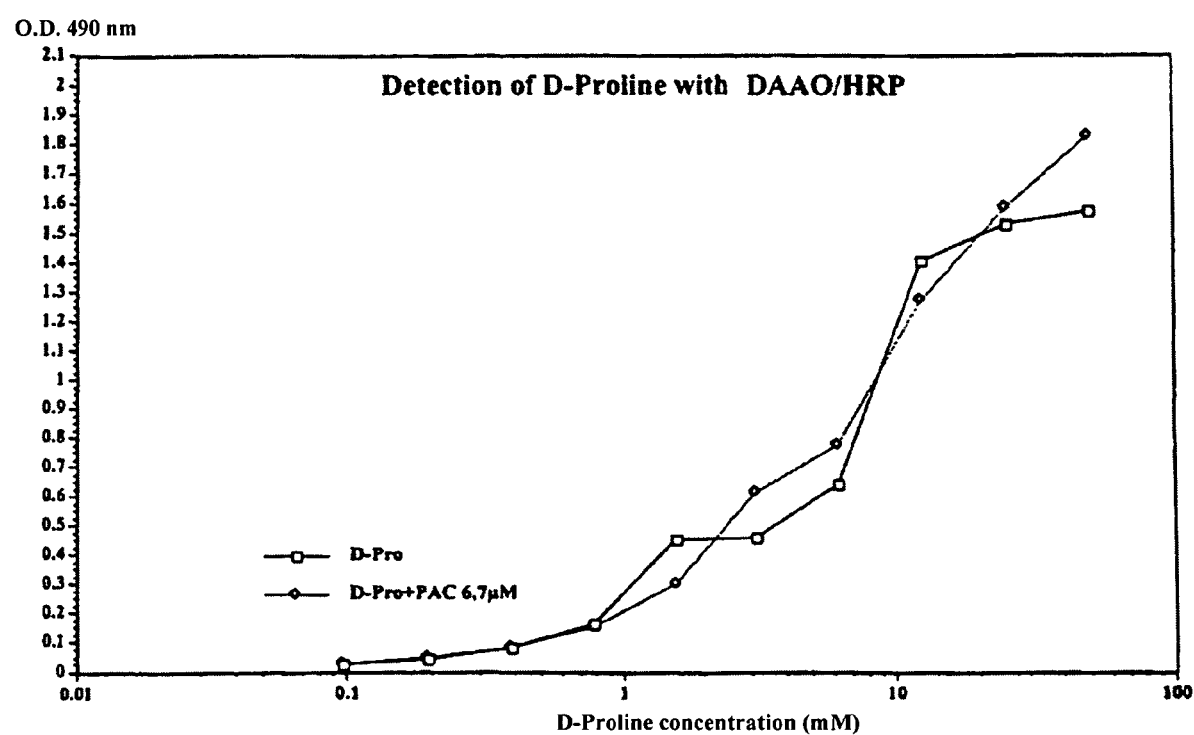
FIG. 10 shows optical density at 490 nm as a function of D-proline concentration under the following conditions.

FIG. 10 shows optical density at 490 nm as a function of D-proline concentration under the following conditions.
Conditions in µl wells,

| [D-Proline] range between 0.1 mM and 40 mM | |
| --- | --- |
| [D-AAO] | 0.89 U/ml |
| [HRP] | 37.5 U/ml |
| [OPD] | 0.5 U/ml |
| [FAD] | $1.5 \times 10^{-5}$ M |

Buffer*

The presence of PAC does not influence DAAO/HRP reaction.

EXAMPLE 16

A Medium/High Throughput Test Using the D-AAO Microplate Test

Table VII is an Example of a medium/high throughput test using the D-AAO microplate test.
Blue: D-proline standard (column 1)
Green: Positive control of racemization using avec 10 mM substrate (column 2, line A and B)
Orange: control for inhibition of racemization reaction by PAC using 10 mM substrate (column 2, line C and D)
Blank 1: mix with racemase (column 2, line E)
Blank 2: mix without racemase (column 2, line F)
Yellow: Negative control for specificity of (without racemase +40 mM L-proline) (column 2, line G and H)
Other wells: with Inhibitors (T1, T2, T3, . . . T40): in duplicates

TABLE VII

| | 1 D-Pro (mM) | 2 | 3 | 4 | 5 | 6 | 7 | 8 | 9 | 10 | 11 | 12 |
| --- | --- | --- | --- | --- | --- | --- | --- | --- | --- | --- | --- | --- |
| A | 10 | L-Pro | T1 | T2 | T3 | T4 | T5 | T6 | T7 | T8 | T9 | T10 |
| | | L-Pro | " | " | " | " | " | " | " | " | " | " |
| | | | T11 | T12 | T13 | T14 | T15 | T16 | T17 | T18 | T19 | T20 |
| | | | " | " | " | " | " | " | " | " | " | " |
| | | Blanc 1 | T21 | T22 | T23 | T24 | T25 | T26 | T27 | T28 | T29 | T30 |
| | | Blanc 1 | " | " | " | " | " | " | " | " | " | " |
| | | L-Pro | T31 | T32 | T33 | T34 | T35 | T36 | T37 | T38 | T39 | T40 |
| H | 0,07 | L-Pro | " | " | " | " | " | " | " | " | " | " |

EXAMPLE 17

Application of Such a Test for General Detection of D-amino Acids in Samples The use of a microplate test based on D-amino-acid oxidase together with a peroxidase, such as horseradish peroxidase, can be used to detect and quantitate any D-amino acid in any biological or chemical sample. For example, since D-amino acids are described to be involved in several pathological processes or neurological diseases, such as Alzheimer disease, Parkinson, or renal diseases, their detection can be an important marker or parameter for the diagnosis and the follow-up of these pathologies. This technology can be also extended to the detection and quantification of D-amino acids in eukaryotic organisms, such as plants or fungi, and in bacteria.

The D-AAO/HRP test described here above can also be used for this purpose with slight modifications. For that purpose, the racemase reaction step should be skipped and the microplate test should start straightforward at the II-1-2.1-2 step described above with the following remarks:

1) Standard: It should not be an equimolar mixture of D- and L-amino acid, but rather a serial dilution of D-Amino acids. The choice of amino acid is made according to the interest of the D-amino acid under investigation. The final volume in wells should be of 87 µl.

2) Negative control: It is made with the L-enantiomer of the D-amino acid under investigation. The final volume should be 87 µl.

3) Blank: It is made with 87 µl buffer*. (See paragraph II.1.1 Materials.)

4) Samples: The samples to be tested should be adjusted to pH 8,3 with buffer* and their final volumes should be of 87 µl per well.

Obs: Standards, negative controls, samples to test and blanks should be made in duplicates. They are dispensed into the wells of the microplate.

5) Then, the procedure follows steps 3) to 6), as above.

Several D-amino acids and their L-counterparts have been tested using the microplate test described above. Tables VIII and IX show that D-forms of Tyrosine, Valine, Threonine, Glutamic acid, Lysine and Tryptophane are indeed substrates for the D-AAO/HRP and are detected by the test, as described for D-Proline. The results also show that no L-amino acid is detected by such a methodology.

TABLE VIII

| A | Blank | 49.5 | 24.75 | 12.37 | 6.19 | 3.09 | 1.55 | 0.77 | 0.39 | 0.19 | 0.09 | 0.05 | D-pro |
|---|-------|------|-------|-------|------|------|------|------|------|------|------|------|-------|
| B | Blank | 49.5 | 24.75 | 12.37 | 6.19 | 3.09 | 1.55 | 0.77 | 0.39 | 0.19 | 0.09 | 0.05 | mM |
| C | Blank | L-Tyr | L-Val | L-Thr | L-Glu | L-Lys | L-Try | | | | | | |
| D | Blank | 12.5 | 12.5 | 12.5 | 12.5 | 12.5 | 12.5 | mM | | | | | |
| E | Blank | D-Tyr | D-Val | D-Thr | D-Glu | D-Lys | D-Try | | | | | | |
| F | Blank | 6.25 | 6.25 | 6.25 | 6.25 | 6.25 | 6.25 | mM | | | | | |

Optical densities at 490 nm obtained after D-AAO reaction. (raw OD data).

TABLE IX

| A | 0.105 | 1.961 | 1.757 | 1.814 | 1.983 | 1.716 | 1.234 | 0.809 | 0.496 | 0.308 | 0.213 | 0.173 | D-pro |
|---|-------|-------|-------|-------|-------|-------|-------|-------|-------|-------|-------|-------|-------|
| B | 0.118 | 2.004 | 1.885 | 1.976 | 1.949 | 1.879 | 1.221 | 0.824 | 0.504 | 0.32 | 0.215 | 0.159 | mM |
| C | 0.123 | 0.193 | 0.135 | 0.124 | 0.131 | 0.125 | 0.131 | L- | | | | | |
| D | 0.125 | 0.141 | 0.129 | 0.128 | 0.141 | 0.131 | 0.138 | L- | | | | | |
| E | 0.120 | 1.317 | 1.683 | 0.215 | 0.147 | 0.243 | 0.615 | D- | | | | | |
| F | 0.105 | 0.991 | 1.612 | 0.157 | 0.116 | 0.157 | 0.662 | D- | | | | | |

Figure 11:
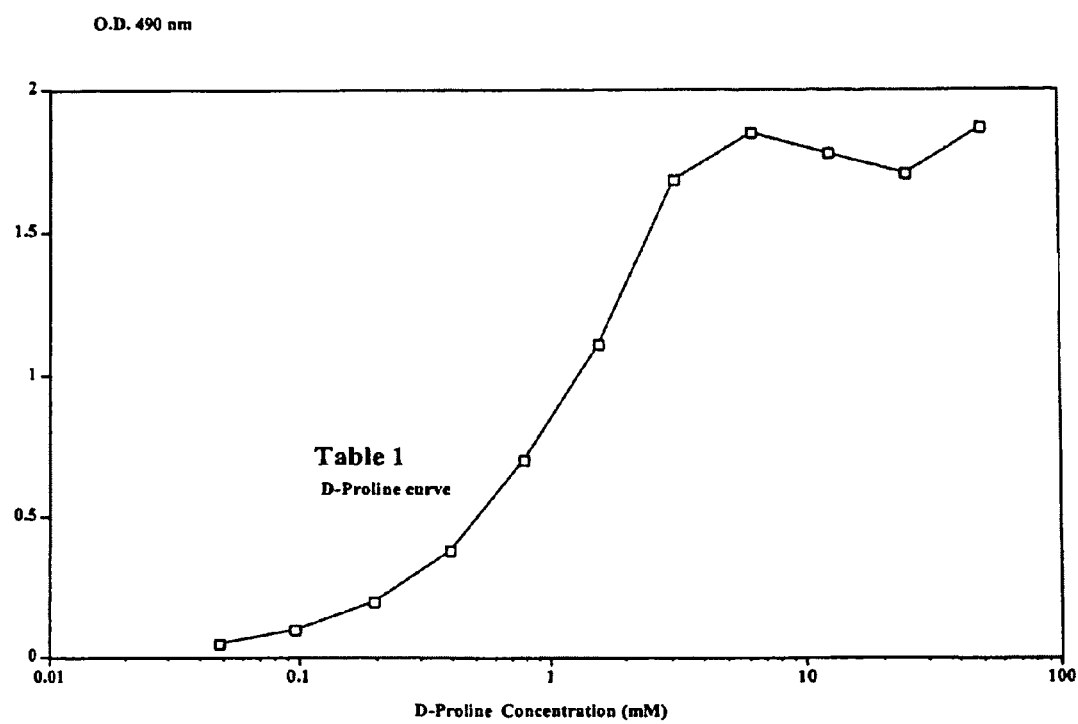
FIG. 11 is a Graph obtained with the serial dilutions of D-proline, as positive reaction control Obs: OD of wells (–) average of OD obtained from blank wells.

Template of microplate, where, a serial dilution of D-Proline (mM) was made as positive control of the D-AAO reaction. Blank wells containing buffer* are shown. Different L- and D-amino acids were tested, namely Tyrosine (Tyr), Valine (Val), Threonine (Thr), Glutamic acid (Glu), Lysine (Lys) and Tryptophan (Try). To highlight the sensitivity of the D-AAO microtest, higher concentrations of L-enantiomers (12.5 mM) were used in the reactions as compared to the concentrations used for D-enantiomers (6.25 mM):

FIG. 11 is a Graph obtained with the serial dilutions of D-proline, as positive reaction control Obs: OD of wells (−) average of OD obtained from blank wells.

A preferred platform to search and quantitate the presence of a D-Amino acid in samples contains at least the following products:

A D-amino acid,

A peroxidase and a substrate of a peroxidase

A D-amino-acid oxidase

And optionally, a L-amino acid enantiomer, as control.

Finally, this invention relates to a method for screening a molecule, which can modulate a racemase activity, wherein the method comprises:

(A) modulating a racemase activity by means of a molecule being tested in the presence of an equimolar mixture of a L- and D-amino acid and of a racemase to be modulated;

(B) oxidatively deaminating the D-amino acid generated in step (A) by means of a D-amino oxidase in a prosthetic group; and (C) detecting the hydrogen peroxide generated by the oxidative deamination;

wherein modulation of the hydrogen peroxide is indicative of the capability of the tested molecule to modulate racemase activity. Preferably the molecule inhibits racemase activity, and more preferably the racemase is a proline racemase, for example, *Tripanosoma curzi* proline racemase. A molecule identified by a method is also part of this invention.

Further, this invention relates to technological platform and all reagents and devices necessary to perform the methods of the invention. The technological platform comprises:

a) L-amino acid, D-amino acid, and a racemase;

b) a peroxydase and a substrate of a peroxydase, or a catalase and a reagent sensitive to oxygen;

c) a D-amino acid oxidase; and d) optionally, one or more molecules to be screened for inhibitory activity of said racemase.

Preferably, the racemase is a proline racemase and the L-amino acid and D-amino acid are L-proline and D-proline, respectively.

A molecule inhibits a proline racemase containing a subsequence selected from the SEQ ID NO: 1, 2, 3 or 4.

EXAMPLE 18

Signature of Proline Racemases DRSP
C̲GXGXXAXXA

The signature of proline racemases DRSP C̲GXGXXAXXA (SEQ ID NO: 4) defined here as Motif III* contains de residue Cy330 that is also observed in the sequences here above. Fragments of the different sequences and contigs contain also the NMC̲GH motif (SEQ ID NO: 128), corresponding to the sequence around residue Cys160 of TcPRAC, shown to be important for the enzymatic activity. Some examples are depicted here below. The sequences related to the crucial Cys residues for proline racemase activity are squared.

Squared: NMCGH (SEQ ID NO: 128) (Cys$^{160}$) residues and
DRSPCGTGTSAKMA (SEQ ID NO: 127)(Motif III, signature containing
Cys$^{330}$) residues

*1- Bacillus anthracis*

```
>gnl |TIGR_1392| banth_4742 Bacillus anthracis unfinished fragment of complete genome
          Length = 11981

Score = 141 bits (302), Expect (3) = 4e-69
 Identities = 60/146 (41%), Positives = 91/146 (62%)
 Frame = +1 / -3

(SEQ ID NOS 57 AND 58)

Query: 763   GEVRVDIAFGGNFFAIVPAEQLGIDISVQNLSRLQEAGELLRTEINRSVKVQHPQLPHIN  942
             G V  DIA+GGNF+AI+ A+ +G+++  ++ S + +    +R  IN  ++ HP+   I
Sbjct: 8379  GTVEADIAYGGNFYAIIDAKSVGLELVPEHASTIIDKAIHIRNIINERFEIIHPEYSFIR 8200

Query: 943   TVDCVEIYGPPTNPEANYKNVVIFGNRQADRSPCGTGTSAKMATLYAKGQLRIGETFVYE 1122
               +  VE Y  PT+  A+ KN V+       DRSPCGTGTSAK+A LYA  ++ + E FV+E
Sbjct: 8199  GLTHVEFYTDPTHESAHVKNTVVVPPGGIDRSPCGTGTSAKLAVLYANQKIEMNEEFVHE 8020

Query: 1123  SILGSLFQGRVLGEERIPGVKVPVTK  1200
             SI+GSLF+G V+    + ++ VTK
Sbjct: 8019  SIVGSLFKGCVINTTNVANMEAVVTK  7942

Score = 137 bits (294), Expect (3) = 4e-69
 Identities = 54/117 (46%), Positives = 79/117 (67%)
 Frame = +1 / -3

(SEQ ID NOS 59 AND 60)

Query: 262   MRFKKSFTCIDMHTEGEAARIVTSGLPHIPGSNMAEKKAYLQENMDYLRRGIMLEPRGHD 441
             MR +K FT ID HT G   R + SGLP + G  MAEK  ++++  D++R+ +M EPRGHD
Sbjct: 8859  MRTQKVFTTIDTHTGGNPTRTLISGLPKLLGETMAEKMLHMKKEYDWIRKLLMNEPRGHD 8680

Query: 442   DMFGAFLFDPIEEGADLGMVFMDTGGYLNMCGHNSIAAVTAAVETGIVSVPAKATNV  612
              M GA L DP     AD+G+++++TGGYL MCGH++I  TA +E+G++ V
Sbjct: 8679  VMSGALLTDPCHPDADIGVIYIETGGYLPMCGHDTIGVCTALIESGLIPVVEPITSL 509

>gnl |TIGR_1392| banth_4799 Bacillus anthracis unfinished fragment of complete genome
          Length = 22506

Score = 125 bits (267), Expect (4) = 4e-68
 Identities = 56/145 (38%), Positives = 86/145 (59%)
 Frame = +1 / -3

(SEQ ID NOS 61 AND 62)

Query: 766   EVRVDIAFGGNFFAIVPAEQLGIDISVQNLSRLQEAGELLRTEINRSVKVQHPQLPHINT 945
             E +VDIAFGG F+A+V +++ G+ +  ++LS +Q+  G  ++  I  ++V HP     +
Sbjct: 5188  EFQVDIAFGGAFYAVVDSKEFGLKVDFKDLSAIQQWGGKIKHYIESKMEVKHPLEEGLKG 5009
```

```
Query:   946  VDCVEIYGPPTNPEANYKNVVIFGNRQADRSPCGTGTSAKMATLYAKGQLRIGETFVYES  1125
              +  V      P    A  +NV IF + Q DRSPCGTGTSA++ATL+ KG L+ GE F++E
Sbjct:  5008  IYGVIFSDDPKGEGATLRNVTIFADGQYDRSPCGTGTSARIATLFEKGILQKGEIFIHEC  4829

Query:  1126  ILGSLFQGRVLGEERIPGVKVPVTK  1200
              I    F+G VL   +  +  V  K
Sbjct:  4828  ITDGEFEGEVLSVTAVHTYEAVVPK  4754

Score =  124 bits (266), Expect (4) = 4e-68
 Identities = 48/113 (42%), Positives = 65/113 (57%)
 Frame = +1 / -3

(SEQ ID NOS 63 AND 64)

Query:   262  MRFKKSFTCIDMHTEGEAARIVTSGLPHIPGSNMAEKKAYLQENMDYLRRGIMLEPRGHD  441
              M+  K +T ID H GE  RI+T G+P I G     E++ Y E++DYLR  +M EPRGH
Sbjct:  5662  MKVSKVYTTIDAHVAGEPLRIITGGVPEIKGETQLERRWYCMEHLDYLREVLMYEPRGHH  5483

Query:   442  DMFGAFLFDPIEEGADLGMVFMDTGGYLNMCGHNSIAAVTAAVETGIVSVPAK  600
              M+G   +  P   AD G++FM   G+   MCGH  IA +T +ETG+     K
Sbjct:  5008  GMYGCIITPPASAHADFGVLFMHNEGWSTMCGHGIIAVITVGIETGMFETKQK  5324

2- *Clostridium botulinum*

>gnl |SANGER_36826| cbotul_Contig173 *Clostridium botulinum* A unfinished fragment of
complete genome
          Length = 97750

Score =  178 bits (383), Expect (4) = 4e-98
 Identities = 70/138 (50%), Positives = 102/138 (73%)
 Frame = +1 / -2

(SEQ ID NOS 65 AND 66)

Query:   760  YGEVRVDIAFGGNFFAIVPAEQLGIDISVQNLSRLQEAGELLRTEINRSVKVQHPQLPHI  939
              YG++  +DI+FGG+FFA+V AE++GIDIS N  +L + G   +N V+++HP L HI
Sbjct: 70443  YGKLTLDISFGGSFFAMVDAEKVGIDISPANSQKLNDLGMKIVHAVNEQVEIKHPVLEHI  70264

Query:   940  NTVDCVEIYGPPTNPEANYKNVVIFGNRQADRSPCGTGTSAKMATLYAKGQLRIGETFVY  600
                TVD   E YGP +  +A+ +NVV+FG Q  DRSPCGTGTSAKMA LYA+G++++GE V
Sbjct: 70263  KTVDLCEFYGPAKSEDADVQNVVVFGQGQVDRSPCGTGTSAKMALLYAQGKMKVGEEIVN  70084

Query:  1120  ESILGSLFQGRVLGEERI  1173
              ESI+   F+G++L E ++
Sbjct: 70083  ESIICTKFKGKILEETKV  70030

Score =  166 bits (357), Expect (4) = 4e-98
 Identities = 70/118 (59%), Positives = 81/118 (68%)
 Frame = +1 / -2

(SEQ ID NOS 67 AND 68)

Query:   259  IMRFKKSFTCIDMHTEGEAARIVTSGLPHIPGSNMAEKKAYLQENMDYLRRGIMLEPRGH  438
              IMR K+   I+  HT GE  RIV GLP +PG  MAEK MEYL+EN D LR  +M EPRGH
Sbjct: 70926  IMRAIKTIQTIESHTMGEPTRIVIGGLPKVPGKTMAEKMEYLEENNDSLRTMLMSEPRGH  70747
```

-continued

```
Query: 439   DDMFGAFLFDPIEEGADLGMVFMDTGGYINMCGHNSIAAVTAAVETGIVSVPAKATNV   612
             +DMFGA    +P +E ADLG++FMD GGYINMCGH SI A T AVE GIV V    TN+
Sbjct: 70746 NDMFGAIYTEPADETADLGIIFMDGGGYINMCGHGSIGAATCAVEMGIVKVEEPYTNI   70573

> SANGER Cbot12g05.q1c
Score = 584 (210.6 bits), Expect = 7.7e-57, P = 7.7e-57
 Identities = 115/224 (51%), Positives = 156/224 (69%), Frame = -2

(SEQ ID NOS 69 AND 70)

Query: 75    ADLGIVFMDTGGYLNMCGHNSIAAVTAAVETGILSVPAKATNVPVVLDTPAGLVRGTAHL   134
             ADLGI+FMD GGYLNMCGH SI A T AVE GI+ V   TN+   L+ PAG++     +
Sbjct: 654   ADLGIIFMDGGGYLNMCGHGSIGAATCAVEMGIVKVEEPYTNIK--LEAPAGMINARVRV   481

Query: 135   QSGTESEVSNASIINVPSFLYQQDVVIVLPKPYGEVRVDIAFGGNFFAIVPAEHLGIDIS   194
             + G   E S    I+NVP+FLY++DV I  +P   YG++ +DI+FGG+FFA+V AE +GIDIS
Sbjct: 480   EDGKAKETS---IVNVPAFLYKKDVEIDVPD-YGKLTLDISFGGSFFAMVDAEKVGIDIS   313

Query: 195   VQNLSRLQEAGELLRTEINRSVKVQHPQLPHINTVDCVEIYGNATVPEAKYKNVVIFGNR   254
             N  +L + G  +   +N V+++HP L HI TVD  E YG A + +A  +NVV +FG
Sbjct: 312   PANSQKLNDLGMKIVHAVNEQVEIKHPVLEHIKTVDLCEFYGPAKSEDADVQNVVVFGQG   133

Query: 255   QADRSPCGTGTSAKMATLYAKGQLRIGETFVYESILGSLFQGRV   298
             Q DRSPCGTGTSAKMA LYA+G++++GE  V ESI+ + FQG++
Sbjct: 132   QVDRSPCGTGTSAKMALLYAQGKMKVGEEIVNESIICTKFKGKI   1

3- Aspergillus fumigatus

>gnl |TIGR_5085| afumi_1044 Aspergillus fumigatus unfinished fragment of complete genome
           Length = 7621

Score = 46.0 bits (94), Expect (4) = 3e-16
 Identities = 21/72 (29%), Positives = 34/72 (47%)
 Frame = +1 / +2

(SEQ ID NOS 71 AND 72)

Query: 973   PTNPEANYKNVVIFGNRQADRSPCGTGTSAKMATLYAKGQLRIGETFVYESILGSLFQGR   1152
             P + +     + F  Q DRSP G+   A+MA  YAKG  +G+ + Y S++ + F
Sbjct: 6227  PDDVQGAETGLCYFAENQIDRSPTGSCVIARMALAYAKGLRSLGQRWAYNSLVSNRFGTG   6406

Query: 1153  VLGEERIPGVKV   1188
             E + V +
Sbjct: 6407  AFSAEIVEEVTI   6442

Score = 40.9 bits (83), Expect (4) = 3e-16
 Identities = 13/34 (38%), Positives = 26/34 (76%)
 Frame = +1 / +2

(SEQ ID NOS 73 AND 74)

Query: 361   MAEKKAYLQENMDYLRRGIMLEPRGHDDMFGAFL   462
             + E++   +++ D++R+ +MLEPRGH M+GA +
Sbjct: 5513  LLEQRDQAKQHHNHIRKCLMLEPRGHNGMYGAII   5614

Score = 40.0 bits (81), Expect (4) = 3e-16
 Identities = 14/29 (48%), Positives = 20/29 (68%)
 Frame = +1 / +2
```

-continued (SEQ ID NOS 75 AND 76)

```
Query: 286   CIDMHTEGEAARIVTSGLPHIPGSNMAEK   372
             CIDMHT GE  RI+ SG P + G+ + ++
Sbjct: 5441  CIDMHTTGEPTRIIYSGFPPLSGTLLEQR   5527
```

Score = 32.2 bits (64), Expect (4) = 3e-16
 Identities = 12/27 (44%), Positives = 20/27 (74%)
 Frame = +1 / +2

(SEQ ID NOS 77 AND 78)

```
Query: 775   VDIAFGGNFFAIVPAEQLGIDISVQNL   462
             +DI++GG F+AIV A +LG    +++L
Sbjct: 5996  LDISYGGAFYAIVQASELGFSGGLRDL   6076
```

Score = 25.8 bits (50), Expect (4) = 5e-04
 Identities = 12/21 (57%), Positives = 13/21 (61%)
 Frame = -2 / -2

(SEQ ID NOS 79 AND 80)

```
Query: 479   SSIGSNKKAPNISS*PRGSSI   462
             SS+    AP I  *PRGSSI
Sbjct: 5631  SSVSGRMMAPYIPL*PRGSSI   5569
```

4- *Clostridium difficile*

>gnl |SANGER_1496| cdifficile_1080 *Clostridium difficile* unfinished fragment of complete genome
          Length = 204145

Score = 209 bits (451), Expect (4) = e-109
 Identities = 86/146 (58%), Positives = 107/146 (73%)
 Frame = +1 / -2

(SEQ ID NOS 81 AND 82)

```
Query: 763   GEVRVDIAFGGNFFAIVPAEQLGIDISVQNLSRLQEAGELLRTEINRSVKVQHPQLPHIN   942
             G V+ DI+FGG+FFAI+ A QLG+ I  QN +L E    LR  IN  +++QHP L HI
Sbjct: 88224 GTVKFDISFGGSFFAIIHASQLGLKIEPQNAGKLTELAMKLRDIINEKIEIQHPTLAHIK 88045

Query: 943   TVDCVEIYGPPTNPEANYKNVVIFGNRQADRSPCGTGTSAKMATLYAKGQLRIGETFVYE   1122
             TVD VEIY  PT+PEA YKNVVIFG  Q D RSPCGTGTSAK+AT L+AKG+L++GE FVYE
Sbjct: 88044 TVDLVEIYDEPTHPEATYKNVVIFGQGQVDRSPCGTGTSAKLATLHARGELKVGEKFVYE 87865

Query: 1123  SILGSLFQGRVLGEERIPGVKVPVTK              1200
             SILG+LF+G ++ E ++     V K
Sbjct: 87864 SILGTLFKGEIVEETKVADFNAVVPK              87787
```

Score = 173 bits (373), Expect (4) = e-109
 Identities = 68/117 (58%), Positives = 86/117 (73%)
 Frame = +1 / -2

(SEQ ID NOS 83 AND 84)

```
Query: 262   MRFKKSFTCIDMHTEGEAARIVTSGLPHIPGSNMAEKKAYLQENMDYLRRGIMLEPRGHD   441
             M+F +S   ID HT GEA RIV  G+P+I G++M EKK YL+EN+DYLR  IMLEPRGH+
Sbjct: 88707 MKFSRSIQAIDSHTAGEATRIVVGGIPNIKGNSMPEKKEYLEENLDYLRTAIMLEPRGHN 88528
```

-continued

```
Query: 442   DMFGAFLFDPIEEGADLGMVFMDTGGYLNMCGHNSIAAVTAAVETGIVSVPAKATNV  612
             DMFG+ +  P    AD G++FMD GGYLNMCGH +I A+TAA+ETG+V
Sbjct: 88527 DMFGSVMTQPCCPDADFGIIFMDGGGYLNMCGHGTIGAMTAAIETGVVPAVEPVTHV  88357
```

5- *Brucella suis*

```
>gnl |TIGR_29461| bsuis_1327 Brucella suis unfinished fragment of complete genome Length = 69104

Score = 150 bits (323), Expect (5) = 3e-73
  Identities = 62/139 (44%), Positives = 92/139 (66%)
  Frame = +1 / -2
 (SEQ ID NOS 85 AND 86)

Query: 763   GEVRVDIAFGGNFFAIVPAEQLGIDISVQNLSRLQEAGELLRTEINRSVKVQHPQLPHIN  942
             G ++VD+A+GGNF+AIV  ++   D+    +  +L     +LR  +N   K QHP+LP IN
Sbjct: 24931 GPIKVDVAYGGNFYAIVEPQENYTDMDDYSALQLIAWSPVLRQRLNEKYKFQHPELPDIN  24752

Query: 943   TVDCVEIYGPPTNPEANYKNVVIFGNRQADRSPCGTGTSAKMATLYAKGQLRIGETFVYE  1122
              +   +    G P +P+A+ +N V +G++  DRSPCGTGTSA+MA L AKG+L+ G+ F++E
Sbjct: 24751 RLSHILWTGKPKHPQAHARNAVFYGDKAIDRSPCGTGTSARMAQLAAKGKLKPGDEFIHE  24572

Query: 1123  SILGSLFQGRVLGEERIPG  1179
             SI+GSLF GRV     + G
Sbjct: 24571 SIIGSLFHGRVERAAEVAG  24515

Score = 122 bits (262), Expect (5) = 3e-73
  Identities = 47/106 (44%), Positives = 68/106 (64%)
  Frame = +1 / -2
 (SEQ ID NOS 87 AND 88)
Query: 271   KKSFTCIDMHTEGEAARIVTSGLPHIPGSNMAEKKAYLQENMDYLRRGIMLEPRGHDDMG  450
             + SF C+D HT G    R+V  G P++ GS M EK+A+      D++R G+M EPRGHD M
Sbjct: 25402 RHSFFCVDGHTCGNPVRLVAGGGPNLNGSTMMEKRAHFLAEYDWIRTGLMFEPRGHDMMS  25223

Query: 451   GAFLFDPIEEGADLGMVFMDTGGYINMCGHNSIAAVTAAVETGIVS   588
             G+ L+ P     D+ ++F++T G I MCGH +I  VT A+E G+V+
Sbjct: 25222 GSILYPPTRPDCDVAVLFIETSGCIPMCGHGTIGTVTMAIEQGLVT   25085
```

6- *Rhodobacter sphaeroides*

```
>gnl |UTHSC_1063| rsphaer_x8758Contig3    Length = 2326

Score = 124 bits (265), Expect (5) = 8e-41
  Identities = 50/109 (45%), Positives = 70/109 (64%)
  Frame = +1 / +2
(SEQ ID NOS 89 AND 90)
Query: 262   MRFKKSFTCIDMHTEGEAARIVTSGLPHIPGSNMAEKKAYLQENMDYLRRGIMLEPRGHD  441
             MR +   +  I  HTEGE   I+ SG+P+   GS + EK+A+L+EN D+LR+ +M EPRGH
Sbjct: 1448  MRVQDVYNVIYTHTEGEPLCIIYSGVPYPAGSTILEKRAFLEENYDWLRKALMREPRGHA  1627

Query: 442   DMFGAFLFDPIEEGADLGMVFMDTGGYINMCGHNSIAAVTAAVETGIVS  588
             DMFG FL  P     D G++++D    Y +MCGH +IA   A V  G+V+
Sbjct: 1628  DMFGVFLTPPSSRDYDAGLIYIDGKEYSHMCGHGTIAVAMAMVANGLVA  1774
```

```
 Score = 65.2 bits (136), Expect = 4e-09
 Identities = 38/95 (40%), Positives = 51/95 (53%)
 Frame = -2 / -2
 Score = 34.1 bits (68), Expect (5) = 8e-41
 Identities = 18/47 (38%), Positives = 23/47 (48%)
 Frame = +1 / +2
```

(SEQ ID NOS 91 AND 92)

```
Query: 910   KVQHPQLPHINTVDCVEIYGPPTNPEANYKNVVIFGNRQADRSPCGT    600
             K   P   HIN ++ V ++  P +   YKNV F   Q DR P GT
Sbjct: 2084  KSSTPTEAHINNLNFVTLWHKPPSRGWLYKNVHCFLEGQLDRLPGGT    2224
```

7- *Burkholderia pseudomallei*

>gnl |SANGER_28450| bpsmalle_Contig394 *Burkholderia pseudomallei* unfinished fragment of complete genome

```
         Length = 3107
 Score = 105 bits (224), Expect (3) = 1e-33
 Identities = 47/118 (39%), Positives = 59

```
 Score = 60.6 bits (126), Expect (3) = 4e-33
 Identities = 27/63 (42%), Positives = 38/63 (60%)
 Frame = +1 / -1
```

(SEQ ID NOS 99 AND 100)

```
Query: 979    NPEANYKNVVIFGNRQADRSPCGTGTSAKMATLYAKGQLRIGETFVYESILGSLFQGRVL  618
              +PE + ++ V+    DRSPCGTGTSAK+A L A G+L  G T+   S++GS+F
Sbjct: 1953   DPEYDSRSFVLCPGHAYDRSPCGTGTSAKLACLAADGKLVAGVTWRQASVIGSVFSASYA  1774

Query: 1159   GEE  1167
              E
Sbjct: 1773   AAE  1765
```

9- *Pseudomonas putida*

>gnl |TIGR| pputida_13538 *Pseudomonas putida* unfinished fragment of complete genome
        Length = 6184039

```
 Score = 108 bits (230), Expect (2) = 1e-32
 Identities = 45/115 (39%), Positives = 64/115 (55%)
 Frame = +1 / -2
```

(SEQ ID NOS 101 AND 102)

```
Query: 274    KSFTCIDMHTEGEAARIVTSGLPHIPGSNMAEKKAYLQENMDYLRRGIMLEPRGHDDMFG  618
              K    ID HT GE  R+V  G P + G +MAE++  L+E  D  RR  +LEPRG+D + G
Sbjct: 909066 KQIHVIDSHTGGEPTRLVMKGFPQLRGRSMAEQRDELRELHDRWRRACLLEPRGNDVLVG  908887

Query: 454    AFLFDPIEEGADLGMVFMDTGGYINMCGHWSIAAVTAAVETGIVSVPAKATNVPV  618
              A   P+    A G++F +  GYINMCGH +I V    G+++      + PV
Sbjct: 908886 ALYCPPVSADATCGVIFFNNAGYINMCGHGTIGLVASLQHMGLITPGVHKIDTPV  908722
```

```
 Score = 71.2 bits (149), Expect (2) = 1e-32
 Identities = 31/58 (53%), Positives = 40/58 (68%)
 Frame = +1 / -2
```

(SEQ ID NOS 103 AND 104)

```
Query: 979    NPEANYKNVVIFGNRQADRSPCGTGTSAKMATLYAKGQLRIGETFVYESILGSLFQGR  1152
              +P A+ +N V+   +   DRSPCGTGTSAK+A L A G+L  G+T+V  SI GS F GR
Sbjct: 908427 DPNADSRNFVMCPGKAYDRSPCGTGTSAKLACLAADGKLAEGQTWVQASITGSQFHGR  908254
```

10- *Leishmania major*

SANGER
LM16_BIN_Contig2054 *L. major* Friedlin contig not yet a...2.5e-31    3
LM16W5b02.q1c          2.3e-19     1
LM16B3d03.p1c          3.1e-05     3

>LM16_BIN_Contig2054 *L. major* Friedlin contig not yet assigned to chromosome
        from LM16 bin, unfinished whole chromosome shotgun data sequenced
        by the Wellcome Trust Sanger Institute, Contig number Contig2054
        length 873 bp
        Length = 873

```
 Score = 242 (90.2 bits), Expect = 2.5e-31, Sum P(3) = 2.5e-31
 Identities = 61/180 (33%), Positives = 91/180 (50%), Frame = +2
 [HSP Sequence]
```

(SEQ ID NOS 105 AND 106)

```
Query: 93    SGLPHIPGSNMAEKKAYLQENMDYLRRGIMLEPRGHDDMFGAFLFDPIEEGADLGIVFMD  152
             +G P + G +A+K  L+   D  RR  +LEPRG+D + GA    P+    A  G++F +
Sbjct: 2     TGFPELAGETIADKLDNLRTQHDQWRRACLLEPRGNDVLVGALYCAPVSADATCGVIFFN  181
```

```
Query: 153  TGGYLNMCGHMSIAAVTAAVETGIVSVPAKATNVPVVLDTPAGLVRGTAHLQSGTESEVS 1152
            GYL MCGH +I V +   G +    A V   + DTP G V   T H
Sbjct: 182  NAGYLGMCGHGTIGLVASLHHLGRI-----APGVHKI-DTPVGPVSATLHADGAV----- 328

Query: 213  NASIINVPSFLYQQDVVVVLPKPYGEVRVDIAFGGNFFAIVPAEQLGIDISVQNLSRLQE 272
            ++ NVP++ Y+Q V V +P  +G V  DIA+GGN F +V       G  + + N+ L +
Sbjct: 329  --TLRNVPAYRYRQQVPVDVPG-HGRVYGDIAWGGNWFFLVSDH--GQALQMDNVEALTD 493

Score = 91 (37.1 bits), Expect = 2.5e-31, Sum P(3) = 2.5e-31
  Identities = 24/69 (34%), Positives = 34/69 (49%), Frame = +3
  [HSP Sequence]

(SEQ ID NOS 107 AND 108)

Query: 307  PTNPEANYKNVVIFGNRQADRSPCGTGTSAKMATLYAKGQLRIGETFVYESILGSLFQGR 366
            PT P         +    DRSPCGTGT+AK+A  L   +L  GE ++   +I    F+
Sbjct: 579  PTTPTPTA*TSSCAQGKAYDRSPCGTGTNAKLAQLAGDSKLAAGEPWLQVTITCRQFKRS 758

Query: 367  VLGE-ERIP  374
            E +R+P
Sbjct: 759  YQWECKRVP  785

Score = 48 (22.0 bits), Expect = 2.5e-31, Sum P(3) = 2.5e-31
  Identities = 11/28 (39%), Positives = 16/28 (57%), Frame = +3
  [HSP Sequence]

(SEQ ID NOS 109 AND 110)

Query: 391  VTAEITGKAFIMGFNTMLFDPTDPFKNG 418
            V   IT +A++   +T+L D  DPF  G
Sbjct: 780  VPPSITRRAYMTADSTLLID*QDPFAWG 863

>LM16W5b02.q1c
Score = 245 (91.3 bits), Expect = 2.3e-19, P = 2.3e-19
 Identities = 62/182 (34%), Positives = 92/182 (50%), Frame = +1
 [HSP Sequence]

(SEQ ID NOS 111 AND 112)

Query: 91   VTSGLPHIPGSNMAEKKAYLQENMDYLRRGIMLEPRGHDDMFGAFLFDPIEEGADLGIVF 150
            V +G P +  G  +A+K    L+   D RR +LEPRG+D + GA    P+   A G++F
Sbjct: 1    VMTGFPELAGETIADKLDNLRTQHDQWRRACLLEQRGNDVLVGALYCAPVSADATCGVIF 180

Query: 151  MDTGGYLNMCGHNSIAAVTAAVETGIVSVPAKATNVPVVLDTPAGLVRGTAHLQSGTESE 210
            +   GYL MCGH +I V +   G +    A V   + DTP G V   T H
Sbjct: 181  FNNAGYLGMCGHGTIGLVASLHHLGRI-----APGVHKI-DTPVGPVSATLHADGAV--- 333

Query: 211  VSNASIINVPSFLYQQDVVVVLPKPYGEVRVDIAFGGNFFAIVPAEQLGIDISVQNLSRL 270
            ++ NVP++ Y+Q V V +P  +G V  DIA+GGN+F +V       G  + + N+ L
Sbjct: 334  ----TLRNVPAYRYRQQVPVDVPG-HGRVYGDIAWGGNWFFLVSDH--GQALQMDNVEAL 492

Query: 271  QE  272
            +
Sbjct: 493  TD  498

11. Trypanosoma brucei
SANGER
>tryp_IXb-28b06.q1c
Score = 305 (112.4 bits), Expect = 5.4e-27, P = 5.4e-27
 Identities = 61/142 (42%), Positives = 84/142 (59%), Frame = -2
 [HSP Sequence]
```

```
(SEQ ID NOS 113 AND 114)
Query:   20 RIVTSGLPHIPGSNMAEKKAYLQENMDYLRRGIMLEPRGHDDMFGAFLEDPIEEGADLGI 79
            RI+T G+P I G     E++AY E++DYLR +M EPRGH M+G +   P    AD G+
Sbjct:  421 RIITGGVPEIKGETQLERRAYCMEHLDYLREILMYEPRGHHGMYGCIITPPASAHADFGV 242

Query:   80 VFMDTGGYLNMCGHNSIAAVTAAVETGILSVPAKATNVPVVLDTPAGLVRGTAHLQSGTE 139
            +FM  G+  MCGH  IA +T +ETG+ V +  N  ++D+PAG V    A
Sbjct:  241 LFMHNEGWSTMCGHGIIAVITVGIETGMFEVKGEKQNF--IIDSPAGEVIAYAKYNG--- 77

Query:  140 SEVSNASIINVPSFLYQQDVVI 161
            SEV + S  NVPSF+Y++DV I
Sbjct:   76 SEVESVSFENVPSFVYKKDVPI 11

>tryp_IXb-28b06.p1c
[Full Sequence]
Score = 296 (109.3 bits), Expect = 4.8e-26, P = 4.8e-26
 Identities = 59/140 (42%), Positives = 82/140 (58%), Frame = +1
[HSP Sequence]

(SEQ ID NOS 115 AND 116)
Query:   22 VTSGLPHIPGSNMAEKKAYLQENMDYLRRGIMLEPRGHDDMFGAFLDPIEEGADLGIVF 81
            +T G+P I G     E++AY E++DYLR +M EPRGH M+G +   P    AD G++F
Sbjct:   10 ITGGVPEIKGETQLERRAYCHEHLDYLREILMYEPRGHHGMYGCIITPPASAHADFGVLF 189

Query:   82 MDTGGYLNMCGHNSIAAVTAAVETGILSVPAKATNVPVVLDTPAGLVRGTAHLQSGTESE 141
            M  G+  MCGH  IA +T +ETG+ V +  N  ++D+PAG V    A        SE
Sbjct:  190 MHNEGWSTMCGHGIIAVITVGIETGMFEVKGEKQNF--IIDSPAGEVIAYAKYNG---SE 354

Query:  142 VSNASIINVPSFLYQQDVVI 161
            V + S  NVPSF+Y++DV I
Sbjct:  355 VESVSFENVPSFVYKKDVPI 414

12. Trypanosoma congolense

SANGER>congo208e06.p1kw
[Full Sequence]
        Length = 478
 Plus Strand HSPs: Score = 104 (41.7 bits), Expect = 0.00070, P = 0.00070
 Identities = 31/103 (30%), Positives = 56/103 (54%), Frame = +3
[HSP Sequence]

(SEQ ID NOS 117 AND 118)
Query:  187 FGGNFFAIVPAEQLGIDISVQNLSRLQEAGELLRTEINRSVKVQHPQLPHINTVDCVEIY 246
            +GGN+F +V   G  ++ N+ L +       +N +++ Q+        +D +E++
Sbjct:   54 WGGNWFFLVSDH--GHELQMDNVEALTDYTWAM---LN-ALEAQGIRGADGALIDHIELF 215

Query:  247 GPPTNPEANYKNVVIFGNRQADRSPCGTGTSAKMATLYAKGQL 289
              +   A+ +N V+ +    DRSPCGTGTSAK+A  L A  +L
Sbjct:  216 ADDAH--ADSRNFVMCPGKAYDRSPCGTGTSAKLACLAADAKL 338 >

SANGER>congo208e06.p1kw
[Full Sequence]
        Length = 164
 Plus Strand HSPs: Score = 78 (32.5 bits), Expect = 0.085, P = 0.082
 Identities = 19/55 (34%), Positives = 34/55 (61%), Frame = +3
[HSP Sequence]
```

(SEQ ID NOS 119 AND 120)

```
Query: 160 NVPSFLYQQDVVVLPKPYGEVRVDIAFGGNFFAIVPAEQLGIDISVQNLSRLQE  161
            +VP++ Y++ V V +P  +G V  DIA+GGN+F +V    G ++ + N+ L +
Sbjct:   3 HVPAYRYRKQVPVEVPG-HGVVLGDIAWGGNWFFLVSDH--GHELQMDNVEALTD 158
```

13. *Trypanosoma vivax*

```
SANGER>Tviv655d02.p1k 4405 bp, 11 reads, 51.90 AT
[Full Sequence]
        Length = 4405
 Plus Strand HSPs: Score = 403 (146.9 bits), Expect = 4.3e-37, P = 4.3e-37
 Identities = 77/117 (65%), Positives = 91/117 (77%), Frame = +1
[HSP Sequence]
```

(SEQ ID NOS 121 AND 122)

```
Query: 174 LPKPYGEVRVDIAFGGNFFAIVPAEQLGIDISVQNLSRLQEAGELLRTEINRSVKVQHPQ 233
           LP PYG+  V I+FGG+FFA++ A QL + +   +LS LQ  G LLR +NR+V VQHPQ
Sbjct:  34 LPHPYGKYAV-ISFGGSFFALIDAAQLQLTVDKGHLSTLQHVGGLLRDTLNRNVSVQHPQ 210

Query: 234 LPHINTVDCVEIYGPPTNPEANYKNVVIFGNRQADRSPCGTGTSAKMATLYAKGQLR    290
           LPHIN +DCVEIY PPTNP A+ KNVVIFGN Q DRSPCGTGT AKMA LYAKG+L+
Sbjct: 211 LPHINRIDCVEIYDPPTNPAASCKNVVIFGNSQVDRSPCGTGTCAKMALLYAKGKLK    381
```

```
SANGER>Tviv380d6.p1k

Score = 156 (395), Expect = 1e-36
Identities = 70/106 (66%), Positives = 88/106 (82%)
```

(SEQ ID NOS 123 AND 124)

```
                                                  I
Query:  67 REIMRFKKSFTCIDMHTEGEAARIVTSGLPHIPGSNMAEKKAYLQENMDYLRRGIMLEPR 161
           R +M+F +  TCIDMHT GE ARIVTSG P+IPG+++ EK+ +LQ +MD++RR +MLEPR
Sbjct:  41 RVVMQFTGTMTCIDMHTAGEPARIVTSGFPNIPGASLVEKRDHLQRHMDHIRRRVMLEPR 100

Query: 127 GHDDMFGAFLFDPIEEGADLGMVFMDTGGYINMCGHNSIAAVTAAV 172
           GHD+MFGAFLF P+ +GAD  ++FMD GGYINMCGHNSIA  TAAV
Sbjct: 101 GHDNMFGAFLFYPLTDGADFSVIFMDAGGYINMCGHNSIAIATAAV 146
```

14. *Vibrio parahaemolyticus*

```
>EM_PRO:AP005077 AP005077.1 Vibro parahaemolyticus DNA, chromosome 1, complete
           sequence, 5/11.
        Length = 299,130

Minus Strand HSPs:

Score = 616 (221.9 bits), Expect = 6.2e-57, P = 6.2e-57
  Identities = 134/357 (37%), Positives = 207/357 (57%), Frame = -2
```

(SEQ ID NOS 125 AND 126)

```
                  I
Query:   66    KREIMRFKKSFTCIDMHTEGEAARIVTSGLPHIPGSNMAEKKAYLQENMDYLRRGIMLEP 125
               K   MR +F CID HT G   R+V G+P + G+ M+EK  Y  E+ D++R+ +M EP
Sbjct: 210923 KERKMR-QGTFFCIDAHTCGNPVRLVAGGVPPLEGNTMSERRQYFLEHYDWIRQALMFEP 210747

Query:  126   RGHDDMFGAFLFDPIEEGADLGMVFMDTGGYLNMCGHNSIAAVTAAVETGIVSVPAKATN 185
              RGH  MG+ +  P + AD  ++F++T G L MCGH +I  VT A+E  ++  P +
Sbjct: 210746 RGHSMMSGSVVLPPCSDNADASILFIETSGCIPMCGHGTIGTVTTAIENRLIT-PKEEGR 210570
```

-continued

```
Query:  186     VPVVLDTPAGLVRGTAHLQSGTESEVSNASIINVPSFLYQQDVVVVLPKPYGEVRVDIAF 245
                +  +LD PAG +      H Q+  + +V++   I NVP++L   QDV V  +  +  GE+ VD+A+
Sbjct: 210569   L--ILDVPAGQIE--VHYQTKGD-KVTSVKIFNVPAYLAHQDVTVEI-EGLGEITVDVAY 210408

Query:  246     GGNFFAIVPAEQLGIDISVQNLSRLQEAGELLRTEINRSVKVQHPQLPHINTVDCVEIYG 305
                GGN++ IV ++    +   +    +         +RT ++++V+   HP  P +  V   V      G
Sbjct: 210407   GGNYYVIVDPQENYAGLEHYSPDEILMLSPKVRTAVSKAVECIHPNDPTVCGVSHVLWTG 210228

Query:  306     PPTNPEANYKNVVIFGNRQADRSPCGTGTSAKMATLYAKGQLRIGETFVYESILGSLFQG 365
                  PT     A   +N V +G++   DRSPCGTGTSA+MA   +AKG+L+ GE FV+ESI+GSLF G
Sbjct: 210227   KPTQEGATARNAVFYGDKALDRSPCGTGTSARMAQWHAKGKLKSGEDFVHESIIGSLFNG 210048

Query:  366     RVLGEERIPGVKVPVTKDAEEGMLVVTAEITGKAFIMGFNTMLFDPTDPFKNGFTLK    422
                R+  G                 +T+      G    +    I G A + G NT+   D  DP+  GF +K
Sbjct: 210047   RIEG----------ITE--VNGQTAILPSIEGWAQVYGHNTIWVDDEDPYAYGFEVK    209913
```

REFERENCES

The following references are incorporated by reference, in their entirety, herein.

1. Lamzin, V. S., Dauter, Z., and Wilson, K. S. (1995) *Curr Opin Struct Biol* 5, 830-836.
2. Kleinkauf, H., and von Dohren, H. (1987) *Annu. Rev. Microbiol.* 41, 259-289
3. Fisher, G. H. (1998) Exs 85, 109-118
4. Nagata, Y., Fujiwara, T., Kawaguchi-Nagata, K., Fukumori, Y., and Yamanaka, T. (1998) *Biochim Biophys Acta* 1379, 76-82.
5. Nagata, Y., Tanaka, K., Iida, T., Kera, Y., Yamada, R., Nakajima, Y., Fujiwara, T., Fukumori, Y., Yamanaka, T., Koga, Y., Tsuji, S., and Kawaguchi-Nagata, K. (1999) *Biochim Biophys Acta* 1435, 160-166.
6. Oguri, S., Kumazaki, M., Kitou, R., Nonoyama, H., and Tooda, N. (1999) *Biochim Biophys Acta* 1472, 107-114.
7. Neidle, A., and Dunlop, D. S. (1990) *Life sci.* 46, 1512-1522
8. Schell, M. J., Molliver, M. E., and Snyder, S. H. (1995) *Proc. Nat. Acad. Sci.* 92, 3948-3952
9. Wolosker, H., Blackshaw, S., and Snyder, S. H. (1999) *Proc Natl Acad Sci USA* 96, 13409-13414.
10. Nagata, Y., Homma, H., Matsumoto, M., and Imai, K. (1999) *FEBS* 454, 317-320
11. Cardinale, G. J., and Abeles, R. H. (1968) *Biochemistry* 7, 3970-3978
12. Rudnick, G., and Abeles, R. H. (1975) *Biochemistry* 14, 4515-4522
13. Reina-San-Martin, B., Degrave, W., Rougeot, C., Cosson, A., Chamond, N., Cordeiro-da-Silva, A., Arala-Chaves, M., and Minoprio, P. (2000) *Nature Medicine* 6, 890-897
14. Cano, M. I., Gruber, A., Vazquez, M., Cortés, A., Levin, M. J., González, A., Degrave, W., Rondinelli, E., Zingales, B., Ramirez, J. L., Alonso, C., Requena, J. M., and Silveira, J. F. d. (1995) *Mol. Bio. Par.* 71, 273-278
15. Higuchi, R., Krummel, B., and Saiki, K. K. (1988) *Nuc. Ac. Res.* 16, 7351-7367
16. Keenan, M. V., and Alworth, W. L. (1974) *Biochem Biophys Res Commun* 57, 500-504.
17. Fisher, L. M., Albery, W. J., and Knowles, J. R. (1986) *Biochemistry* 25, 2529-2537.
18. Albery, W. J., and Knowled, J. R. (1986) *Biochemistry* 25, 2572-2577.
19. Breitbart, R. E., Andreadis, A., and Nadal-Ginard, B. (1987) *Annu. Rev. Biochem.* 56, 467-495
20. Manning-Cela, R., Gonzalez, A., and Swindle, J. (2002) *Infect. Immun.* 70, 4726-4728
21. Krassner, S. M., and Flory, B. (1972) *J. Protozool.* 19, 917-920
22. Bowman, I. B. R., Srivastava, H. K., and Flynn, I. W. (1972) *Adaptation in oxidative metabolism during the transformation of Trypanosoma rhodesiense from bloodstream into culture forms*, Van den Bossche H. Ed. Comparative Biochemistry of parasites, Academic Press, New York
23. Evans, D. A., and Brown, R. C. (1972) *J. Protozool.* 19, 686-690
24. Auerswald, L., Schneider, P., and Gade, G. (1998) *J. Exp. Biol.* 201, 2333-2342
25. Sylvester, D., and Krassner, S. M. (1976) *Comp. Biochem. Physiol.* 55B, 443-447
26. de Isola, E. L., Lammel, E. M., Katzin, V. J., and Gonzalez Cappa, S. M. (1981) *J. Parasitol.* 67, 53-58
27. Contreras, V. T., Salles, J. M., Thomas, N., Morel, C. M., and Goldenberg, S. (1985) *Mol. Biochem. Parasitol.* 16, 315-327
28. Silber, A. M., Tonelli, R. R., Martinelli, M., Colli, W., and Alves, M. J. (2002) *J. Eukaryot. Microbiol.* 49, 441-446
29. Janeway, C. A., and Humphrey, J. H. (1970) *Folia Biol.* 16, 156-172
30. Mozes, E., Kohn, L. D., Hakim, F., and Singer, D. S. (1993) *Science* 261, 91-92
31. Sela, M., and Zisman, E. (1997) *FASEB J.* 11, 449-456
32. Contreras, V. T., Morel, C. M., and Goldenberg, S. (1985) *Mol Biochem Parasitol* 14, 83-96
33. Souto-Padron, T., Reyes, M. B., Leguizamon, S., Campetella, O. E., Frash, A. C., and de Souza, W. (1989) *Eur. J. Cell Biol.* 50, 272-278
34. Janes, B. K., and Bender, R. A. (1998) *J Bacteriol* 180, 563-570.
35. de Jong, M. H., van der Drift, C., and Vogels, G. D. (1975) *J. Bacteriol.* 123, 824-827
36. Shakibaei, M., and Frevert, U. (1996) *J. Exp. Med.* 184, 1699-1711
37. Burleigh, B. A., and Andrews, N. W. (1998) *Cur. Op. Microbiol.* 1, 461-465
38. Gao, W., Wortis, H. H., and Pereira, M. A. (2002) *Internat. Immunol.* 14, 299-308
39. Martin, D., Ault, B., and Nadler, J. V. (1992) *Eur. J. Pharmacol.* 219, 59-66
40. Van Harreveld, A. (1980) *J. Neurobiol.* 11, 519-529

41. Thompson, R. J., Bouwer, H. G., Portnoy, D. A., and Frankel, F. R. (1998) *Infect Immun* 66, 3552-3561.
42. Wolosker, H., Sheth, K. N., Takahashi, M., Mothet, J. P., Brady, R. O., Jr., Ferris, C. D., and Snyder, S. H. (1999) *Proc Natl Acad Sci USA* 96, 721-725.
43. Watanabe, T., Shibata, K., Kera, Y., and Yamada, R. (1998) *Amino Acids* 14, 353-360

[1] GenBank accession number AF195522
[2] GenBank accession number AY140947
[3] EMBL accession number E10199.
[4] The proline racemase/B-cell mitogen of *Trypanosoma cruzi* is a virulence factor whose mRNA is differentially regulated through development by alternative splicing. N. Chamond, N. Coatnoan, J. C. Barale, A. Cosson, A. Berneman, W. Degrave and P. Minoprio. Manuscript in preparation.

BIBLIOGRAPHY RELATED TO THE MICROTEST USING D-AMINO ACID OXIDASE ACCORDING TO THE INVENTION

1. Reina-San-Martin B., Degrave W., Rougeot C., Cosson A., Chamond N., Cordeiro-da-Silva A., Arala-Chaves M. & Minoprio P. (2000) A B-cell mitogen from a pathogenic trypanosome is a eukaryotic proline racemase. *Nature Medicine*, 6, 890.
2. Chamond N., Gregoire C., Coatnoan N., Rougeot C., Freitas-Junior L. H., da Silveira J. F., Degrave W. M. & Minoprio P. (2003) Biochemical characterization of proline racemases from the human protozoan parasite *Trypanosoma cruzi* and definition of putative protein signatures. *J Biol Chem*, 278, 15484.
3. Chamond N., Coatnoan N. & Minoprio P. (2002) Immunotherapy of *Trypanosoma cruzi* infections. *Current Drug Targets*, 2, 247.
4. Rassi A. & Luquetti A. O. (1992) Therapy of Chagas Disease. In: *Chagas Disease (American Trypanosomiasis): its impact on transfusion and clinical medicine* (ed. S. Wendel, Z. Brener, M. E. Camargo & A. Rassi), p. 237. ISBT Brazil' 92-SBHH, Sao Paulo.
5. Cancado J. R. (1999) Criteria of Chagas disease cure. *Mem Inst Oswaldo Cruz*, 94 Suppl 1, 331.
6. Urbina J. A. (2001) Specific treatment of Chagas disease: current status and new developments. *Curr Opin Infect Dis*, 14, 733.
7. Urbina J. A. (2002) Chemotherapy of Chagas disease. *Curr Pharm Des*, 8, 287.
8. Donald, G.& McNeil Jr. (2003) Rare Infection Threatens to Spread in Blood Supply, in New York Times, Nov. 18, 2003
9. Beard, C., Pye, G. Steurer, F. J., Rodriguez, R., Campman, R., Townsend Peterson, A., Ramsey, J., Wirtz, R. A. & Robinson, L. E. Chagas Disease in a Domestic Transmission Cycle, Southern Texas, USA. (2003) Emerging Infectious Diseases, 9, 103.
10. Hamase K., Morikawa A. & Zaitsu K. (2002) D-amino acids in mammals and their diagnostic value. *J Chromatogr B Analyt Technol Biomed Life Sci*, 781, 73.
11. D'Aniello A., Lee J. M., Petrucelli L. & Di Fiore M. M. (1998) Regional decreases of free D-aspartate levels in Alzheimer's disease. *Neurosci Lett*, 250, 131.
12. D'Aniello A., Di Fiore M. M., Fisher G. H., Milone A., Seleni A., D'Aniello S., Perna A. F. & Ingrosso D. (2000) Occurrence of D-aspartic acid and N-methyl-D-aspartic acid in rat neuroendocrine tissues and their role in the modulation of luteinizing hormone and growth hormone release. *FASEB J*, 14, 699.
13. Fisher G. H., D'Aniello A., Vetere A., Padula L., Cusano G. P. & Man E. H. (1991) Free D-aspartate and D-alanine in normal and Alzheimer brain. *Brain Res Bull*, 26, 983.
14. Fisher G. H., Torres D., Bruna J., Cerwinski S., Martin T., Bergljung C., Gruneiro A., Chou S. J., Man E. H. & Pappatheodorou S. (1995) Presence of D-aspartate and D-glutamate in tumor proteins. *Cancer Biochem Biophys*, 15, 79.
15. Fisher G., Lorenzo N., Abe H., Fujita E., Frey W. H., Emory C., Di Fiore M. M. & A D. A. (1998) Free D- and L-amino acids in ventricular cerebrospinal fluid from Alzheimer and normal subjects. *Amino Acids*, 15, 263.
16. Fisher G. H. (1998) Appearance of D-amino acids during aging: D-amino acids in tumor proteins. *Exs*, 85, 109.
17. Nagata Y., Akino T., Ohno K., Kataoka Y., Ueda T., Sakurai T., Shiroshita K. & Yasuda T. (1987) Free D-amino acids in human plasma in relation to senescence and renal diseases. *Clin Sci (Colch)*, 73, 105.
18. Nagata Y., Masui R. & Akino T. (1992) The presence of free D-serine, D-alanine and D-proline in human plasma. *Experientia*, 48, 986.
19. Chouinard M. L., Gaitan D. & Wood P. L. (1993) Presence of the N-methyl-D-aspartate-associated glycine receptor agonist, D-serine, in human temporal cortex: comparison of normal, Parkinson, and Alzheimer tissues. *J Neurochem*, 61, 1561.
20. Kumashiro S., Hashimoto A. & Nishikawa T. (1995) Free D-serine in post-mortem brains and spinal cords of individuals with and without neuropsychiatric diseases. *Brain Res*, 681, 117.
21. Wellner D. and L. A. Lichtenberg, (1968), Assay of Amino acid oxidase, *Methods in Enzymology* XVII, "metabolism of Amino acids ", 593
22. Scannone H., D. Wellner and A. Novogrodsky, (1964), A study of amino acid oxidase specificity, using a new sensitive assay, *Biochemistry*, 3, 1742.
23. Kishimoto M. and Takahashi T., (2001), A spectrophotometric microplate Assay for L-amino acid oxidase, *Analytical Biochemistry*, 298, 136.
24. Wolosker H., Sheth K. N., Takahashi M., Mothet J.-P., Brady R. O. Jr, Ferris, C. D. and Snyder S. H., (1999), Purification of serine racemase: Biosynthesis of the neuromodulator D-Serine, *Proc. Nat. Acad. Sci. USA*, 96, 721

SEQUENCE LISTING

<160> NUMBER OF SEQ ID NOS: 129

<210> SEQ ID NO 1
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (1)
<223> OTHER INFORMATION: Ile, Val, or Leu
<220> FEATURE:
<221> NAME/KEY: MOD_RES
<222> LOCATION: (2)
<223> OTHER INFORMATION: Gly or Asp
<220> FEATURE:
<221> NAME/KEY: MOD_RES
<222> LOCATION: (3)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (8)
<223> OTHER INFORMATION: Glu, Asn, or Met
<220> FEATURE:
<221> NAME/KEY: MOD_RES
<222> LOCATION: (9)..(10)
<223> OTHER INFORMATION: Variable amino acid
<220> FEATURE:
<221> NAME/KEY: MOD_RES
<222> LOCATION: (11)
<223> OTHER INFORMATION: Arg or Asp
<220> FEATURE:
<221> NAME/KEY: MOD_RES
<222> LOCATION: (12)
<223> OTHER INFORMATION: Variable amino acid
<220> FEATURE:
<221> NAME/KEY: MOD_RES
<222> LOCATION: (13)
<223> OTHER INFORMATION: Val or Ile
<220> FEATURE:
<221> NAME/KEY: MOD_RES
<222> LOCATION: (14)
<223> OTHER INFORMATION: Variable amino acid

<400> SEQUENCE: 1

Xaa Xaa Xaa His Xaa Xaa Gly Xaa Xaa Xaa Xaa Xaa Xaa Xaa Gly
 1               5                  10                  15

<210> SEQ ID NO 2
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (1)
<223> OTHER INFORMATION: Asn, Ser, or Met
<220> FEATURE:
<221> NAME/KEY: MOD_RES
<222> LOCATION: (2)
<223> OTHER INFORMATION: Val or Ala
<220> FEATURE:
<221> NAME/KEY: MOD_RES
<222> LOCATION: (3)
<223> OTHER INFORMATION: Glu or Pro
<220> FEATURE:
<221> NAME/KEY: MOD_RES
<222> LOCATION: (4)
<223> OTHER INFORMATION: Ala or Ser
<220> FEATURE:
<221> NAME/KEY: MOD_RES
<222> LOCATION: (5)
<223> OTHER INFORMATION: Phe or Tyr
```

```
<220> FEATURE:
<221> NAME/KEY: MOD_RES
<222> LOCATION: (6)..(19)
<223> OTHER INFORMATION: This region may encompass 13 to 14 variable
      amino acids
<220> FEATURE:
<221> NAME/KEY: MOD_RES
<222> LOCATION: (20)
<223> OTHER INFORMATION: Gly or Lys
<220> FEATURE:
<221> NAME/KEY: MOD_RES
<222> LOCATION: (21)
<223> OTHER INFORMATION: Variable amino acid
<220> FEATURE:
<221> NAME/KEY: MOD_RES
<222> LOCATION: (22)
<223> OTHER INFORMATION: Ile, Val, or Leu
<220> FEATURE:
<221> NAME/KEY: MOD_RES
<222> LOCATION: (23)..(24)
<223> OTHER INFORMATION: Variable amino acid
<220> FEATURE:
<221> NAME/KEY: MOD_RES
<222> LOCATION: (26)
<223> OTHER INFORMATION: Ile or Val
<220> FEATURE:
<221> NAME/KEY: MOD_RES
<222> LOCATION: (27)
<223> OTHER INFORMATION: Ala or Ser
<220> FEATURE:
<221> NAME/KEY: MOD_RES
<222> LOCATION: (28)
<223> OTHER INFORMATION: Tyr, Trp, or Phe
<220> FEATURE:
<221> NAME/KEY: MOD_RES
<222> LOCATION: (31)
<223> OTHER INFORMATION: Variable amino acid
<220> FEATURE:
<221> NAME/KEY: MOD_RES
<222> LOCATION: (32)
<223> OTHER INFORMATION: Phe, Trp, or Tyr

<400> SEQUENCE: 2

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Asp Xaa Xaa Xaa Gly Gly Xaa Xaa
                 20                  25                  30

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (9)..(10)
<223> OTHER INFORMATION: Variable amino acid
<220> FEATURE:
<221> NAME/KEY: MOD_RES
<222> LOCATION: (12)..(13)
<223> OTHER INFORMATION: Variable amino acid

<400> SEQUENCE: 3

Asp Arg Ser Pro Xaa Gly Xaa Gly Xaa Xaa Ala Xaa Xaa Ala
 1               5                  10
```

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic peptide motif
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (9)..(10)
<223> OTHER INFORMATION: Variable amino acid
<220> FEATURE:
<221> NAME/KEY: MOD_RES
<222> LOCATION: (12)..(13)
<223> OTHER INFORMATION: Variable amino acid

<400> SEQUENCE: 4

Asp Arg Ser Pro Cys Gly Xaa Gly Xaa Xaa Ala Xaa Xaa Ala
 1               5                  10

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
ctctcccatg gggcaggaaa agcttctg                                        28

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
ctgagctcga ccagatmtac tgc                                             23

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
gcggatcgct ctccaagcgg gacaggcacc                                      30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
ggtgcctgtc ccgcttggag agcgatccgc                                      30

```
<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggctatttaa atatgtctgg acataactca attgcagcg                    39

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cgctgcaatt gagttatgtc cagacatatt taaatagc                     38

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 11 atg gat acc ggt ggc tat tta aat atg tgt gga cat aac tca att gca      48
Met Asp Thr Gly Gly Tyr Leu Asn Met Cys Gly His Asn Ser Ile Ala
 1               5                  10                  15 gcg                                                                  51
Ala

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Asp Thr Gly Gly Tyr Leu Asn Met Cys Gly His Asn Ser Ile Ala
 1               5                  10                  15

Ala

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggctatttaa atatgtctgg acataactca attgcagcg                    39

<210> SEQ ID NO 14
<211> LENGTH: 51
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 14 atg gat acc ggt ggc tat tta aat atg tct gga cat aac tca att gca      48
Met Asp Thr Gly Gly Tyr Leu Asn Met Ser Gly His Asn Ser Ile Ala
 1               5                  10                  15 gcg                                                                  51
Ala

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atggataccg gtggctattt aaatatgtgt ggacataact caattgcagc g             51

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Asp Thr Gly Gly Tyr Leu Asn Met Ser Gly His Asn Ser Ile Ala
 1               5                  10                  15

Ala

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 17 gtg ata ttt ggc aat cgc cag gcg gat cgc tct cca tgt ggg aca ggc      48
Val Ile Phe Gly Asn Arg Gln Ala Asp Arg Ser Pro Cys Gly Thr Gly
 1               5                  10                  15 acc                                                                  51
Thr

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Val Ile Phe Gly Asn Arg Gln Ala Asp Arg Ser Pro Cys Gly Thr Gly
 1               5                  10                  15

Thr

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcggatcgct ctccaagcgg gacaggcacc                                        30

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtgatatttg gcaatcgcca ggcggatcgc tctccatgtg ggacaggcac c                51

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 21 gtg ata ttt ggc aat cgc cag gcg gat cgc tct cca agc ggg aca ggc       48
Val Ile Phe Gly Asn Arg Gln Ala Asp Arg Ser Pro Ser Gly Thr Gly
 1               5                  10                  15 acc                                                                   51
Thr

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Ile Phe Gly Asn Arg Gln Ala Asp Arg Ser Pro Ser Gly Thr Gly
 1               5                  10                  15

Thr

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (1)
```

```
<223> OTHER INFORMATION: Ile, Val, or Leu
<220> FEATURE:
<221> NAME/KEY: MOD_RES
<222> LOCATION: (2)
<223> OTHER INFORMATION: Gly or Asp
<220> FEATURE:
<221> NAME/KEY: MOD_RES
<222> LOCATION: (3)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (8)
<223> OTHER INFORMATION: Glu, Asn, or Met
<220> FEATURE:
<221> NAME/KEY: MOD_RES
<222> LOCATION: (9)..(10)
<223> OTHER INFORMATION: Variable amino acid
<220> FEATURE:
<221> NAME/KEY: MOD_RES
<222> LOCATION: (11)
<223> OTHER INFORMATION: Arg or Asp
<220> FEATURE:
<221> NAME/KEY: MOD_RES
<222> LOCATION: (12)
<223> OTHER INFORMATION: Variable amino acid
<220> FEATURE:
<221> NAME/KEY: MOD_RES
<222> LOCATION: (13)
<223> OTHER INFORMATION: Val or Ile
<220> FEATURE:
<221> NAME/KEY: MOD_RES
<222> LOCATION: (14)..(15)
<223> OTHER INFORMATION: Variable amino acid

<400> SEQUENCE: 23

Xaa Xaa Xaa His Xaa Xaa Gly Xaa Xaa Xaa Xaa Xaa Xaa Xaa Gly
 1               5                  10                  15

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (8)
<223> OTHER INFORMATION: Gly or Ala
<220> FEATURE:
<221> NAME/KEY: MOD_RES
<222> LOCATION: (9)..(10)
<223> OTHER INFORMATION: Variable amino acid
<220> FEATURE:
<221> NAME/KEY: MOD_RES
<222> LOCATION: (12)..(13)
<223> OTHER INFORMATION: Variable amino acid

<400> SEQUENCE: 24

Asp Arg Ser Pro Xaa Gly Xaa Xaa Xaa Xaa Ala Xaa Xaa Ala
 1               5                  10

<210> SEQ ID NO 25
```

-continued

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Pro Arg Gly His
  1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Pro Arg Gly Ser Asp
  1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Pro Arg Gly Asn Asp
  1               5

<210> SEQ ID NO 28
<211> LENGTH: 1598
<212> TYPE: DNA
<213> ORGANISM: Trypanosoma cruzi

<400> SEQUENCE: 28
cctttttctt tttaaaaaca aaaaaaattc cgggggggaat atggaacagg gtatatgcgt      60
aaaagtgtct gtcccaaaca aaatttttt ttttccgcct tcccattttt tttttttttt     120
tgtgtgtttc ccttgatctc tcgaacaggg caggaaaagc ttctgtttga ccaaaaatat     180
aaaattatta agggcgagaa aaagaaaag aaaaaaaatc aacgagcaaa caggagagaa      240
caccaacaaa aaagggaaat tatgcgattt aagaaatcat tcacatgcat cgacatgcat     300
acggaaggtg aagcagcacg gattgtgacg agtggtttgc cacacattcc aggttcgaat     360
atggcggaga agaaagcata cctgcaggaa acatggatt atttgaggcg tggcataatg      420
ctggaaccac gtggtcatga tgatatgttt ggagcctttt tatttgaccc tattgaagaa     480
ggcgctgact tgggcatggt attcatggat accgttggct atttaaatat gtgtggacat     540
aactcaattg cagcggttac ggcggcagtt gaaacgggaa ttgtgagcgt gccggcgaag     600
gcaacaaatg ttccggttgt cctggacaca ctgcggggt tggtgcgcgg tacggcacac     660
cttcagagtg gtactgagag tgaggtgtca aatgcgagta ttatcaatgt accctcattt     720
ttgtatcagc aggatgtggt ggttgtgttg ccaaagccct atggtgaagt acgggttgat     780
attgcatttg gaggcaattt tttcgccatt gttcccgcgg agcagttggg aattgatatc     840
tccgttcaaa acctctccag gctgcaggag gcaggagaac ttctgcgtac tgaaatcaat     900
cgcagtgtga aggttcagca ccctcagctg ccccatatta acactgtgga ctgtgttgag     960
```

```
atatacggtc cgccaacgaa cccggaggca aactacaaga acgttgtgat atttggcaat    1020
cgccaggcgg atcgctctcc atgtgggaca ggcaccagcg ccaagatggc aacactttat    1080
gccaaaggcc agcttcgcat cggagagact tttgtgtacg agagcatact cggctcactc    1140
ttccagggca gggtacttgg ggaggagcga ataccggggg tgaaggtgcc ggtgaccaaa    1200
gatgccgagg aagggatgct cgttgtaacg gcagaaatta ctggaaaggc ttttatcatg    1260
ggtttcaaca ccatgctgtt tgacccaacg gatccgttta agaacggatt cacattaaag    1320
cagtagatct ggtagagcac agaaactatt ggggaacacg tgcgaacagg tgctgctacg    1380
tgaagggtat tgaatgaatc gtttttttt atttttattt tttattttta ttagtgcatt    1440
attattaaat ttttttttg ttttggggtt caacggtac cgcgttggga cagggaagc    1500 gatagcggcc ggacaatttt ttgcttttat tttcattttc atcttcctac ccaaccccct    1560
tggttccacc ggtcgcggcg gggtcttgtg ggtggagg                            1598
```

<210> SEQ ID NO 29
<211> LENGTH: 1582
<212> TYPE: DNA
<213> ORGANISM: Trypanosoma cruzi

<400> SEQUENCE: 29

```
gtgtgttcaa cagttttgtt tcctttttc tcttttctc tttccatcat acatacatac      60
atacatacat atatatatct gcgtagatat gcacatgcgt atatgcgtga agagtgtctg    120
tcccaacatt tttttttttt ttttgtgtgt tttcccttga ttcccgaacg ggcaggaaaa    180
gcttctgttt gaccaaaaat ataaaattat taagggcgag aaaagaaaaa aaaaatcaac    240
cgaggagaca acaccaacaa aaagggaaa ttatgcgatt taagaaatca ttgacatgca    300
tcgacatgca tacggaaggt gaagcagcac ggattgtgac gagtggtttg ccacacattc    360
caggttcgaa tatggcggag aagaaagcat acctgcagga aaacatggat tatttgaggc    420
gtggcataat gctggagcca cgtggtcatg atgatatgtt tggagccttt ttatttgacc    480
ctattgaaga aggcgctgac ttgggcatcg tattcatgga taccggtggc tatttaaata    540
tgtgtggaca taactcaatt gcagcggtta cggcggcagt ggaaacggga attttgagcg    600
tgccggcgaa ggcaacaaat gttccggttg tcctggacac acctgcgggg ttggtgcgcg    660
gtacggcaca ccttcagagt ggtactgaga gtgaggtgtc aaatgcgagt attatcaatg    720
tgccctcatt tttgtatcag caggatgtgg tgattgtttt gccaaagccc tatggtgagg    780
tacgggttga tattgcattt ggaggcaatt ttttcgccat tgttcccgcg gagcacttgg    840
gaattgatat ctccgttcaa aacctctcca ggctgcagga ggcaggagaa cttctgcgta    900
ctgaaatcaa tcgcagtgtg aaggttcagc accctcagct gccccatatt aacactgtgg    960
actgtgttga gatatacggt ccgccaacga acccggaggc aaaatacaag aacgttgtga   1020
tatttggcaa tcgccaggcg gatcgctctc catgtgggac aggcaccagc gccaagatgg   1080
caacacttta tgccaaaggc cagcttcgca tcggagagac ttttgtgtac gagagcatac   1140
tcggctcact cttccagggc agggtacttg gggaggagcg aataccgggg gtgaaggtgc   1200
cggtgaccaa agatgccgag gaagggatgc tcgttgtaac gacagaaatt actggaaagg   1260
cttttatcat gggtttcaac accatgctgt ttgacccaac ggatccgttc ttaaacggat   1320
tcacactaaa gcggtagatc tggtagagca cagaaactat ggggaacac gtgcgaacag   1380 gtgctgctac gtaaagggta ttgaatgaat cgttttttt tttttttttt tattagtgca   1440
```

```
ttattttttt ttttttttgt tttggggttt caacggtacc acgttgggag cagggaaacg      1500
atagcggccg gacaattttt tacttttatt ttcattttca ccttcctacc caacccctt      1560 ggttccaccg tcgcggcgg gg                                                1582
```

```
<210> SEQ ID NO 30
<211> LENGTH: 423
<212> TYPE: PRT
<213> ORGANISM: Trypanosoma cruzi

<400> SEQUENCE: 30
```

```
Met Arg Lys Ser Val Cys Pro Lys Gln Lys Phe Phe Ser Ala Phe
 1               5                  10                  15

Pro Phe Phe Phe Phe Cys Val Phe Pro Leu Ile Ser Arg Thr Gly
            20                  25                  30

Gln Glu Lys Leu Leu Phe Asp Gln Lys Tyr Lys Ile Ile Lys Gly Glu
        35                  40                  45

Lys Lys Glu Lys Lys Asn Gln Arg Ala Asn Arg Arg Glu His Gln
    50                  55                  60

Gln Lys Arg Glu Ile Met Arg Phe Lys Lys Ser Phe Thr Cys Ile Asp
65                  70                  75                  80

Met His Thr Glu Gly Glu Ala Ala Arg Ile Val Thr Ser Gly Leu Pro
                85                  90                  95

His Ile Pro Gly Ser Asn Met Ala Glu Lys Lys Ala Tyr Leu Gln Glu
            100                 105                 110

Asn Met Asp Tyr Leu Arg Arg Gly Ile Met Leu Glu Pro Arg Gly His
        115                 120                 125

Asp Asp Met Phe Gly Ala Phe Leu Phe Asp Pro Ile Glu Glu Gly Ala
130                 135                 140

Asp Leu Gly Met Val Phe Met Asp Thr Gly Gly Tyr Leu Asn Met Cys
145                 150                 155                 160

Gly His Asn Ser Ile Ala Ala Val Thr Ala Val Glu Thr Gly Ile
                165                 170                 175

Val Ser Val Pro Ala Lys Ala Thr Asn Val Pro Val Leu Asp Thr
            180                 185                 190

Pro Ala Gly Leu Val Arg Gly Thr Ala His Leu Gln Ser Gly Thr Glu
        195                 200                 205

Ser Glu Val Ser Asn Ala Ser Ile Ile Asn Val Pro Ser Phe Leu Tyr
    210                 215                 220

Gln Gln Asp Val Val Val Leu Pro Lys Pro Tyr Gly Glu Val Arg
225                 230                 235                 240

Val Asp Ile Ala Phe Gly Gly Asn Phe Phe Ala Ile Val Pro Ala Glu
                245                 250                 255

Gln Leu Gly Ile Asp Ile Ser Val Gln Asn Leu Ser Arg Leu Gln Glu
            260                 265                 270

Ala Gly Glu Leu Leu Arg Thr Glu Ile Asn Arg Ser Val Lys Val Gln
        275                 280                 285

His Pro Gln Leu Pro His Ile Asn Thr Val Asp Cys Val Glu Ile Tyr
    290                 295                 300

Gly Pro Pro Thr Asn Pro Glu Ala Asn Tyr Lys Asn Val Val Ile Phe
305                 310                 315                 320

Gly Asn Arg Gln Ala Asp Arg Ser Pro Cys Gly Thr Gly Thr Ser Ala
                325                 330                 335

Lys Met Ala Thr Leu Tyr Ala Lys Gly Gln Leu Arg Ile Gly Glu Thr
            340                 345                 350
```

```
Phe Val Tyr Glu Ser Ile Leu Gly Ser Leu Phe Gln Gly Arg Val Leu
            355                 360                 365

Gly Glu Glu Arg Ile Pro Gly Val Lys Val Pro Val Thr Lys Asp Ala
    370                 375                 380

Glu Glu Gly Met Leu Val Val Thr Ala Glu Ile Thr Gly Lys Ala Phe
385                 390                 395                 400

Ile Met Gly Phe Asn Thr Met Leu Phe Asp Pro Thr Asp Pro Phe Lys
                405                 410                 415

Asn Gly Phe Thr Leu Lys Gln
            420

<210> SEQ ID NO 31
<211> LENGTH: 354
<212> TYPE: PRT
<213> ORGANISM: Trypanosoma cruzi

<400> SEQUENCE: 31

Met Arg Phe Lys Lys Ser Leu Thr Cys Ile Asp Met His Thr Glu Gly
 1               5                  10                  15

Glu Ala Ala Arg Ile Val Thr Ser Gly Leu Pro His Ile Pro Gly Ser
            20                  25                  30

Asn Met Ala Glu Lys Lys Ala Tyr Leu Gln Glu Asn Met Asp Tyr Leu
        35                  40                  45

Arg Arg Gly Ile Met Leu Glu Pro Arg Gly His Asp Asp Met Phe Gly
    50                  55                  60

Ala Phe Leu Phe Asp Pro Ile Glu Glu Gly Ala Asp Leu Gly Ile Val
65                  70                  75                  80

Phe Met Asp Thr Gly Gly Tyr Leu Asn Met Cys Gly His Asn Ser Ile
                85                  90                  95

Ala Ala Val Thr Ala Ala Val Glu Thr Gly Ile Leu Ser Val Pro Ala
            100                 105                 110

Lys Ala Thr Asn Val Pro Val Val Leu Asp Thr Pro Ala Gly Leu Val
        115                 120                 125

Arg Gly Thr Ala His Leu Gln Ser Gly Thr Glu Ser Glu Val Ser Asn
    130                 135                 140

Ala Ser Ile Ile Asn Val Pro Ser Phe Leu Tyr Gln Gln Asp Val Val
145                 150                 155                 160

Ile Val Leu Pro Lys Pro Tyr Gly Glu Val Arg Val Asp Ile Ala Phe
                165                 170                 175

Gly Gly Asn Phe Phe Ala Ile Val Pro Ala Glu His Leu Gly Ile Asp
            180                 185                 190

Ile Ser Val Gln Asn Leu Ser Arg Leu Gln Glu Ala Gly Glu Leu Leu
        195                 200                 205

Arg Thr Glu Ile Asn Arg Ser Val Lys Val Gln His Pro Gln Leu Pro
    210                 215                 220

His Ile Asn Thr Val Asp Cys Val Glu Ile Tyr Gly Asn Ala Thr Asn
225                 230                 235                 240

Pro Glu Ala Lys Tyr Lys Asn Val Val Ile Phe Gly Asn Arg Gln Ala
                245                 250                 255

Asp Arg Ser Pro Cys Gly Thr Gly Thr Ser Ala Lys Met Ala Thr Leu
            260                 265                 270

Tyr Ala Lys Gly Gln Leu Arg Ile Gly Glu Thr Phe Val Tyr Glu Ser
        275                 280                 285

Ile Leu Gly Ser Leu Phe Gln Gly Arg Val Leu Gly Glu Glu Arg Ile
```

-continued

```
                290                 295                 300
Pro Gly Val Lys Val Pro Val Thr Lys Asp Ala Glu Glu Gly Met Leu
305                 310                 315                 320

Val Val Thr Thr Glu Ile Thr Gly Lys Ala Phe Ile Met Gly Phe Asn
                325                 330                 335

Thr Met Leu Phe Asp Pro Thr Asp Pro Phe Leu Asn Gly Phe Thr Leu
                340                 345                 350

Lys Arg

<210> SEQ ID NO 32
<211> LENGTH: 335
<212> TYPE: PRT
<213> ORGANISM: Clostridium sticklandii

<400> SEQUENCE: 32

Met Lys Phe Ser Lys Gly Ile His Ala Ile Asp Ser His Thr Met Gly
  1               5                  10                  15

Glu Pro Thr Arg Ile Val Gly Gly Ile Pro Gln Ile Asn Gly Glu
                 20                  25                  30

Thr Met Ala Asp Lys Lys Tyr Leu Glu Asp Asn Leu Asp Tyr Val
                 35                  40                  45

Arg Thr Ala Leu Met His Glu Pro Arg Gly His Asn Asp Met Phe Gly
             50                  55                  60

Ser Ile Ile Thr Ser Asn Asn Lys Glu Ala Asp Phe Gly Ile Ile
 65                  70                  75                  80

Phe Met Asp Gly Gly Tyr Leu Asn Met Cys Gly His Gly Ser Ile
                 85                  90                  95

Gly Ala Ala Thr Val Ala Val Glu Thr Gly Met Val Glu Met Val Glu
                100                 105                 110

Pro Val Thr Asn Ile Asn Met Glu Ala Pro Ala Gly Leu Ile Lys Ala
                115                 120                 125

Lys Val Met Val Glu Asn Glu Lys Val Lys Glu Val Ser Ile Thr Asn
                130                 135                 140

Val Pro Ser Phe Leu Tyr Met Glu Asp Ala Lys Leu Glu Val Pro Ser
145                 150                 155                 160

Leu Asn Lys Thr Ile Thr Phe Asp Ile Ser Phe Gly Gly Ser Phe Phe
                165                 170                 175

Ala Ile Ile His Ala Lys Glu Leu Gly Val Lys Val Glu Thr Ser Gln
                180                 185                 190

Val Asp Val Leu Lys Lys Leu Gly Ile Glu Ile Arg Asp Leu Ile Asn
                195                 200                 205

Glu Lys Ile Lys Val Gln His Pro Glu Leu Glu His Ile Lys Thr Val
                210                 215                 220

Asp Leu Val Glu Ile Tyr Asp Glu Pro Ser Asn Pro Glu Ala Thr Tyr
225                 230                 235                 240

Lys Asn Val Val Ile Phe Gly Gln Gly Gln Val Asp Arg Ser Pro Cys
                245                 250                 255

Gly Thr Gly Thr Ser Ala Lys Leu Ala Thr Leu Tyr Lys Lys Gly His
                260                 265                 270

Leu Lys Ile Asp Glu Lys Phe Val Tyr Glu Ser Ile Thr Gly Thr Met
                275                 280                 285

Phe Lys Gly Arg Val Leu Glu Glu Thr Lys Val Gly Glu Phe Asp Ala
                290                 295                 300

Ile Ile Pro Glu Ile Thr Gly Gly Ala Tyr Ile Thr Gly Phe Asn His
```

```
305                 310                 315                 320
Phe Val Ile Asp Pro Glu Asp Pro Leu Lys Tyr Gly Phe Thr Val
                325                 330                 335

<210> SEQ ID NO 33
<211> LENGTH: 354
<212> TYPE: PRT
<213> ORGANISM: Homo sapiens

<400> SEQUENCE: 33

Met Glu Ser Ala Leu Ala Val Pro Trp Leu Pro Pro His Asp Pro Gly
  1               5                  10                  15

Thr Pro Val Leu Ser Val Val Asp Met His Thr Gly Gly Glu Pro Leu
                 20                  25                  30

Arg Ile Val Leu Ala Gly Cys Pro Glu Val Ser Gly Pro Thr Leu Leu
             35                  40                  45

Ala Lys Arg Arg Tyr Met Arg Gln His Leu Asp His Val Arg Arg Arg
         50                  55                  60

Leu Met Phe Glu Pro Arg Gly His Arg Asp Met Tyr Gly Ala Val Leu
 65                  70                  75                  80

Val Pro Ser Glu Leu Pro Asp Ala His Leu Gly Val Leu Phe Leu His
                 85                  90                  95

Asn Glu Gly Tyr Ser Ser Met Cys Gly His Ala Val Leu Ala Leu Gly
                100                 105                 110

Arg Phe Ala Leu Asp Phe Gly Leu Val Pro Ala Pro Ala Gly Thr
            115                 120                 125

Arg Glu Ala Arg Val Asn Ile His Cys Pro Cys Gly Leu Val Thr Ala
        130                 135                 140

Phe Val Ala Cys Glu Asp Gly Arg Ser His Gly Pro Val Arg Phe His
145                 150                 155                 160

Ser Val Pro Ala Phe Val Leu Ala Thr Asp Leu Met Val Asp Val Pro
                165                 170                 175

Gly His Gly Lys Val Met Val Asp Ile Ala Tyr Gly Gly Ala Phe Tyr
            180                 185                 190

Ala Phe Val Thr Ala Glu Lys Leu Gly Leu Asp Ile Cys Ser Ala Lys
        195                 200                 205

Thr Arg Asp Leu Val Asp Ala Ala Ser Ala Val Thr Glu Ala Val Lys
210                 215                 220

Ala Gln Phe Lys Ile Asn His Pro Asp Ser Glu Asp Leu Ala Phe Leu
225                 230                 235                 240

Tyr Gly Thr Ile Leu Thr Asp Gly Lys Asp Ala Tyr Thr Lys Glu Pro
                245                 250                 255

Thr Thr Asn Ile Cys Val Phe Ala Asp Glu Gln Val Asp Arg Ser Pro
            260                 265                 270

Thr Gly Ser Gly Val Thr Ala Arg Ile Ala Leu Gln Tyr His Lys Gly
        275                 280                 285

Leu Leu Glu Leu Asn Gln Met Arg Ala Phe Lys Ser Ser Ala Thr Gly
        290                 295                 300

Ser Val Phe Thr Gly Lys Ala Val Arg Glu Ala Lys Cys Gly Asp Phe
305                 310                 315                 320

Lys Ala Val Ile Val Glu Val Ser Gly Gln Ala His Tyr Thr Gly Thr
                325                 330                 335

Ala Ser Phe Ile Ile Glu Asp Asp Pro Leu Arg Asp Gly Phe Leu
            340                 345                 350
```

Leu Lys

<210> SEQ ID NO 34
<211> LENGTH: 354
<212> TYPE: PRT
<213> ORGANISM: Homo sapiens

<400> SEQUENCE: 34

```
Met Glu Ser Ala Leu Ala Val Pro Arg Leu Pro Pro His Asp Pro Gly
  1               5                  10                  15

Thr Pro Val Leu Ser Val Val Asp Met His Thr Gly Gly Glu Pro Leu
             20                  25                  30

Arg Ile Val Leu Ala Gly Cys Pro Glu Val Ser Gly Pro Thr Leu Leu
         35                  40                  45

Ala Lys Arg Arg Tyr Met Arg Gln His Leu Asp His Val Arg Arg Arg
     50                  55                  60

Leu Met Phe Glu Pro Arg Gly His Arg Asp Met Tyr Gly Ala Val Leu
 65                  70                  75                  80

Val Pro Ser Glu Leu Pro Asp Ala His Leu Gly Val Leu Phe Leu His
                 85                  90                  95

Asn Glu Gly Tyr Ser Ser Met Cys Gly His Ala Val Leu Ala Leu Gly
            100                 105                 110

Arg Phe Ala Leu Asp Phe Gly Leu Val Pro Ala Pro Ala Gly Thr
        115                 120                 125

Arg Glu Ala Arg Val Asn Ile His Cys Pro Cys Gly Leu Val Thr Ala
    130                 135                 140

Phe Val Ala Cys Glu Asp Gly Arg Ser His Gly Pro Val Arg Phe His
145                 150                 155                 160

Ser Val Pro Ala Phe Val Leu Ala Thr Asp Leu Met Val Asp Val Pro
                165                 170                 175

Gly His Gly Lys Val Met Val Asp Ile Ala Tyr Gly Gly Ala Phe Tyr
            180                 185                 190

Ala Phe Val Thr Ala Glu Lys Leu Gly Leu Asp Ile Cys Ser Ala Lys
        195                 200                 205

Thr Arg Asp Leu Val Asp Ala Ala Ser Ala Val Thr Glu Ala Val Lys
    210                 215                 220

Ala Gln Phe Lys Ile Asn His Pro Asp Ser Glu Asp Leu Ala Phe Leu
225                 230                 235                 240

Tyr Gly Thr Ile Leu Thr Asp Gly Lys Asp Ala Tyr Thr Lys Glu Pro
                245                 250                 255

Thr Thr Asn Ile Cys Val Phe Ala Asp Glu Gln Val Asp Arg Ser Pro
            260                 265                 270

Thr Gly Ser Gly Val Thr Ala Arg Ile Ala Leu Gln Tyr His Lys Gly
        275                 280                 285

Leu Leu Glu Leu Asn Gln Met Arg Ala Phe Lys Ser Ser Ala Thr Gly
    290                 295                 300

Ser Val Phe Thr Gly Lys Ala Val Arg Glu Ala Lys Cys Gly Asp Phe
305                 310                 315                 320

Lys Ala Val Ile Val Glu Val Ser Gly Gln Ala His Tyr Thr Gly Thr
                325                 330                 335

Ala Ser Phe Ile Ile Glu Asp Asp Pro Leu Arg Asp Gly Phe Leu
            340                 345                 350

Leu Lys
```

<210> SEQ ID NO 35
<211> LENGTH: 354
<212> TYPE: PRT
<213> ORGANISM: Mus musculus

<400> SEQUENCE: 35

Met Glu Ala Ala Leu Ala Val Thr Arg Leu Pro Pro Asn Asp Pro Arg
1               5                   10                  15

Thr Pro Ala Leu Ser Val Val Asp Met His Thr Gly Gly Glu Pro Leu
            20                  25                  30

Arg Ile Val His Ala Gly Cys Pro Glu Val Ala Gly Pro Thr Leu Leu
        35                  40                  45

Ala Lys Arg Arg Tyr Met Arg Gln His Leu Asp Tyr Ile Arg Arg Arg
    50                  55                  60

Leu Val Phe Glu Pro Arg Gly His Arg Asp Met Tyr Gly Ala Ile Leu
65                  70                  75                  80

Val Pro Ser Glu Leu Pro Asp Ala His Leu Gly Val Leu Phe Leu His
                85                  90                  95

Asn Glu Gly Tyr Ser Ser Met Cys Gly His Ala Val Leu Ala Leu Gly
            100                 105                 110

Arg Phe Ala Leu Asp Phe Gly Leu Val Pro Ala Pro Pro Lys Gly Ala
        115                 120                 125

Arg Glu Ala Gln Val Asn Ile His Cys Pro Cys Gly Leu Val Thr Ala
    130                 135                 140

Phe Val Glu Cys Glu Gly Gly Arg Ser Cys Gly Pro Val Arg Phe His
145                 150                 155                 160

Ser Val Pro Ala Phe Val Leu Ala Ser Asp Leu Thr Val Asp Val Pro
                165                 170                 175

Gly His Gly Lys Val Leu Val Asp Ile Ala Tyr Gly Gly Ala Phe Tyr
            180                 185                 190

Ala Phe Val Ser Ala Glu Lys Leu Gly Leu Asp Val Cys Ser Ala Lys
        195                 200                 205

Thr Arg Asp Leu Val Asp Ala Ala Ser Ala Leu Thr Gly Ala Val Lys
    210                 215                 220

Ala Gln Phe Lys Ile Asn His Pro Glu Ser Glu Asp Leu Gly Phe Leu
225                 230                 235                 240

Tyr Gly Ser Ile Leu Thr Asp Gly Lys Asp Ala Tyr Ser Glu Glu Ala
                245                 250                 255

Thr Thr Asn Ile Cys Val Phe Ala Asp Glu Gln Val Asp Arg Ser Pro
            260                 265                 270

Thr Gly Ser Gly Val Thr Ala Arg Ile Ala Leu Gln Tyr His Lys Gly
        275                 280                 285

Leu Leu Gln Leu Asn Gln Thr Arg Ala Phe Lys Ser Ser Ala Thr Gly
    290                 295                 300

Ser Val Phe Thr Gly Cys Ala Val Arg Glu Ala Lys Cys Gly Asp Phe
305                 310                 315                 320

Lys Ala Val Ile Val Glu Val Ala Gly Gln Ala His Tyr Thr Gly Thr
                325                 330                 335

Ala Asn Leu Thr Val Glu Asp Gly Asp Pro Leu Arg Asp Gly Phe Leu
            340                 345                 350

Leu Lys

<210> SEQ ID NO 36
<211> LENGTH: 354
<212> TYPE: PRT

<213> ORGANISM: Mus musculus

<400> SEQUENCE: 36

Met Glu Ala Ala Leu Ala Val Thr Arg Leu Pro Pro His Asp Ser Arg
 1               5                  10                  15

Thr Pro Ala Leu Ser Val Val Asp Met His Thr Gly Gly Glu Pro Leu
             20                  25                  30

Arg Ile Val His Ala Gly Cys Pro Glu Val Ala Gly Pro Thr Leu Leu
         35                  40                  45

Ala Lys Arg Arg Tyr Met Arg Gln His Leu Asp Tyr Ile Arg Arg Arg
     50                  55                  60

Leu Val Phe Glu Pro Arg Gly His Arg Asp Met Tyr Gly Ala Ile Leu
 65                  70                  75                  80

Met Pro Ser Glu Leu Pro Asp Ala His Leu Gly Val Leu Phe Leu His
                 85                  90                  95

Asn Glu Gly Tyr Ser Ser Met Cys Gly His Ala Val Leu Ala Leu Gly
            100                 105                 110

Arg Phe Ala Leu Asp Phe Gly Leu Val Pro Ala Pro Pro Glu Gly Ala
        115                 120                 125

Arg Glu Ala Gln Val Asn Ile His Cys Pro Cys Gly Leu Val Thr Ala
    130                 135                 140

Phe Val Glu Cys Glu Gly Gly Arg Ser Cys Gly Pro Val Arg Phe His
145                 150                 155                 160

Ser Val Pro Ala Phe Val Leu Ala Ser Asp Leu Thr Val Asp Val Pro
                165                 170                 175

Gly His Gly Lys Val Leu Val Asp Ile Ala Tyr Gly Gly Ala Phe Tyr
            180                 185                 190

Ala Phe Val Ser Ala Glu Lys Leu Gly Leu Asp Val Cys Ser Ala Lys
        195                 200                 205

Thr Arg Asp Leu Val Asp Ala Ala Ser Ala Leu Thr Gly Ala Val Lys
    210                 215                 220

Ala Gln Phe Lys Ile Asn His Pro Glu Ser Glu Asp Leu Gly Phe Leu
225                 230                 235                 240

Tyr Gly Ser Ile Leu Thr Asp Gly Lys Asp Ala Tyr Ser Glu Glu Ala
                245                 250                 255

Thr Thr Asn Ile Cys Val Phe Ala Asp Glu Gln Val Asp Arg Ser Pro
            260                 265                 270

Thr Gly Ser Gly Val Thr Ala Arg Ile Ala Leu Gln Tyr His Lys Gly
        275                 280                 285

Leu Leu Gln Leu Asn Gln Thr Arg Ala Phe Lys Ser Ser Ala Thr Gly
    290                 295                 300

Ser Val Phe Thr Gly Cys Ala Val Arg Glu Ala Lys Cys Gly Asp Phe
305                 310                 315                 320

Lys Ala Val Ile Val Glu Val Ala Gly Gln Ala His Tyr Thr Gly Thr
                325                 330                 335

Ala Asn Leu Thr Val Glu Asp Gly Asp Pro Leu Arg Asp Gly Phe Leu
            340                 345                 350

Leu Lys

<210> SEQ ID NO 37
<211> LENGTH: 333
<212> TYPE: PRT
<213> ORGANISM: Rhizobium loti

<400> SEQUENCE: 37

Met Ala Lys Lys Ser Phe Phe Cys Ile Asp Gly His Thr Cys Gly Asn
1               5                   10                  15

Pro Val Arg Leu Val Ala Gly Gly Pro Leu Leu Glu Gly Ser Thr
            20                  25                  30

Met Met Glu Arg Arg Ala His Phe Leu Ala Glu Tyr Asp Trp Ile Arg
            35                  40                  45

Thr Gly Leu Met Phe Glu Pro Arg Gly His Asp Val Met Ser Gly Ser
        50                  55                  60

Ile Leu Tyr Pro Pro Thr Arg Glu Asp Cys Asp Ile Ala Ile Leu Phe
65                  70                  75                  80

Ile Glu Thr Ser Gly Cys Leu Pro Met Cys Gly His Gly Thr Ile Gly
                85                  90                  95

Thr Val Thr Met Ala Ile Glu His Gly Leu Ile Lys Pro Lys Thr Pro
                100                 105                 110

Gly Val Leu Arg Leu Asp Thr Pro Ala Gly Leu Val Ile Ala Glu Tyr
            115                 120                 125

Lys Gln Val Gly Glu Tyr Val Glu Glu Val Arg Ile Thr Asn Val Pro
130                 135                 140

Ser Phe Leu His Ala Glu Gly Leu Thr Val Glu Cys Pro Gly Leu Gly
145                 150                 155                 160

Glu Ile Thr Val Asp Val Ala Tyr Gly Gly Asn Phe Tyr Ala Ile Val
                165                 170                 175

Glu Pro Gln Glu Asn Tyr Arg Asp Met Ala Asp His Ser Ala Gly Asp
            180                 185                 190

Leu Ile Ala Trp Ser Pro Val Val Arg Gln Arg Leu Asn Glu Lys Tyr
        195                 200                 205

Ser Phe Val His Pro Glu Asn Pro Gly Ile Asn Arg Leu Ser His Met
            210                 215                 220

Leu Trp Thr Gly Lys Pro Thr Val Glu Gly Ala Asp Ala Arg Asn Ala
225                 230                 235                 240

Val Phe Tyr Gly Asp Lys Ala Ile Asp Arg Ser Pro Cys Gly Thr Gly
                245                 250                 255

Thr Ser Ala Arg Met Ala Gln Leu His Ala Lys Gly Lys Leu Lys Ala
            260                 265                 270

Gly Asp Ala Phe Val His Glu Ser Ile Ile Gly Ser Leu Phe Lys Gly
        275                 280                 285

Lys Val Glu Lys Glu Val Thr Val Ala Gly Lys Pro Ala Ile Ile Pro
290                 295                 300

Ser Ile Gly Gly Trp Ala Arg Leu Thr Gly Leu Asn Thr Ile Phe Ile
305                 310                 315                 320

Asp Asp Arg Asp Pro Phe Ala His Gly Phe Val Thr
            325                 330

<210> SEQ ID NO 38
<211> LENGTH: 333
<212> TYPE: PRT
<213> ORGANISM: Brucella melitensis

<400> SEQUENCE: 38

Met Ala Arg His Ser Phe Phe Cys Val Asp Gly His Thr Cys Gly Asn
1               5                   10                  15

Pro Val Arg Leu Val Ala Gly Gly Pro Asn Leu Asn Gly Ser Thr
            20                  25                  30

Met Met Glu Lys Cys Ala His Phe Leu Ala Glu Tyr Asp Trp Ile Arg

```
                  35                  40                  45
Thr Gly Leu Met Phe Glu Pro Arg Gly His Asp Met Met Ser Gly Ser
         50                  55                  60
Ile Leu Tyr Pro Pro Thr Arg Pro Asp Cys Asp Val Ala Val Leu Phe
 65                  70                  75                  80
Ile Glu Thr Ser Gly Cys Leu Pro Met Cys Gly His Gly Thr Ile Gly
                 85                  90                  95
Thr Val Thr Met Ala Ile Glu Gln Gly Leu Val Thr Pro Lys Thr Pro
                100                 105                 110
Gly Lys Leu Asn Leu Asp Thr Pro Ala Gly Leu Val Ala Ile Glu Tyr
            115                 120                 125
Glu Gln Asp Gly Gln Tyr Val Glu Arg Val Arg Leu Thr Asn Val Pro
        130                 135                 140
Ala Phe Leu Tyr Ala Glu Gly Leu Glu Val Glu Cys Pro Asp Leu Gly
145                 150                 155                 160
Pro Ile Lys Val Asp Val Ala Tyr Gly Gly Asn Phe Tyr Ala Ile Val
                165                 170                 175
Glu Pro Gln Glu Asn Tyr Thr Asp Met Asp Asp Tyr Ser Ala Leu Gln
            180                 185                 190
Leu Ile Ala Trp Ser Pro Val Leu Arg Gln Arg Leu Asn Glu Lys Tyr
        195                 200                 205
Lys Phe Gln His Pro Glu Leu Pro Asp Ile Asn Arg Leu Ser His Ile
    210                 215                 220
Leu Trp Thr Gly Lys Pro Lys His Pro Gln Ala His Ala Arg Asn Ala
225                 230                 235                 240
Val Phe Tyr Gly Asp Lys Ala Ile Asp Arg Ser Pro Cys Gly Thr Gly
                245                 250                 255
Thr Ser Ala Arg Met Ala Gln Leu Ala Ala Lys Gly Lys Leu Lys Pro
            260                 265                 270
Gly Asp Glu Phe Ile His Glu Ser Ile Ile Gly Ser Leu Phe His Gly
        275                 280                 285
Arg Val Glu Arg Ala Ala Glu Val Ala Gly Arg Pro Ala Ile Val Pro
    290                 295                 300
Ser Ile Ala Gly Trp Ala Arg Met Thr Gly Tyr Asn Thr Ile Phe Ile
305                 310                 315                 320
Asp Asp Arg Asp Pro Phe Ala His Gly Phe Ser Ala Ala
                325                 330

<210> SEQ ID NO 39
<211> LENGTH: 333
<212> TYPE: PRT
<213> ORGANISM: Rhizobium meliloti

<400> SEQUENCE: 39

Met Ala Thr His Thr Phe Ser Cys Ile Asp Gly His Thr Cys Gly Asn
  1               5                  10                  15
Pro Val Arg Leu Val Ser Gly Gly Pro Arg Leu Glu Gly Ala Asn
             20                  25                  30
Met Leu Glu Lys Arg Ala His Phe Leu Lys Glu Phe Asp Trp Ile Arg
         35                  40                  45
Thr Gly Leu Met Phe Glu Pro Arg Gly His Asp Met Met Ser Gly Ser
     50                  55                  60
Ile Leu Tyr Pro Pro Thr Arg Pro Asp Cys Asp Val Ala Val Leu Phe
 65                  70                  75                  80
```

```
Ile Glu Thr Ser Gly Cys Leu Pro Met Cys Gly His Gly Thr Ile Gly
                85                  90                  95

Thr Ile Thr Met Gly Ile Glu Asn Gly Leu Ile Thr Pro Arg Glu Pro
            100                 105                 110

Gly Lys Leu Ser Ile Asp Ala Pro Ala Gly Lys Val Asp Ile Thr Tyr
        115                 120                 125

Arg Gln Glu Gly Arg Phe Val Glu Val Arg Leu Thr Asn Val Pro
    130                 135                 140

Ser Phe Leu Tyr Ala Glu Gly Leu Ala Ala Glu Val Glu Gly Leu Gly
145                 150                 155                 160

Glu Ile Val Val Asp Val Ala Tyr Gly Gly Asn Phe Tyr Ala Ile Val
                165                 170                 175

Glu Pro Gln Lys Asn Phe Arg Asp Met Ala Asp His Thr Ala Gly Glu
            180                 185                 190

Leu Val Gly Trp Ser Pro Lys Leu Arg Ala Ala Leu Asn Ala Lys Tyr
        195                 200                 205

Glu Phe Val His Pro Glu His Pro Glu Ile Arg Gly Leu Ser His Ile
    210                 215                 220

Gln Trp Thr Gly Lys Pro Thr Gln Pro Glu Ala His Ala Arg Asn Ala
225                 230                 235                 240

Val Phe Tyr Gly Glu Lys Ala Ile Asp Arg Ser Pro Cys Gly Thr Gly
                245                 250                 255

Thr Ser Ala Arg Ile Ala Gln Leu Ala Ala Lys Gly Lys Leu Lys Val
            260                 265                 270

Gly Asp Glu Phe Val His Glu Ser Ile Ile Gly Ser Leu Phe Lys Gly
        275                 280                 285

Arg Val Glu Ala Ala Lys Val Ala Asp Arg Asp Ala Ile Ile Pro
    290                 295                 300

Ser Ile Ala Gly Trp Ala Arg Met Thr Gly Ile Asn Thr Ile Phe Ile
305                 310                 315                 320

Asp Asp Arg Asp Pro Phe Ala His Gly Phe Val Val Arg
                325                 330

<210> SEQ ID NO 40
<211> LENGTH: 332
<212> TYPE: PRT
<213> ORGANISM: Agrobacterium tumefaciens

<400> SEQUENCE: 40

Met Arg His Ser Phe Phe Cys Ile Asp Ser His Thr Cys Gly Asn Pro
  1               5                  10                  15

Val Arg Leu Val Ala Gly Gly Pro Leu Leu Pro His Leu Pro Ile
             20                  25                  30

Ser Glu Arg Arg Asp Leu Phe Val Arg Asn His Asp Trp Val Arg Gln
         35                  40                  45

Ala Leu Met Phe Glu Pro Arg Gly His Asp Ile Met Ser Gly Ala Val
     50                  55                  60

Ile Tyr Pro Ala Tyr Arg Asp Asp Cys Asp Phe Ala Val Ile Phe Ile
 65                  70                  75                  80

Glu Val Ser Gly Cys Leu Pro Met Cys Gly Ala Gly Thr Ile Gly Leu
                 85                  90                  95

Val Thr Ala Ala Ile Glu Glu Gly Leu Val Thr Pro Arg Ile Pro Gly
            100                 105                 110

Arg Leu Ser Ile Glu Thr Pro Ala Gly Lys Val Asp Ile Gln Tyr Asp
        115                 120                 125
```

```
Lys Pro Gly Glu Phe Val Glu Ser Val Arg Ile Phe Asn Val Ala Ser
        130                 135                 140

Tyr Leu His Ala Ala Asp Val Glu Val Asn Val Pro Gly Leu Gly Lys
145                 150                 155                 160

Leu Val Val Asp Ile Ala Tyr Gly Gly Asn Tyr Tyr Ala Val Ile Glu
                165                 170                 175

Pro Gln Val Gly Trp Pro Gly Leu Asp Gly Met Thr Ala Gly Asp Val
            180                 185                 190

Val Asp Leu Ser Gln Lys Leu Arg Asp Ala Leu Gly Thr Ile Cys Asp
        195                 200                 205

Pro Val His Pro Asp Asp Glu Arg Ile Arg Gly Val His His Ala Ile
    210                 215                 220

Trp Cys Asp Arg Pro Val Ser Ala Glu Ala Asp Gly Arg Gly Ala Val
225                 230                 235                 240

Phe Tyr Gly Asp Lys Ala Ile Asp Arg Ser Pro Gly Gly Thr Gly Thr
                245                 250                 255

Ser Ala Arg Met Ala Gln Leu His Gly Lys Gly Arg Leu Lys Ala Gly
            260                 265                 270

Glu Thr Phe Arg Gln Glu Ser Leu Ile Gly Thr Ile Phe Glu Gly Lys
        275                 280                 285

Val Glu Glu Glu Thr Thr Val Gly Ser Phe Ser Gly Ile Arg Pro Ser
    290                 295                 300

Ile Gly Gly Trp Ala Arg Ile Ile Gly His Asn Thr Ile Phe Val Asp
305                 310                 315                 320

Asp Arg Asp Pro Leu Ala His Gly Phe Gln Val Arg
                325                 330

<210> SEQ ID NO 41
<211> LENGTH: 312
<212> TYPE: PRT
<213> ORGANISM: Xanthomonas campestris

<400> SEQUENCE: 41

Met His Thr Ile Asp Val Ile Asp Ser His Thr Ala Gly Glu Pro Thr
  1               5                  10                  15

Arg Val Val Leu Ala Gly Phe Pro Asp Leu Gly Asp Gly Asp Leu Ala
                20                  25                  30

Gln Cys Arg Glu Arg Phe Arg Ser Asp Phe Asp His Trp Arg Ser Ala
            35                  40                  45

Ile Ala Cys Glu Pro Arg Gly Ser Asp Thr Met Val Gly Ala Leu Leu
        50                  55                  60

Leu Pro Pro Arg Asp Pro Ser Ala Cys Thr Gly Val Ile Phe Phe Asn
 65                  70                  75                  80

Asn Val Gly Tyr Leu Gly Met Cys Gly His Gly Thr Ile Gly Val Val
                85                  90                  95

Arg Thr Leu Ala Glu Leu Gly Arg Ile Ala Pro Gly Gln His Arg Ile
            100                 105                 110

Glu Thr Pro Val Gly Thr Val Gly Val Ala Leu Ala Asp Asp Gly Thr
        115                 120                 125

Val Ser Ile Asp Asn Val Glu Ser Tyr Arg His Ala Ala Gly Val Glu
    130                 135                 140

Val Asp Val Pro Gly His Gly Arg Val Arg Gly Asp Val Ala Trp Gly
145                 150                 155                 160

Gly Asn Trp Phe Phe Ile Thr Glu Gln Ala Pro Cys Ala Leu Gly Leu
```

```
                165                 170                 175
Ala Gln Gln Arg Glu Leu Thr Ala Tyr Thr Glu Ala Ile Arg Leu Ala
            180                 185                 190

Leu Glu Ala Ala Gly Ile Thr Gly Glu Ala Gly Gly Glu Ile Asp His
        195                 200                 205

Ile Glu Ile Ser Gly Val Ala Pro Asp Gly Ser Gly Ala Ala Arg Asn
210                 215                 220

Phe Val Leu Cys Pro Gly Leu Ala Tyr Asp Arg Ser Pro Cys Gly Thr
225                 230                 235                 240

Gly Thr Ser Ala Lys Leu Ala Cys Leu Ala Ala Asp Gly Lys Leu Ala
            245                 250                 255

Glu Gly Glu Arg Trp Leu Gln Gln Gly Ile Leu Gly Ser Ala Phe Glu
        260                 265                 270

Gly Ser Tyr Arg His Ser Gly Arg Gly Ile Ala Pro Arg Ile Ser Gly
    275                 280                 285

His Ala Phe Ile Thr Ala Arg Ser Gln Leu Leu Ile Asp Pro Ala Asp
290                 295                 300

Pro Phe Ala Trp Gly Ile Val Ala
305                 310

<210> SEQ ID NO 42
<211> LENGTH: 312
<212> TYPE: PRT
<213> ORGANISM: Xanthomonas axonopodis

<400> SEQUENCE: 42

Met His Thr Ile Asp Val Ile Asp Ser His Thr Ala Gly Glu Pro Thr
1               5                   10                  15

Arg Val Val Leu Ser Gly Phe Pro Leu Gly Asp Gly Asp Leu Ala
            20                  25                  30

Gln Cys Arg Glu Arg Phe Arg Ser Glu Phe Asp His Trp Arg Ser Ala
        35                  40                  45

Ile Ala Cys Glu Pro Arg Gly Ser Asp Thr Met Val Gly Ala Leu Leu
    50                  55                  60

Leu Pro Pro Ar

```
Phe Val Leu Cys Pro Gly Leu Ala Tyr Asp Arg Ser Pro Cys Gly Thr
225                 230                 235                 240

Gly Thr Ser Ala Lys Leu Ala Cys Leu Ala Ala Asp Gly Lys Leu Ala
                245                 250                 255

Glu Gly Glu Arg Trp Val Gln Gln Gly Ile Leu Gly Ser Ala Phe Glu
            260                 265                 270

Gly Asn Tyr Arg Leu Ser Gly Arg Gly Ile Ala Pro Arg Ile Ser Gly
        275                 280                 285

Arg Ala Tyr Ile Thr Ala Arg Ala Gln Leu Val Ile Asp Pro Ala Asp
    290                 295                 300

Pro Phe Ala Trp Gly Ile Val Ala
305                 310

<210> SEQ ID NO 43
<211> LENGTH: 314
<212> TYPE: PRT
<213> ORGANISM: Pseudomonas aeruginosa

<400> SEQUENCE: 43

Met Gln Arg Ile Arg Ile Ile Asp Ser His Thr Gly Gly Glu Pro Thr
1               5                   10                  15

Arg Leu Val Ile Gly Gly Phe Pro Asp Leu Gly Gln Gly Asp Met Ala
            20                  25                  30

Glu Arg Arg Arg Leu Leu Gly Glu Arg His Asp Ala Trp Arg Ala Ala
        35                  40                  45

Cys Ile Leu Glu Pro Arg Gly Ser Asp Val Leu Val Gly Ala Leu Leu
    50                  55                  60

Cys Ala Pro Val Asp Pro Glu Ala Cys Ala Gly Val Ile Phe Phe Asn
65                  70                  75                  80

Asn Ser Gly Tyr Leu Gly Met Cys Gly His Gly Thr Ile Gly Leu Val
                85                  90                  95

Ala Ser Leu Ala His Leu Gly Arg Ile Gly Pro Gly Val His Arg Ile
            100                 105                 110

Glu Thr Pro Val Gly Glu Val Glu Ala Thr Leu His Glu Asp Gly Ser
        115                 120                 125

Val Ser Val Arg Asn Val Pro Ala Tyr Arg Tyr Arg Arg Gln Val Ser
    130                 135                 140

Val Glu Val Pro Gly Ile Gly Arg Val Ser Gly Asp Ile Ala Trp Gly
145                 150                 155                 160

Gly Asn Trp Phe Phe Leu Val Ala Gly His Gly Gln Arg Leu Ala Gly
                165                 170                 175

Asp Asn Leu Asp Ala Leu Thr Ala Tyr Thr Val Ala Val Gln Gln Ala
            180                 185                 190

Leu Asp Asp Gln Asp Ile Arg Gly Glu Asp Gly Ala Ile Asp His
        195                 200                 205

Ile Glu Leu Phe Ala Asp Asp Pro His Ala Asp Ser Arg Asn Phe Val
    210                 215                 220

Leu Cys Pro Gly Lys Ala Tyr Asp Arg Ser Pro Cys Gly Thr Gly Thr
225                 230                 235                 240

Ser Ala Lys Leu Ala Cys Leu Ala Ala Asp Gly Lys Leu Leu Pro Gly
                245                 250                 255

Gln Pro Trp Arg Gln Ala Ser Val Ile Gly Ser Gln Phe Glu Gly Arg
            260                 265                 270

Tyr Glu Trp Leu Asp Gly Gln Pro Gly Gly Pro Ile Val Pro Thr Ile
        275                 280                 285
```

```
Arg Gly Arg Ala His Val Ser Ala Glu Ala Thr Leu Leu Ala Asp
    290                 295                 300

Asp Asp Pro Phe Ala Trp Gly Ile Arg Arg
305                 310
```

<210> SEQ ID NO 44
<211> LENGTH: 344
<212> TYPE: PRT
<213> ORGANISM: Pseudomonas aeruginosa

<400> SEQUENCE: 44

```
Met Arg Ser Gln Arg Ile Val His Ile Val Ser Cys His Ala Glu Gly
  1               5                  10                  15

Glu Val Gly Asp Val Ile Val Gly Gly Val Ala Ala Pro Pro Gly Ala
             20                  25                  30

Thr Leu Trp Glu Gln Ser Arg Trp Ile Ala Arg Asp Gln Asp Leu Arg
         35                  40                  45

Asn Phe Val Leu Asn Glu Pro Arg Gly Gly Val Phe Arg His Ala Asn
     50                  55                  60

Leu Leu Val Pro Ala Lys Asp Pro Arg Ala Gln Met Gly Trp Ile Ile
 65                  70                  75                  80

Met Glu Pro Ala Asp Thr Pro Pro Met Ser Gly Ser Asn Ser Leu Cys
                 85                  90                  95

Val Ala Thr Val Leu Leu Asp Ser Gly Ile Leu Pro Met Arg Glu Pro
            100                 105                 110

Leu Thr Arg Leu Leu Leu Glu Ala Pro Gly Gly Leu Ile Glu Ala Arg
        115                 120                 125

Ala Glu Cys Arg Asp Gly Lys Ala Glu Arg Val Glu Ile Arg Asn Val
    130                 135                 140

Pro Ser Phe Ala Asp Arg Leu Asp Ala Trp Ile Glu Val Glu Gly Leu
145                 150                 155                 160

Gly Ser Leu Gln Val Asp Thr Ala Tyr Gly Gly Asp Ser Phe Val Ile
                165                 170                 175

Ala Asp Ala Arg Arg Leu Gly Phe Ala Leu Arg Ala Asp Glu Ala Ala
            180                 185                 190

Glu Leu Val Ala Thr Gly Leu Lys Ile Thr His Ala Ala Asn Glu Gln
        195                 200                 205

Leu Gly Phe Arg His Pro Thr Asn Pro Asp Trp Asp His Leu Ser Phe
    210                 215                 220

Cys Gln Leu Ala Ala Pro Glu Arg Arg Asp Gly Val Leu Gly Ala
225                 230                 235                 240

Asn Asn Ala Val Val Ile Arg Pro Gly Lys Ile Asp Arg Ser Pro Cys
                245                 250                 255

Gly Thr Gly Cys Ser Ala Arg Met Ala Val Leu Gln Ala Lys Gly Gln
            260                 265                 270

Leu Arg Val Gly Glu Arg Phe Val Gly Arg Ser Ile Ile Gly Ser Glu
        275                 280                 285

Phe His Cys His Ile Glu Ser Leu Thr Glu Leu Gly Gly Arg Pro Ala
    290                 295                 300

Ile Leu Pro Cys Leu Ser Gly Arg Ala Trp Ile Thr Gly Ile His Gln
305                 310                 315                 320

Tyr Leu Leu Asp Pro Asp Pro Trp Pro Gln Gly Tyr Arg Leu Ser
                325                 330                 335

Asp Thr Trp Pro Gly Gly His Cys
```

-continued

```
          340

<210> SEQ ID NO 45
<211> LENGTH: 342
<212> TYPE: PRT
<213> ORGANISM: Brucella melitensis

<400> SEQUENCE: 45

Met Arg Ser Thr Lys Val Ile His Ile Val Gly Cys His Ala Glu Gly
  1               5                  10                  15

Glu Val Gly Asp Val Ile Val Gly Gly Val Ala Pro Pro Pro Gly Glu
             20                  25                  30

Thr Val Trp Glu Gln Ser Arg Phe Ile Ala Asn Asp Glu Thr Leu Arg
         35                  40                  45

Asn Phe Val Leu Asn Lys Pro Arg Gly Gly Val Phe Arg His Val Asn
     50                  55                  60

Leu Leu Val Pro Pro Lys Asp Pro Arg Ala Gln Met Gly Phe Ile Ile
 65                  70                  75                  80

Met Glu Pro Ala Asp Thr Pro Pro Met Ser Gly Ser Asn Ser Ile Cys
                 85                  90                  95

Val Ser Thr Val Leu Leu Asp Ser Gly Ile Ile Ala Met Gln Glu Pro
            100                 105                 110

Val Thr His Met Val Leu Glu Ala Pro Gly Gly Ile Ile Glu Val Glu
        115                 120                 125

Ala Glu Cys Arg Asn Gly Lys Ala Glu Arg Ile Ser Val Arg Asn Val
    130                 135                 140

Pro Ser Phe Ala Asp Arg Leu Asp Ala Pro Leu Asp Val Thr Gly Leu
145                 150                 155                 160

Gly Thr Ile Met Val Asp Thr Ala Tyr Gly Gly Asp Ser Phe Val Ile
                165                 170                 175

Val Asp Ala Ala Gln Ile Gly Met Lys Ile Glu Pro Gly Gln Ala Arg
            180                 185                 190

Glu Leu Ala Glu Ile Gly Val Lys Ile Thr Lys Ala Ala Asn Glu Gln
        195                 200                 205

Leu Gly Phe Arg His Pro Glu Arg Asp Trp Arg His Ile Ser Phe Cys
    210                 215                 220

Gln Ile Thr Glu Pro Val Thr Arg Glu Gly Asp Val Leu Thr Gly Val
225                 230                 235                 240

Asn Thr Val Ala Ile Arg Pro Ala Lys Phe Asp Arg Ser Pro Thr Gly
                245                 250                 255

Thr Gly Cys Ser Ala Arg Met Ala Val Leu His Ala Lys Gly Gln Met
            260                 265                 270

Lys Ala Gly Glu Arg Phe Ile Gly Lys Ser Val Leu Gly Thr Glu Phe
        275                 280                 285

His Cys Arg Leu Asp Lys Val Leu Glu Leu Gly Gly Lys Pro Ala Ile
    290                 295                 300

Ser Pro Ile Ile Ser Gly Arg Ala Trp Val Thr Gly Thr Ser Gln Leu
305                 310                 315                 320

Met Leu Asp Pro Ser Asp Pro Phe Pro His Gly Tyr Arg Leu Ser Asp
                325                 330                 335

Thr Trp Pro Arg Asp Glu
            340

<210> SEQ ID NO 46
<211> LENGTH: 342
```

```
<212> TYPE: PRT
<213> ORGANISM: Agrobacterium tumefaciens

<400> SEQUENCE: 46

Met Arg Ser Ile Lys Thr Val His Val Ile Ser Ala His Ala Glu Gly
 1               5                  10                  15

Glu Val Gly Asp Val Ile Val Gly Gly Val Lys Pro Pro Gly Glu
             20                  25                  30

Thr Ile Trp Glu Gln Ser Arg Phe Ile Ala Arg Asp Glu Thr Leu Arg
             35                  40                  45

Asn Phe Val Leu Asn Glu Pro Arg Gly Val Phe Arg His Val Asn
 50                  55                  60

Leu Leu Val Pro Pro Lys His Pro Asp Ala Asp Ala Ala Phe Ile Ile
 65                  70                  75                  80

Met Glu Pro Glu Asp Thr Pro Pro Met Ser Gly Ser Asn Ser Ile Cys
                 85                  90                  95

Val Ser Thr Val Leu Leu Asp Gly Gly Ile Val Pro Met Gln Glu Pro
                100                 105                 110

Glu Thr His Met Leu Leu Glu Ala Pro Gly Gly Leu Val Lys Val Arg
            115                 120                 125

Ala Glu Cys Arg Asn Gly Lys Ala Glu Arg Ile Phe Val Gln Asn Leu
        130                 135                 140

Pro Ser Phe Ala Ala Lys Leu Asp Ala Glu Leu Glu Val Glu Gly Leu
145                 150                 155                 160

Gly Lys Leu Lys Val Asp Thr Ala Tyr Gly Gly Asp Ser Phe Val Ile
                165                 170                 175

Val Asp Ala Glu Ala Met Gly Phe Ser Leu Lys Pro Glu Glu Ala His
            180                 185                 190

Glu Ile Ala Arg Leu Gly Val Arg Ile Thr Asn Ala Ala Asn Lys Ala
        195                 200                 205

Leu Gly Phe Asp His Pro Glu Asn Pro Asp Trp Arg His Phe Ser Phe
    210                 215                 220

Cys Leu Phe Ala Gly Lys Val Glu Arg Thr Ala Glu Gly Leu Arg Ala
225                 230                 235                 240

Gly Ala Ala Val Ala Ile Gln Pro Gly Lys Val Asp Arg Ser Pro Thr
                245                 250                 255

Gly Thr Ala Leu Ser Ala Arg Met Ala Val Leu His Ala Arg Gly Glu
            260                 265                 270

Met Lys Glu Gly Glu Thr Leu Thr Ala Val Ser Leu Ile Gly Ser Thr
        275                 280                 285

Phe Thr Gly Arg Ile Leu Gly Thr Thr Val Gly Asp Arg Pro Ala
    290                 295                 300

Ile Leu Pro Glu Ile Ser Gly Arg Gly Trp Ile Thr Gly Ile His Gln
305                 310                 315                 320

His Met Leu Asp Pro Ser Asp Pro Trp Pro Glu Gly Tyr Arg Leu Thr
                325                 330                 335

Asp Thr Trp Gly Ala Arg
            340

<210> SEQ ID NO 47
<211> LENGTH: 342
<212> TYPE: PRT
<213> ORGANISM: Rhizobium meliloti

<400> SEQUENCE: 47
```

Met Arg Ser Thr Lys Thr Ile His Val Ile Ser Ala His Ala Glu Gly
1               5                   10                  15

Glu Val Gly Asp Val Ile Val Gly Val Ala Pro Pro Gly Asp
                20                  25                  30

Thr Ile Trp Glu Gln Ser Arg Trp Ile Ala Arg Glu Gln Thr Leu Arg
            35                  40                  45

Asn Phe Val Leu Asn Glu Pro Arg Gly Val Phe Arg His Val Asn
    50                  55                  60

Leu Leu Val Pro Pro Lys His Pro Asp Ala Asp Ala Ala Phe Ile Ile
65                  70                  75                  80

Met Glu Pro Glu Asp Thr Pro Pro Met Ser Gly Ser Asn Ser Ile Cys
                85                  90                  95

Val Ser Thr Val Leu Leu Asp Ser Gly Ile Leu Pro Met Lys Glu Pro
                100                 105                 110

Val Thr Glu Ile Thr Leu Glu Ala Pro Gly Gly Leu Val Arg Val Arg
                115                 120                 125

Ala Glu Cys Arg Asp Gly Lys Ala Glu Arg Ile Phe Val Glu Asn Leu
            130                 135                 140

Pro Ser Phe Ala Glu Arg Leu Asp Ala Lys Leu Glu Val Glu Gly Leu
145                 150                 155                 160

Gly Thr Leu Thr Val Asp Thr Ala Tyr Gly Gly Asp Ser Phe Val Ile
                165                 170                 175

Val Asp Ala Ala Ala Met Gly Phe Ala Leu Lys Pro Asp Glu Ala His
                180                 185                 190

Asp Ile Ala Arg Leu Gly Val Arg Ile Thr Asn Ala Ala Asn Ala Lys
            195                 200                 205

Leu Gly Phe His His Pro Glu Asn Pro Asp Trp Arg His Phe Ser Phe
210                 215                 220

Cys Leu Phe Ala Gly Pro Val Glu Arg Thr Ala Glu Gly Leu Arg Ala
225                 230                 235                 240

Gly Ala Ala Val Ala Ile Gln Pro Gly Lys Val Asp Arg Ser Pro Thr
                245                 250                 255

Gly Thr Ala Leu Ser Ala Arg Met Ala Val Leu His Ala Arg Gly Gln
            260                 265                 270

Met Gly Leu Ser Asp Arg Leu Thr Ala Val Ser Leu Ile Gly Ser Thr
            275                 280                 285

Phe Ser Gly Arg Ile Leu Gly Thr Thr Glu Val Gly Gly Arg Pro Ala
290                 295                 300

Val Leu Pro Glu Ile Ser Gly Arg Ala Trp Ile Thr Gly Thr His Gln
305                 310                 315                 320

His Met Leu Asp Pro Ser Asp Pro Trp Pro Glu Gly Tyr Arg Leu Thr
                325                 330                 335

Asp Thr Trp Gly Ala Arg
            340

<210> SEQ ID NO 48
<211> LENGTH: 346
<212> TYPE: PRT
<213> ORGANISM: Rhizobium loti

<400> SEQUENCE: 48

Met Arg Ser Lys Thr Ser Ile Arg Val Gly Cys His Ala Glu Gly
1               5                   10                  15

Glu Val Gly Asp Val Ile Ile Gly Gly Val Leu Pro Pro Ala Gly Arg
                20                  25                  30

-continued

```
Thr Met Met Asp Lys Met Ile Thr Met Glu Arg Asp His Asp His Ile
        35                  40                  45

Arg Arg Met Leu Ile Cys Glu Pro Arg Gly Ser Val Ala Arg His Val
    50                  55                  60

Asn Leu Leu Val Pro Ser Thr Arg Glu Asp Cys Ala Ala Gly Ala Ile
65                  70                  75                  80

Ile Met Glu Pro Thr Glu Tyr Pro Pro Met Ser Gly Ser Asn Thr Ile
                85                  90                  95

Cys Val Ala Thr Val Leu Leu Glu Thr Gly Met Val Pro Met Gln Glu
            100                 105                 110

Pro Glu Thr Arg Phe Lys Leu Asp Met Pro Gly Gly Val Ile Glu Val
        115                 120                 125

Arg Ala Gln Cys Arg Asp Gly Lys Cys Val Ser Ile Thr Leu Arg Asn
    130                 135                 140

Ala Pro Ala Phe Val Asp Arg Leu Asp Ala Ser Ile Glu Val Glu Gly
145                 150                 155                 160

Leu Gly Thr Leu Thr Val Asp Ile Ala Tyr Gly Gly Met Phe Tyr Ala
                165                 170                 175

Ile Val Asp Ala Lys Ala Leu Gly Phe Ser Ile Ala Pro Asp Glu Ala
            180                 185                 190

Arg Glu Leu Ala Val Ala Gly Glu Lys Ile Arg Arg Ala Ala Arg Glu
        195                 200                 205

Gln Leu Asp Val Val His Pro Gln Phe Asp His Val Arg Gly Val Ser
    210                 215                 220

Ile Val Gln Phe Ala Met Pro Phe Gln Gly Pro Gly Asn Val Thr Arg
225                 230                 235                 240

Asn Thr Cys Ile Val Ser Pro Gly Arg Ser Asp Arg Ser Pro Thr Gly
                245                 250                 255

Thr Gly Thr Ser Ala Arg Met Ala Val Leu Gln Ala Arg Gly Leu Met
            260                 265                 270

Gly Val Gly Asp Val Leu Ile His Glu Ser Ile Ile Gly Ser Arg Phe
        275                 280                 285

Thr Gly Arg Ile Val Glu Leu Ala Glu Ile Ala Gly Arg Lys Ala Ile
    290                 295                 300

Val Pro Glu Ile Thr Gly Arg Ala Trp Ile Thr Gly Glu His Ser Tyr
305                 310                 315                 320

Tyr Leu Asp Pro Thr Asp Pro Tyr Pro Gln Gly Tyr Val Leu Ser Asp
                325                 330                 335

Thr Trp Gly Thr Ser Thr Ser Val Lys Gln
            340                 345
```

<210> SEQ ID NO 49
<211> LENGTH: 339
<212> TYPE: PRT
<213> ORGANISM: Xanthomonas axonopodis

<400> SEQUENCE: 49

```
Met Arg Trp Ser Lys Gln Phe Ser Val Val Asp Cys His Ala Glu Gly
  1               5                  10                  15

Glu Val Gly Lys Val Ile Val Gly Gly Val Gly Asn Ile Pro Gly Thr
            20                  25                  30

Thr Met Phe Glu Lys Lys Leu Tyr Leu Glu Gln His Arg Asp Asp Ile
        35                  40                  45

Arg Lys Leu Val Leu Gln Glu Pro Arg Gly Ala Thr Trp His Asn Ala
```

```
              50                  55                  60
Asn Ile Ile Leu Pro Pro Ser His Pro Glu Ala Ser Met Gly Phe Val
 65                  70                  75                  80

Ile Leu Glu Ala Thr Glu Tyr Pro Ala Met Ser Gly Ser Asn Thr Ile
                 85                  90                  95

Cys Val Ala Thr Val Leu Leu Glu Thr Gly Ile Leu Pro Met Gln Glu
            100                 105                 110

Pro Ile Thr Asp Leu Val Leu Glu Ala Pro Ala Gly Leu Ile Arg Val
            115                 120                 125

Arg Cys Asp Cys Lys Asp Gly Lys Val Thr Arg Val Lys Leu Val Asn
130                 135                 140

Gln Pro Ala Phe Val Tyr His Leu Asp Ala Lys Val Glu Val Ala Gly
145                 150                 155                 160

Ile Gly Thr Val Ser Ala Asp Ile Ala Phe Gly Met Thr Phe Ala
                165                 170                 175

Leu Val Asp Ala Ser Ser Leu Gly Phe Glu Ile Val Pro Ala Glu Ala
            180                 185                 190

Arg Glu Leu Cys Glu Tyr Gly Gln Lys Ile Lys Ala Ala Ala Glu
            195                 200                 205

Gln Leu Asp Val Ala Phe Pro Gly Asn Pro Asp Met Pro Gly Ile Thr
            210                 215                 220

Met Thr Gln Phe Thr Gly Pro Leu Ser Arg Ala Asp Gly Lys Phe Phe
225                 230                 235                 240

Ser Arg Asn Thr Thr Ile Val Ser Pro Gly Arg Cys Asp Arg Ser Pro
                245                 250                 255

Cys Gly Ala Gly Ser Ser Ala Arg Leu Ala Ala Leu His Ala Lys Gly
            260                 265                 270

Val Leu Ala Lys Gly Asp Thr Leu Val His Glu Ser Ile Ile Gly Ser
            275                 280                 285

Arg Phe Glu Cys Gly Ile Glu Asp Met Ser Asn Val Gly Asp Tyr Pro
            290                 295                 300

Ala Val Val Pro Ser Ile Ala Gly Gln Ala Trp Ile Ser Gly Leu Ser
305                 310                 315                 320

Gln Leu Gly Leu Asp Pro Ser Asp Pro Tyr Ala Glu Gly Phe Thr Leu
                325                 330                 335

Ala Asp Arg

<210> SEQ ID NO 50
<211> LENGTH: 333
<212> TYPE: PRT
<213> ORGANISM: Streptomyces coelicolor

<400> SEQUENCE: 50

Met Arg Ser Thr Val Cys Tyr His Ala Val Asp Ser His Thr Glu Gly
  1               5                  10                  15

Met Pro Thr Arg Val Ile Thr Gly Gly Val Gly Val Leu Pro Gly Ala
                 20                  25                  30

Thr Met Phe Glu Arg Arg Gln Arg Phe Val Ala Glu Arg Asp His Leu
             35                  40                  45

Arg Thr Leu Leu Met Cys Glu Pro Arg Gly His Ala Ser Met Ser Gly
         50                  55                  60

Ala Ile Leu Gln Pro Pro Thr Arg Pro Asp Ala Asp Tyr Gly Val Leu
 65                  70                  75                  80

Phe Ile Glu Val Ser Gly Cys Leu Pro Met Cys Gly His Gly Thr Ile
```

```
                85                  90                  95
Gly Val Ala Thr Val Leu Val Glu Thr Gly Met Val Glu Val Thr Glu
            100                 105                 110
Pro Glu Thr Thr Val Arg Leu Asp Thr Pro Ala Gly Leu Val Thr Ala
            115                 120                 125
Arg Val Arg Val Arg Asp Gly His Ala Glu Ser Val Thr Leu Glu Asn
        130                 135                 140
Val Ala Ser Tyr Ser His Ala Leu Asp Gln Val Val Asp Val Pro Gly
145                 150                 155                 160
His Gly Glu Val Arg Tyr Asp Ile Ala Tyr Gly Gly Asn Phe Tyr Ala
                165                 170                 175
Phe Val Arg Thr Asp Asp Leu Gly Ile Pro Phe Glu Arg Ala His Lys
            180                 185                 190
Gln Pro Leu Leu Asp Ala Gly Leu Ala Val Met Asp Ala Ile Asn Lys
            195                 200                 205
Gln Asn Pro Val Ser His Pro Glu Asn Pro Asp Ile Asp Val Cys His
        210                 215                 220
His Val Tyr Leu Glu Ala Pro Gly Ser Thr Ala Glu His Ser Arg His
225                 230                 235                 240
Ala Met Ala Ile His Pro Gly Trp Phe Asp Arg Ser Pro Cys Gly Thr
                245                 250                 255
Gly Thr Ser Ala Arg Met Ala Gln Leu His Ala Arg Gly Leu Leu Pro
            260                 265                 270
Ala Gly Arg Asp Phe Val Asn Glu Ser Phe Ile Gly Ser Arg Phe Val
            275                 280                 285
Gly Arg Val Leu Gly Glu Thr Thr Val Gly Gly Arg Pro Ala Val Leu
        290                 295                 300
Pro Ser Val Thr Gly Arg Ala Trp Ile Thr Gly Thr Ala Gln Tyr Leu
305                 310                 315                 320
Leu Asp Pro Ser Asp Pro Tyr Pro Ala Gly Phe Thr Leu
                325                 330

<210> SEQ ID NO 51
<211> LENGTH: 345
<212> TYPE: PRT
<213> ORGANISM: Agrobacterium tumefaciens

<400> SEQUENCE: 51

Met Arg Trp Lys Arg Thr Leu Gln Leu Leu Asp Val His Cys Glu Gly
1               5                   10                  15
Glu Ile Gly Arg Val Val Thr Gly Gly Ala Pro Lys Ile Pro Gly Asn
                20                  25                  30
Thr Val Ala Glu Gln Leu His Trp Met Asn Thr Asp Pro Gln Gly Glu
            35                  40                  45
Ala Leu Arg Arg Phe Leu Thr Leu Glu Pro Arg Gly Thr Pro Met Gly
        50                  55                  60
Ser Val Asp Leu Leu Pro Pro Lys His Pro Asp Ala His Ala Ala
65                  70                  75                  80
Phe Val Ile Leu Gln Pro Asp Gln Ala His Ala Ser Ser Gly Ser Asn
                85                  90                  95
Ser Ile Cys Ala Thr Thr Ala Leu Leu Glu Ser Gly Met Val Glu Met
            100                 105                 110
Gln Glu Pro Glu Thr Val Ile Ile Leu Glu Thr Ala Ala Gly Leu Val
        115                 120                 125
```

```
Lys Ala Thr Ala Thr Cys Arg Asp Gly Arg Cys Glu Lys Val Lys Leu
            130                 135                 140

Thr Met Val Pro Ser Phe Val His Glu Leu Asp Val Ser Ile Asp Thr
145                 150                 155                 160

Pro Glu Trp Gly Arg Val Thr Met Asp Ile Ser Tyr Gly Gly Ile Phe
                165                 170                 175

Tyr Ala Leu Val Asp Val Arg Gln Ile Gly Leu Thr Ile Glu Lys Ala
            180                 185                 190

Asn Ala Ala Lys Leu Val Ala Ala Gly Met Thr Leu Lys Asp Leu Val
            195                 200                 205

Asn Arg Glu Met Thr Val Val His Pro Glu Ile Pro Ala Ile Ser Gly
210                 215                 220

Val Ala Tyr Val Met Phe Arg Asp Val Asp Ala Asp Gly Ser Ile Arg
225                 230                 235                 240

Thr Cys Thr Thr Met Trp Pro Gly Arg Ala Asp Arg Ser Pro Cys Gly
                245                 250                 255

Thr Gly Asn Ser Ala Asn Leu Ala Thr Leu Tyr Ala Arg Gly Lys Val
            260                 265                 270

Lys Val Gly Asp Glu Tyr Lys Ser Arg Ser Ile Ile Gly Ser Glu Phe
            275                 280                 285

Asp Val Gly Leu Ser Ala Val Thr Glu Val Ala Gly Arg Pro Ala Val
            290                 295                 300

Ile Pro Thr Ile Ala Gly Arg Gly Phe Thr Phe Gly Leu His Gln Val
305                 310                 315                 320

Gly Leu Asp Pro Phe Asp Pro Leu Gly Asp Gly Phe Ala Met Thr Asp
                325                 330                 335

Val Trp Gly Pro Glu Ala Gly Asn Ile
                340                 345

<210> SEQ ID NO 52
<211> LENGTH: 354
<212> TYPE: PRT
<213> ORGANISM: Trypanosoma cruzi

<400> SEQUENCE: 52

Met Arg Phe Lys Lys Ser Leu Thr Cys Ile Asp Met His Thr Glu Gly
1               5                   10                  15

Glu Ala Ala Arg Ile Val Thr Ser Gly Leu Pro His Ile Pro Gly Ser
                20                  25                  30

Asn Met Ala Glu Lys Lys Ala Tyr Leu Gln Glu Asn Met Asp Tyr Leu
            35                  40                  45

Arg Arg Gly Ile Met Leu Glu Pro Arg Gly His Asp Asp Met Phe Gly
    50                  55                  60

Ala Phe Leu Phe Asp Pro Ile Glu Glu Gly Ala Asp Leu Gly Ile Val
65                  70                  75                  80

Phe Met Asp Thr Gly Gly Tyr Leu Asn Met Cys Gly His Asn Ser Ile
                85                  90                  95

Ala Ala Val Thr Ala Ala Val Glu Thr Gly Ile Leu Ser Val Pro Ala
            100                 105                 110

Lys Ala Thr Asn Val Pro Val Val Leu Asp Thr Pro Ala Gly Leu Val
            115                 120                 125

Arg Gly Thr Ala His Leu Gln Ser Gly Thr Glu Ser Glu Val Ser Asn
    130                 135                 140

Ala Ser Ile Ile Asn Val Pro Ser Phe Leu Tyr Gln Gln Asp Val Val
145                 150                 155                 160
```

-continued

```
Ile Val Leu Pro Lys Pro Tyr Gly Glu Val Arg Val Asp Ile Ala Phe
                165                 170                 175
Gly Gly Asn Phe Phe Ala Ile Val Pro Ala Glu His Leu Gly Ile Asp
            180                 185                 190
Ile Ser Val Gln Asn Leu Ser Arg Leu Gln Glu Ala Gly Glu Leu Leu
        195                 200                 205
Arg Thr Glu Ile Asn Arg Ser Val Lys Val Gln His Pro Gln Leu Pro
    210                 215                 220
His Ile Asn Thr Val Asp Cys Val Glu Ile Tyr Gly Pro Thr Asn
225                 230                 235                 240
Pro Glu Ala Lys Tyr Lys Asn Val Val Ile Phe Gly Asn Arg Gln Ala
                245                 250                 255
Asp Arg Ser Pro Cys Gly Thr Gly Thr Ser Ala Lys Met Ala Thr Leu
            260                 265                 270
Tyr Ala Lys Gly Gln Leu Arg Ile Gly Glu Thr Phe Val Tyr Glu Ser
        275                 280                 285
Ile Leu Gly Ser Leu Phe Gln Gly Arg Val Leu Gly Glu Glu Arg Ile
    290                 295                 300
Pro Gly Val Lys Val Pro Val Thr Lys Asp Ala Glu Glu Gly Met Leu
305                 310                 315                 320
Val Val Thr Thr Glu Ile Thr Gly Lys Ala Phe Ile Met Gly Phe Asn
                325                 330                 335
Thr Met Leu Phe Asp Pro Thr Asp Pro Phe Leu Asn Gly Phe Thr Leu
            340                 345                 350
Lys Arg

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 53 tct cca tgt ggg aca                                              15
Ser Pro Cys Gly Thr
  1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Pro Cys Gly Thr
  1               5

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: CDS
<222> LOCATION: (1)..(15)

<400> SEQUENCE: 55 tct cca agc ggg aca                                                       15
Ser Pro Ser Gly Thr
  1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Pro Ser Gly Thr
  1               5

<210> SEQ ID NO 57
<211> LENGTH: 146
<212> TYPE: PRT
<213> ORGANISM: Trypanosoma cruzi

<400> SEQUENCE: 57

Gly Glu Val Arg Val Asp Ile Ala Phe Gly Gly Asn Phe Phe Ala Ile
  1               5                  10                  15

Val Pro Ala Glu Gln Leu Gly Ile Asp Ile Ser Val Gln Asn Leu Ser
             20                  25                  30

Arg Leu Gln Glu Ala Gly Glu Leu Leu Arg Thr Glu Ile Asn Arg Ser
         35                  40                  45

Val Lys Val Gln His Pro Gln Leu Pro His Ile Asn Thr Val Asp Cys
     50                  55                  60

Val Glu Ile Tyr Gly Pro Pro Thr Asn Pro Glu Ala Asn Tyr Lys Asn
 65                  70                  75                  80

Val Val Ile Phe Gly Asn Arg Gln Ala Asp Arg Ser Pro Cys Gly Thr
                 85                  90                  95

Gly Thr Ser Ala Lys Met Ala Thr Leu Tyr Ala Lys Gly Gln Leu Arg
            100                 105                 110

Ile Gly Glu Thr Phe Val Tyr Glu Ser Ile Leu Gly Ser Leu Phe Gln
        115                 120                 125

Gly Arg Val Leu Gly Glu Arg Ile Pro Gly Val Lys Val Pro Val
    130                 135                 140

Thr Lys
145

<210> SEQ ID NO 58
<211> LENGTH: 146
<212> TYPE: PRT
<213> ORGANISM: Bacillus anthracis

<400> SEQUENCE: 58

Gly Thr Val Glu Ala Asp Ile Ala Tyr Gly Gly Asn Phe Tyr Ala Ile
  1               5                  10                  15

Ile Asp Ala Lys Ser Val Gly Leu Glu Leu Val Pro Glu His Ala Ser
             20                  25                  30

Thr Ile Ile Asp Lys Ala Ile His Ile Arg Asn Ile Ile Asn Glu Arg
         35                  40                  45
```

```
Phe Glu Ile Ile His Pro Glu Tyr Ser Phe Ile Arg Gly Leu Thr His
 50                  55                  60

Val Glu Phe Tyr Thr Asp Pro Thr His Glu Ser Ala His Val Lys Asn
 65                  70                  75                  80

Thr Val Val Val Pro Pro Gly Gly Ile Asp Arg Ser Pro Cys Gly Thr
                 85                  90                  95

Gly Thr Ser Ala Lys Leu Ala Val Leu Tyr Ala Asn Gln Lys Ile Glu
            100                 105                 110

Met Asn Glu Glu Phe Val His Glu Ser Ile Val Gly Ser Leu Phe Lys
            115                 120                 125

Gly Cys Val Ile Asn Thr Thr Asn Val Ala Asn Met Glu Ala Val Val
130                 135                 140

Thr Lys
145

<210> SEQ ID NO 59
<211> LENGTH: 117
<212> TYPE: PRT
<213> ORGANISM: Trypanosoma cruzi

<400> SEQUENCE: 59

Met Arg Phe Lys Lys Ser Phe Thr Cys Ile Asp Met His Thr Glu Gly
  1               5                  10                  15

Glu Ala Ala Arg Ile Val Thr Ser Gly Leu Pro His Ile Pro Gly Ser
                 20                  25                  30

Asn Met Ala Glu Lys Lys Ala Tyr Leu Gln Glu Asn Met Asp Tyr Leu
             35                  40                  45

Arg Arg Gly Ile Met Leu Glu Pro Arg Gly His Asp Asp Met Phe Gly
 50                  55                  60

Ala Phe Leu Phe Asp Pro Ile Glu Glu Gly Ala Asp Leu Gly Met Val
 65                  70                  75                  80

Phe Met Asp Thr Gly Gly Tyr Leu Asn Met Cys Gly His Asn Ser Ile
                 85                  90                  95

Ala Ala Val Thr Ala Ala Val Glu Thr Gly Ile Val Ser Val Pro Ala
            100                 105                 110

Lys Ala Thr Asn Val
            115

<210> SEQ ID NO 60
<211> LENGTH: 117
<212> TYPE: PRT
<213> ORGANISM: Bacillus anthracis

<400> SEQUENCE: 60

Met Arg Thr Gln Lys Val Phe Thr Thr Ile Asp Thr His Thr Gly Gly
  1               5                  10                  15

Asn Pro Thr Arg Thr Leu Ile Ser Gly Leu Pro Lys Leu Leu Gly Glu
                 20                  25                  30

Thr Met Ala Glu Lys Met Leu His Met Lys Lys Glu Tyr Asp Trp Ile
             35                  40                  45

Arg Lys Leu Leu Met Asn Glu Pro Arg Gly His Asp Val Met Ser Gly
 50                  55                  60

Ala Leu Leu Thr Asp Pro Cys His Pro Asp Ala Asp Ile Gly Val Ile
 65                  70                  75                  80

Tyr Ile Glu Thr Gly Gly Tyr Leu Pro Met Cys Gly His Asp Thr Ile
                 85                  90                  95
```

```
Gly Val Cys Thr Ala Leu Ile Glu Ser Gly Leu Ile Pro Val Val Glu
            100                 105                 110

Pro Ile Thr Ser Leu
        115

<210> SEQ ID NO 61
<211> LENGTH: 145
<212> TYPE: PRT
<213> ORGANISM: Trypanosoma cruzi

<400> SEQUENCE: 61

Glu Val Arg Val Asp Ile Ala Phe Gly Gly Asn Phe Phe Ala Ile Val
 1               5                  10                  15

Pro Ala Glu Gln Leu Gly Ile Asp Ile Ser Val Gln Asn Leu Ser Arg
            20                  25                  30

Leu Gln Glu Ala Gly Glu Leu Leu Arg Thr Glu Ile Asn Arg Ser Val
        35                  40                  45

Lys Val Gln His Pro Gln Leu Pro His Ile Asn Thr Val Asp Cys Val
    50                  55                  60

Glu Ile Tyr Gly Pro Pro Thr Asn Pro Glu Ala Asn Tyr Lys Asn Val
 65                 70                  75                  80

Val Ile Phe Gly Asn Arg Gln Ala Asp Arg Ser Pro Cys Gly Thr Gly
                85                  90                  95

Thr Ser Ala Lys Met Ala Thr Leu Tyr Ala Lys Gly Gln Leu Arg Ile
            100                 105                 110

Gly Glu Thr Phe Val Tyr Glu Ser Ile Leu Gly Ser Leu Phe Gln Gly
        115                 120                 125

Arg Val Leu Gly Glu Glu Arg Ile Pro Gly Val Lys Val Pro Val Thr
    130                 135                 140

Lys
145

<210> SEQ ID NO 62
<211> LENGTH: 145
<212> TYPE: PRT
<213> ORGANISM: Bacillus anthracis

<400> SEQUENCE: 62

Glu Phe Gln Val Asp Ile Ala Phe Gly Gly Ala Phe Tyr Ala Val Val
 1               5                  10                  15

Asp Ser Lys Glu Phe Gly Leu Lys Val Asp Phe Lys Asp Leu Ser Ala
            20                  25                  30

Ile Gln Gln Trp Gly Gly Lys Ile Lys His Tyr Ile Glu Ser Lys Met
        35                  40                  45

Glu Val Lys His Pro Leu Glu Glu Gly Leu Lys Gly Ile Tyr Gly Val
    50                  55                  60

Ile Phe Ser Asp Asp Pro Lys Gly Glu Gly Ala Thr Leu Arg Asn Val
 65                 70                  75                  80

Thr Ile Phe Ala Asp Gly Gln Val Asp Arg Ser Pro Cys Gly Thr Gly
                85                  90                  95

Thr Ser Ala Arg Ile Ala Thr Leu Phe Glu Lys Gly Ile Leu Gln Lys
            100                 105                 110

Gly Glu Ile Phe Ile His Glu Cys Ile Thr Asp Gly Glu Phe Glu Gly
        115                 120                 125

Glu Val Leu Ser Val Thr Ala Val His Thr Tyr Glu Ala Val Val Pro
    130                 135                 140
```

Lys
145

<210> SEQ ID NO 63
<211> LENGTH: 113
<212> TYPE: PRT
<213> ORGANISM: Trypanosoma cruzi

<400> SEQUENCE: 63

Met Arg Phe Lys Lys Ser Phe Thr Cys Ile Asp Met His Thr Glu Gly
1               5                   10                  15

Glu Ala Ala Arg Ile Val Thr Ser Gly Leu Pro His Ile Pro Gly Ser
            20                  25                  30

Asn Met Ala Glu Lys Lys Ala Tyr Leu Gln Glu Asn Met Asp Tyr Leu
        35                  40                  45

Arg Arg Gly Ile Met Leu Glu Pro Arg Gly His Asp Asp Met Phe Gly
    50                  55                  60

Ala Phe Leu Phe Asp Pro Ile Glu Gly Ala Asp Leu Gly Met Val
65                  70                  75                  80

Phe Met Asp Thr Gly Gly Tyr Leu Asn Met Cys Gly His Asn Ser Ile
                85                  90                  95

Ala Ala Val Thr Ala Ala Val Glu Thr Gly Ile Val Ser Val Pro Ala
            100                 105                 110

Lys

<210> SEQ ID NO 64
<211> LENGTH: 113
<212> TYPE: PRT
<213> ORGANISM: Bacillus anthracis

<400> SEQUENCE: 64

Met Lys Val Ser Lys Val Tyr Thr Thr Ile Asp Ala His Val Ala Gly
1               5                   10                  15

Glu Pro Leu Arg Ile Ile Thr Gly Gly Val Pro Glu Ile Lys Gly Glu
            20                  25                  30

Thr Gln Leu Glu Arg Arg Trp Tyr Cys Met Glu His Leu Asp Tyr Leu
        35                  40                  45

Arg Glu Val Leu Met Tyr Glu Pro Arg Gly His His Gly Met Tyr Gly
    50                  55                  60

Cys Ile Ile Thr Pro Pro Ala Ser Ala His Ala Asp Phe Gly Val Leu
65                  70                  75                  80

Phe Met His Asn Glu Gly Trp Ser Thr Met Cys Gly His Gly Ile Ile
                85                  90                  95

Ala Val Ile Thr Val Gly Ile Glu Thr Gly Met Phe Gly Thr Lys Gln
            100                 105                 110

Lys

<210> SEQ ID NO 65
<211> LENGTH: 138
<212> TYPE: PRT
<213> ORGANISM: Trypanosoma cruzi

<400> SEQUENCE: 65

Tyr Gly Glu Val Arg Val Asp Ile Ala Phe Gly Gly Asn Phe Phe Ala
1               5                   10                  15

Ile Val Pro Ala Glu Gln Leu Gly Ile Asp Ile Ser Val Gln Asn Leu
            20                  25                  30

```
Ser Arg Leu Gln Glu Ala Gly Glu Leu Leu Arg Thr Glu Ile Asn Arg
         35                  40                  45

Ser Val Lys Val Gln His Pro Gln Leu Pro His Ile Asn Thr Val Asp
     50                  55                  60

Cys Val Glu Ile Tyr Gly Pro Thr Asn Pro Glu Ala Asn Tyr Lys
 65                  70                  75                  80

Asn Val Val Ile Phe Gly Asn Arg Gln Ala Asp Arg Ser Pro Cys Gly
                 85                  90                  95

Thr Gly Thr Ser Ala Lys Met Ala Thr Leu Tyr Ala Lys Gly Gln Leu
             100                 105                 110

Arg Ile Gly Glu Thr Phe Val Tyr Glu Ser Ile Leu Gly Ser Leu Phe
             115                 120                 125

Gln Gly Arg Val Leu Gly Glu Glu Arg Ile
             130                 135

<210> SEQ ID NO 66
<211> LENGTH: 138
<212> TYPE: PRT
<213> ORGANISM: Clostridium botulinum

<400> SEQUENCE: 66

Tyr Gly Lys Leu Thr Leu Asp Ile Ser Phe Gly Gly Ser Phe Phe Ala
 1               5                  10                  15

Met Val Asp Ala Glu Lys Val Gly Ile Asp Ile Ser Pro Ala Asn Ser
             20                  25                  30

Gln Lys Leu Asn Asp Leu Gly Met Lys Ile Val His Ala Val Asn Glu
         35                  40                  45

Gln Val Glu Ile Lys His Pro Val Leu Glu His Ile Lys Thr Val Asp
     50                  55                  60

Leu Cys Glu Phe Tyr Gly Pro Ala Lys Ser Glu Asp Ala Asp Val Gln
 65                  70                  75                  80

Asn Val Val Val Phe Gly Gln Gly Gln Val Asp Arg Ser Pro Cys Gly
                 85                  90                  95

Thr Gly Thr Ser Ala Lys Met Ala Leu Leu Tyr Ala Gln Gly Lys Met
             100                 105                 110

Lys Val Gly Glu Glu Ile Val Asn Glu Ser Ile Ile Cys Thr Lys Phe
             115                 120                 125

Lys Gly Lys Ile Leu Glu Glu Thr Lys Val
             130                 135

<210> SEQ ID NO 67
<211> LENGTH: 118
<212> TYPE: PRT
<213> ORGANISM: Trypanosoma cruzi

<400> SEQUENCE: 67

Ile Met Arg Phe Lys Lys Ser Phe Thr Cys Ile Asp Met His Thr Glu
 1               5                  10                  15

Gly Glu Ala Ala Arg Ile Val Thr Ser Gly Leu Pro His Ile Pro Gly
             20                  25                  30

Ser Asn Met Ala Glu Lys Lys Ala Tyr Leu Gln Glu Asn Met Asp Tyr
         35                  40                  45

Leu Arg Arg Gly Ile Met Leu Glu Pro Arg Gly His Asp Asp Met Phe
     50                  55                  60

Gly Ala Phe Leu Phe Asp Pro Ile Glu Glu Gly Ala Asp Leu Gly Met
 65                  70                  75                  80
```

```
Val Phe Met Asp Thr Gly Gly Tyr Leu Asn Met Cys Gly His Asn Ser
             85                  90                  95

Ile Ala Ala Val Thr Ala Ala Val Glu Thr Gly Ile Val Ser Val Pro
            100                 105                 110

Ala Lys Ala Thr Asn Val
        115

<210> SEQ ID NO 68
<211> LENGTH: 118
<212> TYPE: PRT
<213> ORGANISM: Clostridium botulinum

<400> SEQUENCE: 68

Ile Met Arg Ala Ile Lys Thr Ile Gln Thr Ile Glu Ser His Thr Met
  1               5                  10                  15

Gly Glu Pro Thr Arg Ile Val Ile Gly Gly Leu Pro Lys Val Pro Gly
             20                  25                  30

Lys Thr Met Ala Glu Lys Met Glu Tyr Leu Glu Asn Asn Asp Ser
         35                  40                  45

Leu Arg Thr Met Leu Met Ser Glu Pro Arg Gly His Asn Asp Met Phe
 50                  55                  60

Gly Ala Ile Tyr Thr Glu Pro Ala Asp Glu Thr Ala Asp Leu Gly Ile
 65                  70                  75                  80

Ile Phe Met Asp Gly Gly Tyr Leu Asn Met Cys Gly His Gly Ser
             85                  90                  95

Ile Gly Ala Ala Thr Cys Ala Val Glu Met Gly Ile Val Lys Val Glu
            100                 105                 110

Glu Pro Tyr Thr Asn Ile
        115

<210> SEQ ID NO 69
<211> LENGTH: 224
<212> TYPE: PRT
<213> ORGANISM: Trypanosoma cruzi

<400> SEQUENCE: 69

Ala Asp Leu Gly Ile Val Phe Met Asp Thr Gly Gly Tyr Leu Asn Met
  1               5                  10                  15

Cys Gly His Asn Ser Ile Ala Ala Val Thr Ala Ala Val Glu Thr Gly
             20                  25                  30

Ile Leu Ser Val Pro Ala Lys Ala Thr Asn Val Pro Val Val Leu Asp
         35                  40                  45

Thr Pro Ala Gly Leu Val Arg Gly Thr Ala His Leu Gln Ser Gly Thr
 50                  55                  60

Glu Ser Glu Val Ser Asn Ala Ser Ile Ile Asn Val Pro Ser Phe Leu
 65                  70                  75                  80

Tyr Gln Gln Asp Val Val Ile Val Leu Pro Lys Pro Tyr Gly Glu Val
             85                  90                  95

Arg Val Asp Ile Ala Phe Gly Gly Asn Phe Ala Ile Val Pro Ala
            100                 105                 110

Glu His Leu Gly Ile Asp Ile Ser Val Gln Asn Leu Ser Arg Leu Gln
        115                 120                 125

Glu Ala Gly Glu Leu Leu Arg Thr Glu Ile Asn Arg Ser Val Lys Val
        130                 135                 140

Gln His Pro Gln Leu Pro His Ile Asn Thr Val Asp Cys Val Glu Ile
145                 150                 155                 160
```

```
Tyr Gly Asn Ala Thr Asn Pro Glu Ala Lys Tyr Lys Asn Val Val Ile
                165                 170                 175

Phe Gly Asn Arg Gln Ala Asp Arg Ser Pro Cys Gly Thr Gly Thr Ser
            180                 185                 190

Ala Lys Met Ala Thr Leu Tyr Ala Lys Gly Gln Leu Arg Ile Gly Glu
        195                 200                 205

Thr Phe Val Tyr Glu Ser Ile Leu Gly Ser Leu Phe Gln Gly Arg Val
    210                 215                 220

<210> SEQ ID NO 70
<211> LENGTH: 218
<212> TYPE: PRT
<213> ORGANISM: Clostridium botulinum

<400> SEQUENCE: 70

Ala Asp Leu Gly Ile Ile Phe Met Asp Gly Gly Tyr Leu Asn Met
 1               5                  10                  15

Cys Gly His Gly Ser Ile Gly Ala Ala Thr Cys Ala Val Glu Met Gly
                20                  25                  30

Ile Val Lys Val Glu Glu Pro Tyr Thr Asn Ile Lys Leu Glu Ala Pro
            35                  40                  45

Ala Gly Met Ile Asn Ala Arg Val Lys Val Glu Asp Gly Lys Ala Lys
        50                  55                  60

Glu Thr Ser Ile Val Asn Val Pro Ala Phe Leu Tyr Lys Lys Asp Val
 65                  70                  75                  80

Glu Ile Asp Val Pro Asp Tyr Gly Lys Leu Thr Leu Asp Ile Ser Phe
                85                  90                  95

Gly Gly Ser Phe Phe Ala Met Val Asp Ala Glu Lys Val Gly Ile Asp
            100                 105                 110

Ile Ser Pro Ala Asn Ser Gln Lys Leu Asn Asp Leu Gly Met Lys Ile
        115                 120                 125

Val His Ala Val Asn Glu Gln Val Glu Ile Lys His Pro Val Leu Glu
    130                 135                 140

His Ile Lys Thr Val Asp Leu Cys Glu Phe Tyr Gly Pro Ala Lys Ser
145                 150                 155                 160

Glu Asp Ala Asp Val Gln Asn Val Val Val Phe Gly Gln Gly Gln Val
                165                 170                 175

Asp Arg Ser Pro Cys Gly Thr Gly Thr Ser Ala Lys Met Ala Leu Leu
            180                 185                 190

Tyr Ala Gln Gly Lys Met Lys Val Gly Glu Glu Ile Val Asn Glu Ser
        195                 200                 205

Ile Ile Cys Thr Lys Phe Lys Gly Lys Ile
    210                 215

<210> SEQ ID NO 71
<211> LENGTH: 72
<212> TYPE: PRT
<213> ORGANISM: Trypanosoma cruzi

<400> SEQUENCE: 71

Pro Thr Asn Pro Glu Ala Asn Tyr Lys Asn Val Val Ile Phe Gly Asn
 1               5                  10                  15

Arg Gln Ala Asp Arg Ser Pro Cys Gly Thr Gly Thr Ser Ala Lys Met
                20                  25                  30

Ala Thr Leu Tyr Ala Lys Gly Gln Leu Arg Ile Gly Glu Thr Phe Val
            35                  40                  45
```

```
Tyr Glu Ser Ile Leu Gly Ser Leu Phe Gln Gly Arg Val Leu Gly Glu
         50                  55                  60

Glu Arg Ile Pro Gly Val Lys Val
 65                  70

<210> SEQ ID NO 72
<211> LENGTH: 72
<212> TYPE: PRT
<213> ORGANISM: Aspergillus fumigatus

<400> SEQUENCE: 72

Pro Asp Asp Val Gln Gly Ala Glu Thr Gly Leu Cys Tyr Phe Ala Glu
 1               5                  10                  15

Asn Gln Ile Asp Arg Ser Pro Thr Gly Ser Cys Val Ile Ala Arg Met
             20                  25                  30

Ala Leu Ala Tyr Ala Lys Gly Leu Arg Ser Leu Gly Gln Arg Trp Ala
         35                  40                  45

Tyr Asn Ser Leu Val Ser Asn Arg Phe Gly Thr Gly Ala Phe Ser Ala
     50                  55                  60

Glu Ile Val Glu Glu Val Thr Ile
 65                  70

<210> SEQ ID NO 73
<211> LENGTH: 34
<212> TYPE: PRT
<213> ORGANISM: Trypanosoma cruzi

<400> SEQUENCE: 73

Met Ala Glu Lys Lys Ala Tyr Leu Gln Glu Asn Met Asp Tyr Leu Arg
 1               5                  10                  15

Arg Gly Ile Met Leu Glu Pro Arg Gly His Asp Asp Met Phe Gly Ala
             20                  25                  30

Phe Leu

<210> SEQ ID NO 74
<211> LENGTH: 34
<212> TYPE: PRT
<213> ORGANISM: Aspergillus fumigatus

<400> SEQUENCE: 74

Leu Leu Glu Gln Arg Asp Gln Ala Lys Gln His His Asp His Ile Arg
 1               5                  10                  15

Lys Cys Leu Met Leu Glu Pro Arg Gly His Asn Gly Met Tyr Gly Ala
             20                  25                  30

Ile Ile

<210> SEQ ID NO 75
<211> LENGTH: 29
<212> TYPE: PRT
<213> ORGANISM: Trypanosoma cruzi

<400> SEQUENCE: 75

Cys Ile Asp Met His Thr Glu Gly Glu Ala Ala Arg Ile Val Thr Ser
 1               5                  10                  15

Gly Leu Pro His Ile Pro Gly Ser Asn Met Ala Glu Lys
             20                  25

<210> SEQ ID NO 76
<211> LENGTH: 29
<212> TYPE: PRT
```

```
<213> ORGANISM: Aspergillus fumigatus

<400> SEQUENCE: 76

Cys Ile Asp Met His Thr Thr Gly Glu Pro Thr Arg Ile Ile Tyr Ser
 1               5                  10                  15

Gly Phe Pro Pro Leu Ser Gly Thr Leu Leu Glu Gln Arg
            20                  25

<210> SEQ ID NO 77
<211> LENGTH: 27
<212> TYPE: PRT
<213> ORGANISM: Trypanosoma cruzi

<400> SEQUENCE: 77

Val Asp Ile Ala Phe Gly Gly Asn Phe Phe Ala Ile Val Pro Ala Glu
 1               5                  10                  15

Gln Leu Gly Ile Asp Ile Ser Val Gln Asn Leu
            20                  25

<210> SEQ ID NO 78
<211> LENGTH: 27
<212> TYPE: PRT
<213> ORGANISM: Aspergillus fumigatus

<400> SEQUENCE: 78

Leu Asp Ile Ser Tyr Gly Gly Ala Phe Tyr Ala Ile Val Gln Ala Ser
 1               5                  10                  15

Glu Leu Gly Phe Ser Gly Gly Leu Arg Asp Leu
            20                  25

<210> SEQ ID NO 79
<211> LENGTH: 20
<212> TYPE: PRT
<213> ORGANISM: Trypanosoma cruzi

<400> SEQUENCE: 79

Ser Ser Ile Gly Ser Asn Lys Lys Ala Pro Asn Ile Ser Ser Pro Arg
 1               5                  10                  15

Gly Ser Ser Ile
            20

<210> SEQ ID NO 80
<211> LENGTH: 20
<212> TYPE: PRT
<213> ORGANISM: Aspergillus fumigatus

<400> SEQUENCE: 80

Ser Ser Val Ser Gly Arg Met Met Ala Pro Tyr Ile Pro Leu Pro Arg
 1               5                  10                  15

Gly Ser Ser Ile
            20

<210> SEQ ID NO 81
<211> LENGTH: 146
<212> TYPE: PRT
<213> ORGANISM: Trypanosoma cruzi

<400> SEQUENCE: 81

Gly Glu Val Arg Val Asp Ile Ala Phe Gly Gly Asn Phe Phe Ala Ile
 1               5                  10                  15

Val Pro Ala Glu Gln Leu Gly Ile Asp Ile Ser Val Gln Asn Leu Ser
            20                  25                  30
```

```
Arg Leu Gln Glu Ala Gly Glu Leu Leu Arg Thr Glu Ile Asn Arg Ser
            35                  40                  45

Val Lys Val Gln His Pro Gln Leu Pro His Ile Asn Thr Val Asp Cys
 50                  55                  60

Val Glu Ile Tyr Gly Pro Pro Thr Asn Pro Glu Ala Asn Tyr Lys Asn
 65                  70                  75                  80

Val Val Ile Phe Gly Asn Arg Gln Ala Asp Arg Ser Pro Cys Gly Thr
                85                  90                  95

Gly Thr Ser Ala Lys Met Ala Thr Leu Tyr Ala Lys Gly Gln Leu Arg
            100                 105                 110

Ile Gly Glu Thr Phe Val Tyr Glu Ser Ile Leu Gly Ser Leu Phe Gln
            115                 120                 125

Gly Arg Val Leu Gly Glu Arg Ile Pro Gly Val Lys Val Pro Val
    130                 135                 140

Thr Lys
145

<210> SEQ ID NO 82
<211> LENGTH: 146
<212> TYPE: PRT
<213> ORGANISM: Clostridium difficile

<400> SEQUENCE: 82

Gly Thr Val Lys Phe Asp Ile Ser Phe Gly Gly Ser Phe Phe Ala Ile
 1               5                  10                  15

Ile His Ala Ser Gln Leu Gly Leu Lys Ile Glu Pro Gln Asn Ala Gly
            20                  25                  30

Lys Leu Thr Glu Leu Ala Met Lys Leu Arg Asp Ile Ile Asn Glu Lys
            35                  40                  45

Ile Glu Ile Gln His Pro Thr Leu Ala His Ile Lys Thr Val Asp Leu
 50                  55                  60

Val Glu Ile Tyr Asp Glu Pro Thr His Pro Glu Ala Thr Tyr Lys Asn
 65                  70                  75                  80

Val Val Ile Phe Gly Gln Gly Gln Val Asp Arg Ser Pro Cys Gly Thr
                85                  90                  95

Gly Thr Ser Ala Lys Leu Ala Thr Leu His Ala Lys Gly Glu Leu Lys
            100                 105                 110

Val Gly Glu Lys Phe Val Tyr Glu Ser Ile Leu Gly Thr Leu Phe Lys
            115                 120                 125

Gly Glu Ile Val Glu Glu Thr Lys Val Ala Asp Phe Asn Ala Val Val
    130                 135                 140

Pro Lys
145

<210> SEQ ID NO 83
<211> LENGTH: 117
<212> TYPE: PRT
<213> ORGANISM: Trypanosoma cruzi

<400> SEQUENCE: 83

Met Arg Phe Lys Lys Ser Phe Thr Cys Ile Asp Met His Thr Glu Gly
 1               5                  10                  15

Glu Ala

```
Arg Arg Gly Ile Met Leu Glu Pro Arg Gly His Asp Asp Met Phe Gly
         50                  55                  60

Ala Phe Leu Phe Asp Pro Ile Glu Glu Gly Ala Asp Leu Gly Met Val
 65                  70                  75                  80

Phe Met Asp Thr Gly Gly Tyr Leu Asn Met Cys Gly His Asn Ser Ile
                 85                  90                  95

Ala Ala Val Thr Ala Ala Val Glu Thr Gly Ile Val Ser Val Pro Ala
                100                 105                 110

Lys Ala Thr Asn Val
        115

<210> SEQ ID NO 84
<211> LENGTH: 117
<212> TYPE: PRT
<213> ORGANISM: Clostridium difficile

<400> SEQUENCE: 84

Met Lys Phe Ser Arg Ser Ile Gln Ala Ile Asp Ser His Thr Ala Gly
 1               5                  10                  15

Glu Ala Thr Arg Ile Val Val Gly Gly Ile Pro Asn Ile Lys Gly Asn
                 20                  25                  30

Ser Met Pro Glu Lys Lys Glu Tyr Leu Glu Glu Asn Leu Asp Tyr Leu
             35                  40                  45

Arg Thr Ala Ile Met Leu Glu Pro Arg Gly His Asn Asp Met Phe Gly
         50                  55                  60

Ser Val Met Thr Gln Pro Cys Cys Pro Asp Ala Asp Phe Gly Ile Ile
 65                  70                  75                  80

Phe Met Asp Gly Gly Gly Tyr Leu Asn Met Cys Gly His Gly Thr Ile
                 85                  90                  95

Gly Ala Met Thr Ala Ala Ile Glu Thr Gly Val Val Pro Ala Val Glu
                100                 105                 110

Pro Val Thr His Val
        115

<210> SEQ ID NO 85
<211> LENGTH: 139
<212> TYPE: PRT
<213> ORGANISM: Trypanosoma cruzi

<400> SEQUENCE: 85

Gly Glu Val Arg Val Asp Ile Ala Phe Gly Gly As

-continued

```
Gly Arg Val Leu Gly Glu Glu Arg Ile Pro Gly
    130                 135

<210> SEQ ID NO 86
<211> LENGTH: 139
<212> TYPE: PRT
<213> ORGANISM: Brucella suis

<400> SEQUENCE: 86

Gly Pro Ile Lys Val Asp Val Ala Tyr Gly Gly Asn Phe Tyr Ala Ile
  1               5                  10                  15

Val Glu Pro Gln Glu Asn Tyr Thr Asp Met Asp Asp Tyr Ser Ala Leu
             20                  25                  30

Gln Leu Ile Ala Trp Ser Pro Val Leu Arg Gln Arg Leu Asn Glu Lys
         35                  40                  45

Tyr Lys Phe Gln His Pro Glu Leu Pro Asp Ile Asn Arg Leu Ser His
     50                  55                  60

Ile Leu Trp Thr Gly Lys Pro Lys His Pro Gln Ala His Ala Arg Asn
 65                  70                  75                  80

Ala Val Phe Tyr Gly Asp Lys Ala Ile Asp Arg Ser Pro Cys Gly Thr
                 85                  90                  95

Gly Thr Ser Ala Arg Met Ala Gln Leu Ala Ala Lys Gly Lys Leu Lys
            100                 105                 110

Pro Gly Asp Glu Phe Ile His Glu Ser Ile Ile Gly Ser Leu Phe His
        115                 120                 125

Gly Arg Val Glu Arg Ala Ala Glu Val Ala Gly
    130                 135

<210> SEQ ID NO 87
<211> LENGTH: 106
<212> TYPE: PRT
<213> ORGANISM: Trypanosoma cruzi

<400> SEQUENCE: 87

Lys Lys Ser Phe Thr Cys Ile Asp Met His Thr Glu Gly Glu Ala Ala
  1               5                  10                  15

Arg Ile Val Thr Ser Gly Leu Pro His Ile Pro Gly Ser Asn Met Ala
             20                  25                  30

Glu Lys Lys Ala Tyr Leu Gln Glu Asn Met Asp Tyr Leu Arg Arg Gly
         35                  40                  45

Ile Met Leu Glu Pro Arg Gly His Asp Asp Met Phe Gly Ala Phe Leu
     50                  55                  60

Phe Asp Pro Ile Glu Glu Gly Ala Asp Leu Gly Met Val Phe Met Asp
 65                  70                  75                  80

Thr Gly Gly Tyr Leu Asn Met Cys Gly His Asn Ser Ile Ala Ala Val
                 85                  90                  95

Thr Ala Ala Val Glu Thr Gly Ile Val Ser
            100                 105

<210> SEQ ID NO 88
<211> LENGTH: 106
<212> TYPE: PRT
<213> ORGANISM: Brucella suis

<400> SEQUENCE: 88

Arg His Ser Phe Phe Cys Val Asp Gly His Thr Cys Gly Asn Pro Val
  1               5                  10                  15
```

```
Arg Leu Val Ala Gly Gly Pro Asn Leu Asn Gly Ser Thr Met Met
             20                  25                  30

Glu Lys Arg Ala His Phe Leu Ala Glu Tyr Asp Trp Ile Arg Thr Gly
         35                  40                  45

Leu Met Phe Glu Pro Arg Gly His Asp Met Met Ser Gly Ser Ile Leu
     50                  55                  60

Tyr Pro Pro Thr Arg Pro Asp Cys Asp Val Ala Val Leu Phe Ile Glu
 65                  70                  75                  80

Thr Ser Gly Cys Leu Pro Met Cys Gly His Gly Thr Ile Gly Thr Val
                 85                  90                  95

Thr Met Ala Ile Glu Gln Gly Leu Val Thr
            100                 105
```

<210> SEQ ID NO 89
<211> LENGTH: 109
<212> TYPE: PRT
<213> ORGANISM: Trypanosoma cruzi

<400> SEQUENCE: 89

```
Met Arg Phe Lys Lys Ser Phe Thr Cys Ile Asp Met His Thr Glu Gly
 1               5                  10                  15

Glu Ala Ala Arg Ile Val Thr Ser Gly Leu Pro His Ile Pro Gly Ser
             20                  25                  30

Asn Met Ala Glu Lys Lys Ala Tyr Leu Gln Glu Asn Met Asp Tyr Leu
         35                  40                  45

Arg Arg Gly Ile Met Leu Glu Pro Arg Gly His Asp Asp Met Phe Gly
     50                  55                  60

Ala Phe Leu Phe Asp Pro Ile Glu Gly Ala Asp Leu Gly Met Val
 65                  70                  75                  80

Phe Met Asp Thr Gly Gly Tyr Leu Asn Met Cys Gly His Asn Ser Ile
                 85                  90                  95

Ala Ala Val Thr Ala Ala Val Glu Thr Gly Ile Val Ser
            100                 105
```

<210> SEQ ID NO 90
<211> LENGTH: 109
<212> TYPE: PRT
<213> ORGANISM: Rhodobacter sphaeroides

<400> SEQUENCE: 90

```
Met Arg Val Gln Asp Val Tyr Asn Val Ile Tyr Thr His Thr Glu Gly
 1               5                  10                  15

Glu Pro Leu Cys Ile Ile Tyr Ser Gly Val Pro Tyr Pro Ala Gly Ser
             20                  25                  30

Thr Ile Leu Glu Lys Arg Ala Phe Leu Glu Glu Asn Tyr Asp Trp Leu
         35                  40                  45

Arg Lys Ala Leu Met Arg Glu Pro Arg Gly His Ala Asp Met Phe Gly
     50                  55                  60

Val Phe Leu Thr Pro Pro Ser Ser Arg Asp Tyr Asp Ala Gly Leu Ile
 65                  70                  75                  80

Tyr Ile Asp Gly Lys Glu Tyr Ser His Met Cys Gly His Gly Thr Ile
                 85                  90                  95

Ala Val Ala Met Ala Met Val Ala Asn Gly Leu Val Ala
            100                 105
```

<210> SEQ ID NO 91
<211> LENGTH: 47

<212> TYPE: PRT
<213> ORGANISM: Trypanosoma cruzi

<400> SEQUENCE: 91

```
Lys Val Gln His Pro Gln Leu Pro His Ile As

```
Ala Ala Cys Ile Leu Glu Pro Arg Gly Ser Asp Val Leu Val Gly Ala
         50                  55                  60

Leu Leu Cys Glu Pro Val Ser Ala Gly Ala Ala Gly Val Ile Phe
 65                  70                  75                  80

Phe Asn Asn Ala Gly Tyr Leu Gly Met Cys Gly His Gly Thr Ile Gly
                 85                  90                  95

Leu Val Arg Thr Leu His His Met Gly Arg Ile Gly Pro Gly Val His
             100                 105                 110

Arg Ile Glu Thr Pro Val
             115
```

<210> SEQ ID NO 95
<211> LENGTH: 63
<212> TYPE: PRT
<213> ORGANISM: Trypanosoma cruzi

<400> SEQUENCE: 95

```
Asn Pro Glu Ala Asn Tyr Lys Asn Val Val Ile Phe Gly Asn Arg Gln
 1               5                  10                  15

Ala Asp Arg Ser Pro Cys Gly Thr Gly Thr Ser Ala Lys Met Ala Thr
             20                  25                  30

Leu Tyr Ala Lys Gly Gln Leu Arg Ile Gly Glu Thr Phe Val Tyr Glu
         35                  40                  45

Ser Ile Leu Gly Ser Leu Phe Gln Gly Arg Val Leu Gly Glu Glu
     50                  55                  60
```

<210> SEQ ID NO 96
<211> LENGTH: 63
<212> TYPE: PRT
<213> ORGANISM: Burkholderia pseudomallei

<400> SEQUENCE: 96

```
Asp Pro Glu Tyr Asp Ser Arg Ser Phe Val Leu Cys Pro Gly His Ala
 1               5                  10                  15

Tyr Asp Arg Ser Pro Cys Gly Thr Gly Thr Ser Ala Lys Leu Ala Cys
             20                  25                  30

Leu Ala Ala Asp Gly Lys Leu Ala Ala Gly Val Thr Trp Arg Gln Ala
         35                  40                  45

Ser Val Ile Gly Ser Val Phe Ser Ala Ser Tyr Ala Ala Ala Glu
     50                  55                  60
```

<210> SEQ ID NO 97
<211> LENGTH: 118
<212> TYPE: PRT
<213> ORGANISM: Trypanosoma cruzi

<400> SEQUENCE: 97

```
Arg Phe Lys Lys Ser Phe Thr Cys Ile Asp Met His Thr Glu Gly Glu
 1               5                  10                  15

Ala Ala Arg Ile Val Thr Ser Gly Leu Pro His Ile Pro Gly Ser Asn
             20                  25                  30

Met Ala Glu Lys Lys Ala Tyr Leu Gln Glu Asn Met Asp Tyr Leu Arg
         35                  40                  45

Arg Gly Ile Met Leu Glu Pro Arg Gly His Asp Met Phe Gly Ala
         50                  55                  60

Phe Leu Phe Asp Pro Ile Glu Glu Gly Ala Asp Leu Gly Met Val Phe
 65                  70                  75                  80
```

```
Met Asp Thr Gly Gly Tyr Leu Asn Met Cys Gly His Asn Ser Ile Ala
                85                  90                  95

Ala Val Thr Ala Ala Val Glu Thr Gly Ile Val Ser Val Pro Ala Lys
            100                 105                 110

Ala Thr Asn Val Pro Val
        115
```

<210> SEQ ID NO 98
<211> LENGTH: 118
<212> TYPE: PRT
<213> ORGANISM: Burkholderia mallei

<400> SEQUENCE: 98

```
Arg Asp Met Lys His Ile His Ile Ile Asp Ser His Thr Gly Gly Glu
 1               5                  10                  15

Pro Thr Arg Val Val Val Ser Gly Phe Pro Ala Leu Gly Gly Gly Thr
            20                  25                  30

Met Ala Glu Arg Leu Ala Val Leu Ala Arg Glu His Asp Arg Tyr Arg
        35                  40                  45

Ala Ala Cys Ile Leu Glu Pro Arg Gly Ser Asp Val Leu Val Gly Ala
    50                  55                  60

Leu Leu Cys Glu Pro Val Ser Ala Gly Ala Ala Gly Val Ile Phe
65                  70                  75                  80

Phe Asn Asn Ala Gly Tyr Leu Gly Met Cys Gly His Gly Thr Ile Gly
                85                  90                  95

Leu Val Arg Thr Leu His His Met Gly Arg Ile Gly Pro Gly Val His
            100                 105                 110

Arg Ile Glu Thr Pro Val
        115
```

<210> SEQ ID NO 99
<211> LENGTH: 63
<212> TYPE: PRT
<213> ORGANISM: Trypanosoma cruzi

<400> SEQUENCE: 99

```
Asn Pro Glu Ala Asn Tyr Lys Asn Val Val Ile Phe Gly Asn Arg Gln
 1               5                  10                  15

Ala Asp Arg Ser Pro Cys Gly Thr Gly Thr Ser Ala Lys Met Ala Thr
            20                  25                  30

Leu Tyr Ala Lys Gly Gln Leu Arg Ile Gly Glu Thr Phe Val Tyr Glu
        35                  40                  45

Ser Ile Leu Gly Ser Leu Phe Gln Gly Arg Val Leu Gly Glu Glu
    50                  55                  60
```

<210> SEQ ID NO 100
<211> LENGTH: 63
<212> TYPE: PRT
<213> ORGANISM: Burkholderia mallei

<400> SEQUENCE: 100

```
Asp Pro Glu Tyr Asp Ser Arg Ser Phe Val Leu Cys Pro Gly His Ala
 1               5                  10                  15

Tyr Asp Arg Ser Pro Cys Gly Thr Gly Thr Ser Ala Lys Leu Ala Cys
            20                  25                  30

Leu Ala Ala Asp Gly Lys Leu Val Ala Gly Val Thr Trp Arg Gln Ala
        35                  40                  45

Ser Val Ile Gly Ser Val Phe Ser Ala Ser Tyr Ala Ala Ala Glu
```

```
              50                  55                  60

<210> SEQ ID NO 101
<211> LENGTH: 115
<212> TYPE: PRT
<213> ORGANISM: Trypanosoma cruzi

<400> SEQUENCE: 101

Lys Ser Phe Thr Cys Ile Asp Met His Thr Glu Gly Glu Ala Ala Arg
  1               5                  10                  15

Ile Val Thr Ser Gly Leu Pro His Ile Pro Gly Ser Asn Met Ala Glu
             20                  25                  30

Lys Lys Ala Tyr Leu Gln Glu Asn Met Asp Tyr Leu Arg Arg Gly Ile
         35                  40                  45

Met Leu Glu Pro Arg Gly His Asp Asp Met Phe Gly Ala Phe Leu Phe
     50                  55                  60

Asp Pro Ile Glu Glu Gly Ala Asp Leu Gly Met Val Phe Met Asp Thr
 65                  70                  75                  80

Gly Gly Tyr Leu Asn Met Cys Gly His Asn Ser Ile Ala Ala Val Thr
                 85                  90                  95

Ala Ala Val Glu Thr Gly Ile Val Ser Val Pro Ala Lys Ala Thr Asn
            100                 105                 110

Val Pro Val
        115

<210> SEQ ID NO 102
<211> LENGTH: 115
<212> TYPE: PRT
<213> ORGANISM: Pseudomonas putida

<400> SEQUENCE: 102

Lys Gln Ile His Val Ile Asp Ser His Thr Gly Gly Glu Pro Thr Arg
  1               5                  10                  15

Leu Val Met Lys Gly Phe Pro Gln Leu Arg Gly Arg Ser Met Ala Glu
             20                  25                  30

Gln Arg Asp Glu Leu Arg Glu Leu His Asp Arg Trp Arg Arg Ala Cys
         35                  40                  45

Leu Leu Glu Pro Arg Gly Asn Asp Val Leu Val Gly Ala Leu Tyr Cys
     50                  55                  60

Pro Pro Val Ser Ala Asp Ala Thr Cys Gly Val Ile Phe Phe Asn Asn
 65                  70                  75                  80

Ala Gly Tyr Leu Asn Met Cys Gly His Gly Thr Ile Gly Leu Val Ala
                 85                  90                  95

Ser Leu Gln His Met Gly Leu Ile Thr Pro Gly Val His Lys Ile Asp
            100                 105                 110

Thr Pro Val
        115

<210> SEQ ID NO 103
<211> LENGTH: 58
<212> TYPE: PRT
<213> ORGANISM: Trypanosoma cruzi

<400> SEQUENCE: 103

Asn Pro Glu Ala Asn Tyr Lys Asn Val Val Ile Phe Gly Asn Arg Gln
  1               5                  10                  15

Ala Asp Arg Ser Pro Cys Gly Thr Gly Thr Ser Ala Lys Met Ala Thr
             20                  25                  30
```

-continued

Leu Tyr Ala Lys Gly Gln Leu Arg Ile Gly Glu Thr Phe Val Tyr Glu
            35                  40                  45

Ser Ile Leu Gly Ser Leu Phe Gln Gly Arg
        50                  55

<210> SEQ ID NO 104
<211> LENGTH: 58
<212> TYPE: PRT
<213> ORGANISM: Pseudomonas putida

<400> SEQUENCE: 104

Asp Pro Asn Ala Asp Ser Arg Asn Phe Val Met Cys Pro Gly Lys Ala
  1               5                  10                  15

Tyr Asp Arg Ser Pro Cys Gly Thr Gly Thr Ser Ala Lys Leu Ala Cys
             20                  25                  30

Leu Ala Ala Asp Gly Lys Leu Ala Glu Gly Gln Thr Trp Val Gln Ala
            35                  40                  45

Ser Ile Thr Gly Ser Gln Phe His Gly Arg
        50                  55

<210> SEQ ID NO 105
<211> LENGTH: 180
<212> TYPE: PRT
<213> ORGANISM: Trypanosoma cruzi

<400> SEQUENCE: 105

Ser Gly Leu Pro His Ile Pro Gly Ser Asn Met Ala Glu Lys Lys Ala
  1               5                  10                  15

Tyr Leu Gln Glu Asn Met Asp Tyr Leu Arg Arg Gly Ile Met Leu Glu
             20                  25                  30

Pro Arg Gly His Asp Asp Met Phe Gly Ala Phe Leu Phe Asp Pro Ile
            35                  40                  45

Glu Glu Gly Ala Asp Leu Gly Ile Val Phe Met Asp Thr Gly Gly Tyr
        50                  55                  60

Leu Asn Met Cys Gly His Asn Ser Ile Ala Ala Val Thr Ala Ala Val
 65                  70                  75                  80

Glu Thr Gly Ile Val Ser Val Pro Ala Lys Ala Thr Asn Val Pro Val
                 85                  90                  95

Val Leu Asp Thr Pro Ala Gly Leu Val Arg Gly Thr Ala His Leu Gln
            100                 105                 110

Ser Gly Thr Glu Ser Glu Val Ser Asn Ala Ser Ile Ile Asn Val Pro
        115                 120                 125

Ser Phe Leu Tyr Gln Gln Asp Val Val Val Leu Pro Lys Pro Tyr
    130                 135                 140

Gly Glu Val Arg Val Asp Ile Ala Phe Gly Gly Asn Phe Phe Ala Ile
145                 150                 155                 160

Val Pro Ala Glu Gln Leu Gly Ile Asp Ile Ser Val Gln Asn Leu Ser
                165                 170                 175

Arg Leu Gln Glu
        180

<210> SEQ ID NO 106
<211> LENGTH: 164
<212> TYPE: PRT
<213> ORGANISM: Leishmania major

<400> SEQUENCE: 106

```
Thr Gly Phe Pro Glu Leu Ala Gly Glu Thr Ile Ala Asp Lys Leu Asp
 1               5                  10                  15

Asn Leu Arg Thr Gln His Asp Gln Trp Arg Arg Ala Cys Leu Leu Glu
             20                  25                  30

Pro Arg Gly Asn Asp Val Leu Val Gly Ala Leu Tyr Cys Ala Pro Val
         35                  40                  45

Ser Ala Asp Ala Thr Cys Gly Val Ile Phe Phe Asn Asn Ala Gly Tyr
     50                  55                  60

Leu Gly Met Cys Gly His Gly Thr Ile Gly Leu Val Ala Ser Leu His
65                  70                  75                  80

His Leu Gly Arg Ile Ala Pro Gly Val His Lys Ile Asp Thr Pro Val
                 85                  90                  95

Gly Pro Val Ser Ala Thr Leu His Ala Asp Gly Ala Val Thr Leu Arg
            100                 105                 110

Asn Val Pro Ala Tyr Arg Tyr Arg Gln Gln Val Pro Val Asp Val Pro
        115                 120                 125

Gly His Gly Arg Val Tyr Gly Asp Ile Ala Trp Gly Gly Asn Trp Phe
    130                 135                 140

Phe Leu Val Ser Asp His Gly Gln Ala Leu Gln Met Asp Asn Val Glu
145                 150                 155                 160

Ala Leu Thr Asp

<210> SEQ ID NO 107
<211> LENGTH: 68
<212> TYPE: PRT
<213> ORGANISM: Trypanosoma cruzi

<400> SEQUENCE: 107

Pro Thr Asn Pro Glu Ala Asn Tyr Lys Asn Val Val Ile Phe Gly Asn
 1               5                  10                  15

Arg Gln Ala Asp Arg Ser Pro Cys Gly Thr Gly Thr Ser Ala Lys Met
             20                  25                  30

Ala Thr Leu Tyr Ala Lys Gly Gln Leu Arg Ile Gly Glu Thr Phe Val
         35                  40                  45

Tyr Glu Ser Ile Leu Gly Ser Leu Phe Gln Gly Arg Val Leu Gly Glu
     50                  55                  60

Glu Arg Ile Pro
65

<210> SEQ ID NO 108
<211> LENGTH: 68
<212> TYPE: PRT
<213> ORGANISM: Leishmania major

<400> SEQUENCE: 108

Pro Thr Thr Pro Thr Pro Thr Ala Thr Ser Ser Cys Ala Gln Gly Lys
 1               5                  10                  15

Ala Tyr Asp Arg Ser Pro Cys Gly Thr Gly Thr Asn Ala Lys Leu Ala
             20                  25                  30

Cys Leu Ala Gly Asp Ser Lys Leu Ala Ala Gly Glu Pro Trp Leu Gln
         35                  40                  45

Val Thr Ile Thr Cys Arg Gln Phe Lys Arg Ser Tyr Gln Trp Glu Cys
     50                  55                  60

Lys Arg Val Pro
65
```

```
<210> SEQ ID NO 109
<211> LENGTH: 28
<212> TYPE: PRT
<213> ORGANISM: Trypanosoma cruzi

<400> SEQUENCE: 109

Val Thr Ala Glu Ile Thr Gly Lys Ala Phe Ile Met Gly Phe Asn Thr
1               5                   10                  15

Met Leu Phe Asp Pro Thr Asp Pro Phe Lys Asn Gly
            20                  25

<210> SEQ ID NO 110
<211> LENGTH: 27
<212> TYPE: PRT
<213> ORGANISM: Leishmania major

<400> SEQUENCE: 110

Val Pro Pro Ser Ile Thr Arg Arg Ala Tyr Met Thr Ala Asp Ser Thr
1               5                   10                  15

Leu Leu Ile Asp Gln Asp Pro Phe Ala Trp Gly
            20                  25

<210> SEQ ID NO 111
<211> LENGTH: 182
<212> TYPE: PRT
<213> ORGANISM: Trypanosoma cruzi

<400> SEQUENCE: 111

Val Thr Ser Gly Leu Pro His Ile Pro Gly Ser Asn Met Ala Glu Lys
1               5                   10                  15

Lys Ala Tyr Leu Gln Glu Asn Met Asp Tyr Leu Arg Arg Gly Ile Met
            20                  25                  30

Leu Glu Pro Arg Gly His Asp Asp Met Phe Gly Ala Phe Leu Phe Asp
        35                  40                  45

Pro Ile Glu Glu Gly Ala Asp Leu Gly Ile Val Phe Met Asp Thr Gly
    50                  55                  60

Gly Tyr Leu Asn Met Cys Gly His Asn Ser Ile Ala Ala Val Thr Ala
65                  70                  75                  80

Ala Val Glu Thr Gly Ile Val Ser Val Pro Ala Lys Ala Thr Asn Val
                85                  90                  95

Pro Val Val Leu Asp Thr Pro Ala Gly Leu Val Arg Gly Thr Ala His
            100                 105                 110

Leu Gln Ser Gly Thr Glu Ser Glu Val Ser Asn Ala Ser Ile Ile Asn
        115                 120                 125

Val Pro Ser Phe Leu Tyr Gln Gln Asp Val Val Val Leu Pro Lys
    130                 135                 140

Pro Tyr Gly Glu Val Arg Val Asp Ile Ala Phe Gly Gly Asn Phe Phe
145                 150                 155                 160

Ala Ile Val Pro Ala Glu Gln Leu Gly Ile Asp Ile Ser Val Gln Asn
                165                 170                 175

Leu Ser Arg Leu Gln Glu
            180

<210> SEQ ID NO 112
<211> LENGTH: 166
<212> TYPE: PRT
<213> ORGANISM: Leishmania major

<400> SEQUENCE: 112
```

```
Val Met Thr Gly Phe Pro Glu Leu Ala Gly Glu Thr Ile Ala Asp Lys
1               5                   10                  15

Leu Asp Asn Leu Arg Thr Gln His Asp Gln Trp Arg Arg Ala Cys Leu
            20                  25                  30

Leu Glu Pro Arg Gly Asn Asp Val Leu Val Gly Ala Leu Tyr Cys Ala
        35                  40                  45

Pro Val Ser Ala Asp Ala Thr Cys Gly Val Ile Phe Phe Asn Asn Ala
    50                  55                  60

Gly Tyr Leu Gly Met Cys Gly His Gly Thr Ile Gly Leu Val Ala Ser
65                  70                  75                  80

Leu His His Leu Gly Arg Ile Ala Pro Gly Val His Lys Ile Asp Thr
            85                  90                  95

Pro Val Gly Pro Val Ser Ala Thr Leu His Ala Asp Gly Ala Val Thr
        100                 105                 110

Leu Arg Asn Val Pro Ala Tyr Arg Tyr Arg Gln Gln Val Pro Val Asp
        115                 120                 125

Val Pro Gly His Gly Arg Val Tyr Gly Asp Ile Ala Trp Gly Gly Asn
    130                 135                 140

Trp Phe Phe Leu Val Ser Asp His Gly Gln Ala Leu Gln Met Asp Asn
145                 150                 155                 160

Val Glu Ala Leu Thr Asp
                165

<210> SEQ ID NO 113
<211> LENGTH: 142
<212> TYPE: PRT
<213> ORGANISM: Trypanosoma cruzi

<400> SEQUENCE: 113

Arg Ile Val Thr Ser Gly Leu Pro His Ile Pro Gly Ser Asn Met Ala
1               5                   10                  15

Glu Lys Lys Ala Tyr Leu Gln Glu Asn Met Asp Tyr Leu Arg Arg Gly
            20                  25                  30

Ile Met Leu Glu Pro Arg Gly His Asp Asp Met Phe Gly Ala Phe Leu
        35                  40                  45

Phe Asp Pro Ile Glu Glu Gly Ala Asp Leu Gly Ile Val Phe Met Asp
    50                  55                  60

Thr Gly Gly Tyr Leu Asn Met Cys Gly His Asn Ser Ile Ala Ala Val
65                  70                  75                  80

Thr Ala Ala Val Glu Thr Gly Ile Leu Ser Val Pro Ala Lys Ala Thr
            85                  90                  95

Asn Val Pro Val Val Leu Asp Thr Pro Ala Gly Leu Val Arg Gly Thr
        100                 105                 110

Ala His Leu Gln Ser Gly Thr Glu Ser Glu Val Ser Asn Ala Ser Ile
        115                 120                 125

Ile Asn Val Pro Ser Phe Leu Tyr Gln Gln Asp Val Val Ile
    130                 135                 140

<210> SEQ ID NO 114
<211> LENGTH: 137
<212> TYPE: PRT
<213> ORGANISM: Trypanosoma brucei

<400> SEQUENCE: 114

Arg Ile Ile Thr Gly Gly Val Pro Glu Ile Lys Gly Glu Thr Gln Leu
1               5                   10                  15
```

-continued

```
Glu Arg Arg Ala Tyr Cys Met Glu His Leu Asp Tyr Leu Arg Glu Ile
            20                  25                  30

Leu Met Tyr Glu Pro Arg Gly His His Gly Met Tyr Gly Cys Ile Ile
        35                  40                  45

Thr Pro Pro Ala Ser Ala His Ala Asp Phe Gly Val Leu Phe Met His
    50                  55                  60

Asn Glu Gly Trp Ser Thr Met Cys Gly His Gly Ile Ile Ala Val Ile
65                  70                  75                  80

Thr Val Gly Ile Glu Thr Gly Met Phe Glu Val Lys Gly Glu Lys Gln
                85                  90                  95

Asn Phe Ile Ile Asp Ser Pro Ala Gly Glu Val Ile Ala Tyr Ala Lys
            100                 105                 110

Tyr Asn Gly Ser Glu Val Glu Ser Val Ser Phe Glu Asn Val Pro Ser
        115                 120                 125

Phe Val Tyr Lys Lys Asp Val Pro Ile
    130                 135

<210> SEQ ID NO 115
<211> LENGTH: 140
<212> TYPE: PRT
<213> ORGANISM: Trypanosoma cruzi

<400> SEQUENCE: 115

Val Thr Ser Gly Leu Pro His Ile Pro Gly Ser Asn Met Ala Glu Lys
1               5                   10                  15

Lys Ala Tyr Leu Gln Glu Asn Met Asp Tyr Leu Arg Arg Gly Ile Met
            20                  25                  30

Leu Glu Pro Arg Gly His Asp Asp Met Phe Gly Ala Phe Leu Phe Asp
        35                  40                  45

Pro Ile Glu Glu Gly Ala Asp Leu Gly Ile Val Phe Met Asp Thr Gly
    50                  55                  60

Gly Tyr Leu Asn Met Cys Gly His Asn Ser Ile Ala Ala Val Thr Ala
65                  70                  75                  80

Ala Val Glu Thr Gly Ile Leu Ser Val Pro Ala Lys Ala Thr Asn Val
                85                  90                  95

Pro Val Val Leu Asp Thr Pro Ala Gly Leu Val Arg Gly Thr Ala His
            100                 105                 110

Leu Gln Ser Gly Thr Glu Ser Glu Val Ser Asn Ala Ser Ile Ile Asn
        115                 120                 125

Val Pro Ser Phe Leu Tyr Gln Gln Asp Val Val Ile
    130                 135                 140

<210> SEQ ID NO 116
<211> LENGTH: 135
<212> TYPE: PRT
<213> ORGANISM: Trypanosoma brucei

<400> SEQUENCE: 116

Ile Thr Gly Gly Val Pro Glu Ile Lys Gly Glu Thr Gln Leu Glu Arg
1               5                   10                  15

Arg Ala Tyr Cys Met Glu His Leu Asp Tyr Leu Arg Glu Ile Leu Met
            20                  25                  30

Tyr Glu Pro Arg Gly His His Gly Met Tyr Gly Cys Ile Ile Thr Pro
        35                  40                  45

Pro Ala Ser Ala His Ala Asp Phe Gly Val Leu Phe Met His Asn Glu
    50                  55                  60
```

-continued

Gly Trp Ser Thr Met Cys His Gly Ile Ile Ala Val Ile Thr Val
65                  70                  75                  80

Gly Ile Glu Thr Gly Met Phe Glu Val Lys Gly Glu Lys Gln Asn Phe
                85                  90                  95

Ile Ile Asp Ser Pro Ala Gly Glu Val Ile Ala Tyr Ala Lys Tyr Asn
            100                 105                 110

Gly Ser Glu Val Glu Ser Val Ser Phe Glu Asn Val Pro Ser Phe Val
        115                 120                 125

Tyr Lys Lys Asp Val Pro Ile
    130                 135

<210> SEQ ID NO 117
<211> LENGTH: 103
<212> TYPE: PRT
<213> ORGANISM: Trypanosoma cruzi

<400> SEQUENCE: 117

Phe Gly Gly Asn Phe Phe Ala Ile Val Pro Ala Glu Gln Leu Gly Ile
1               5                   10                  15

Asp Ile Ser Val Gln Asn Leu Ser Arg Leu Gln Glu Ala Gly Glu Leu
            20                  25                  30

Leu Arg Thr Glu Ile Asn Arg Ser Val Lys Val Gln His Pro Gln Leu
        35                  40                  45

Pro His Ile Asn Thr Val Asp Cys Val Glu Ile Tyr Gly Pro Pro Thr
    50                  55                  60

Asn Pro Glu Ala Asn Tyr Lys Asn Val Val Ile Phe Gly Asn Arg Gln
65                  70                  75                  80

Ala Asp Arg Ser Pro Cys Gly Thr Gly Thr Ser Ala Lys Met Ala Thr
                85                  90                  95

Leu Tyr Ala Lys Gly Gln Leu
            100

<210> SEQ ID NO 118
<211> LENGTH: 95
<212> TYPE: PRT
<213> ORGANISM: Trypanosoma congolense

<400> SEQUENCE: 118

Trp Gly Gly Asn Trp Phe Phe Leu Val Ser Asp His Gly His Glu Leu
1               5                   10                  15

Gln Met Asp Asn Val Glu Ala Leu Thr Asp Tyr Thr Trp Ala Met Leu
            20                  25                  30

Asn Ala Leu Glu Ala Gln Gly Ile Arg Gly Ala Asp Gly Ala Leu Ile
        35                  40                  45

Asp His Ile Glu Leu Phe Ala Asp Asp Ala His Ala Asp Ser Arg Asn
    50                  55                  60

Phe Val Met Cys Pro Gly Lys Ala Tyr Asp Arg Ser Pro Cys Gly Thr
65                  70                  75                  80

Gly Thr Ser Ala Lys Leu Ala Cys Leu Ala Asp Ala Lys Leu
                85                  90                  95

<210> SEQ ID NO 119
<211> LENGTH: 55
<212> TYPE: PRT
<213> ORGANISM: Trypanosoma cruzi

<400> SEQUENCE: 119

Asn Val Pro Ser Phe Leu Tyr Gln Gln Asp Val Val Val Val Leu Pro

-continued

```
                1               5                  10                  15
Lys Pro Tyr Gly Glu Val Arg Val Asp Ile Ala Phe Gly Gly Asn Phe
                        20                  25                  30

Phe Ala Ile Val Pro Ala Glu Gln Leu Gly Ile Asp Ile Ser Val Gln
            35                  40                  45

Asn Leu Ser Arg Leu Gln Glu
        50                  55
```

<210> SEQ ID NO 120
<211> LENGTH: 52
<212> TYPE: PRT
<213> ORGANISM: Trypanosoma congolense

<400> SEQUENCE: 120

```
His Val Pro Ala Tyr Arg Tyr Arg Lys Gln Val Pro Val Glu Val Pro
 1               5                  10                  15

Gly His Gly Val Val Leu Gly Asp Ile Ala Trp Gly Gly Asn Trp Phe
                20                  25                  30

Phe Leu Val Ser Asp His Gly His Glu Leu Gln Met Asp Asn Val Glu
            35                  40                  45

Ala Leu Thr Asp
        50
```

<210> SEQ ID NO 121
<211> LENGTH: 117
<212> TYPE: PRT
<213> ORGANISM: Trypanosoma cruzi

<400> SEQUENCE: 121

```
Leu Pro Lys Pro Tyr Gly Glu Val Arg Val Asp Ile Ala Phe Gly Gly
 1               5                  10                  15

Asn Phe Phe Ala Ile Val Pro Ala Glu Gln Leu Gly Ile Asp Ile Ser
                20                  25                  30

Val Gln Asn Leu Ser Arg Leu Gln Glu Ala Gly Glu Leu Leu Arg Thr
            35                  40                  45

Glu Ile Asn Arg Ser Val Lys Val Gln His Pro Gln Leu Pro His Ile
        50                  55                  60

Asn Thr Val Asp Cys Val Glu Ile Tyr Gly Pro Pro Thr Asn Pro Glu
 65                  70                  75                  80

Ala Asn Tyr Lys Asn Val Val Ile Phe Gly Asn Arg Gln Ala Asp Arg
                85                  90                  95

Ser Pro Cys Gly Thr Gly Thr Ser Ala Lys Met Ala Thr Leu Tyr Ala
            100                 105                 110

Lys Gly Gln Leu Arg
        115
```

<210> SEQ ID NO 122
<211> LENGTH: 116
<212> TYPE: PRT
<213> ORGANISM: Trypanosoma vivax

<400> SEQUENCE: 122

```
Leu Pro His Pro Tyr Gly Lys Tyr Ala Val Ile Ser Phe Gly Gly Ser
 1               5                  10                  15

Phe Phe Ala Leu Ile Asp Ala Ala Gln Leu Gln Leu Thr Val Asp Lys
                20                  25                  30

Gly His Leu Ser Thr Leu Gln His Val Gly Gly Leu Leu Arg Asp Thr
            35                  40                  45
```

```
Leu Asn Arg Asn Val Ser Val Gln His Pro Gln Leu Pro His Ile Asn
    50                  55                  60

Arg Ile Asp Cys Val Glu Ile Tyr Asp Pro Thr Asn Pro Ala Ala
65                  70                  75                  80

Ser Cys Lys Asn Val Val Ile Phe Gly Asn Ser Gln Val Asp Arg Ser
                85                  90                  95

Pro Cys Gly Thr Gly Thr Cys Ala Lys Met Ala Leu Tyr Ala Lys
            100                 105                 110

Gly Lys Leu Lys
        115

<210> SEQ ID NO 123
<211> LENGTH: 106
<212> TYPE: PRT
<213> ORGANISM: Trypanosoma cruzi

<400> SEQUENCE: 123

Arg Glu Ile Met Arg Phe Lys Lys Ser Phe Thr Cys Ile Asp Met His
1               5                   10                  15

Thr Glu Gly Glu Ala Ala Arg Ile Val Thr Ser Gly Leu Pro His Ile
            20                  25                  30

Pro Gly Ser Asn Met Ala Glu Lys Lys Ala Tyr Leu Gln Glu Asn Met
        35                  40                  45

Asp Tyr Leu Arg Arg Gly Ile Met Leu Glu Pro Arg Gly His Asp Asp
    50                  55                  60

Met Phe Gly Ala Phe Leu Phe Asp Pro Ile Glu Glu Gly Ala Asp Leu
65                  70                  75                  80

Gly Met Val Phe Met Asp Thr Gly Gly Tyr Leu Asn Met Cys Gly His
                85                  90                  95

Asn Ser Ile Ala Ala Val Thr Ala Ala Val
            100                 105

<210> SEQ ID NO 124
<211> LENGTH: 106
<212> TYPE: PRT
<213> ORGANISM: Trypanosoma vivax

<400> SEQUENCE: 124

Arg Val Val Met Gln Phe Thr Gly Thr Met Thr Cys Ile Asp Met His
1               5                   10                  15

Thr Ala Gly Glu Pro Ala Arg Ile Val Thr Ser Gly Phe Pro Asn Ile
            20                  25                  30

Pro Gly Ala Ser Leu Val Glu Lys Arg Asp His Leu Gln Arg His Met
        35                  40                  45

Asp His Ile Arg Arg Arg Val Met Leu Glu Pro Arg Gly His Asp Asn
    50                  55                  60

Met Phe Gly Ala Phe Leu Phe Tyr Pro Leu Thr Asp Gly Ala Asp Phe
65                  70                  75                  80

Ser Val Ile Phe Met Asp Ala Gly Gly Tyr Leu Asn Met Cys Gly His
                85                  90                  95

Asn Ser Ile Ala Ile Ala Thr Ala Ala Val
            100                 105

<210> SEQ ID NO 125
<211> LENGTH: 357
<212> TYPE: PRT
<213> ORGANISM: Trypanosoma cruzi
```

<400> SEQUENCE: 125

| | | | | | | | | | | | | | | |
|---|---|---|---|---|---|---|---|---|---|---|---|---|---|---|
|Lys|Arg|Glu|Ile|Met|Arg|Phe|Lys|Lys|Ser|Phe|Thr|Cys|Ile|Asp|Met|
|1| | | |5| | | | |10| | | | |15| |

His Thr Glu Gly Glu Ala Ala Arg Ile Val Thr Ser Gly Leu Pro His
            20                  25                  30

Ile Pro Gly Ser Asn Met Ala Glu Lys Lys Ala Tyr Leu Gln Glu Asn
        35                  40                  45

Met Asp Tyr Leu Arg Arg Gly Ile Met Leu Glu Pro Arg Gly His Asp
 50                  55                  60

Asp Met Phe Gly Ala Phe Leu Phe Asp Pro Ile Glu Glu Gly Ala Asp
 65                  70                  75                  80

Leu Gly Met Val Phe Met Asp Thr Gly Gly Tyr Leu Asn Met Cys Gly
                85                  90                  95

His Asn Ser Ile Ala Ala Val Thr Ala Ala Val Glu Thr Gly Ile Val
            100                 105                 110

Ser Val Pro Ala Lys Ala Thr Asn Val Pro Val Val Leu Asp Thr Pro
        115                 120                 125

Ala Gly Leu Val Arg Gly Thr Ala His Leu Gln Ser Gly Thr Glu Ser
    130                 135                 140

Glu Val Ser Asn Ala Ser Ile Ile Asn Val Pro Ser Phe Leu Tyr Gln
145                 150                 155                 160

Gln Asp Val Val Val Leu Pro Lys Pro Tyr Gly Glu Val Arg Val
                165                 170                 175

Asp Ile Ala Phe Gly Gly Asn Phe Phe Ala Ile Val Pro Ala Glu Gln
            180                 185                 190

Leu Gly Ile Asp Ile Ser Val Gln Asn Leu Ser Arg Leu Gln Glu Ala
        195                 200                 205

Gly Glu Leu Leu Arg Thr Glu Ile Asn Arg Ser Val Lys Val Gln His
    210                 215                 220

Pro Gln Leu Pro His Ile Asn Thr Val Asp Cys Val Glu Ile Tyr Gly
225                 230                 235                 240

Pro Pro Thr Asn Pro Glu Ala Asn Tyr Lys Asn Val Val Ile Phe Gly
                245                 250                 255

Asn Arg Gln Ala Asp Arg Ser Pro Cys Gly Thr Gly Thr Ser Ala Lys
            260                 265                 270

Met Ala Thr Leu Tyr Ala Lys Gly Gln Leu Arg Ile Gly Glu Thr Phe
        275                 280                 285

Val Tyr Glu Ser Ile Leu Gly Ser Leu Phe Gln Gly Arg Val Leu Gly
    290                 295                 300

Glu Glu Arg Ile Pro Gly Val Lys Val Pro Val Thr Lys Asp Ala Glu
305                 310                 315                 320

Glu Gly Met Leu Val Val Thr Ala Glu Ile Thr Gly Lys Ala Phe Ile
                325                 330                 335

Met Gly Phe Asn Thr Met Leu Phe Asp Pro Thr Asp Pro Phe Lys Asn
            340                 345                 350

Gly Phe Thr Leu Lys
        355

<210> SEQ ID NO 126
<211> LENGTH: 337
<212> TYPE: PRT
<213> ORGANISM: Vibrio parahaemolyticus

<400> SEQUENCE: 126

```
Lys Glu Arg Lys Met Arg Gln Gly Thr Phe Phe Cys Ile Asp Ala His
  1               5                  10                  15

Thr Cys Gly Asn Pro Val Arg Leu Val Ala Gly Gly Val Pro Pro Leu
             20                  25                  30

Glu Gly Asn Thr Met Ser Glu Lys Arg Gln Tyr Phe Leu Glu His Tyr
             35                  40                  45

Asp Trp Ile Arg Gln Ala Leu Met Phe Glu Pro Arg Gly His Ser Met
         50                  55                  60

Met Ser Gly Ser Val Val Leu Pro Pro Cys Ser Asp Asn Ala Asp Ala
 65              70                  75                  80

Ser Ile Leu Phe Ile Glu Thr Ser Gly Cys Leu Pro Met Cys Gly His
                 85                  90                  95

Gly Thr Ile Gly Thr Val Thr Thr Ala Ile Glu Asn Arg Leu Ile Thr
                100                 105                 110

Pro Lys Glu Glu Gly Arg Leu Ile Leu Asp Val Pro Ala Gly Gln Ile
            115                 120                 125

Glu Val His Tyr Gln Thr Lys Gly Asp Lys Val Thr Ser Val Lys Ile
130                 135                 140

Phe Asn Val Pro Ala Tyr Leu Ala His Gln Asp Val Thr Val Glu Ile
145                 150                 155                 160

Glu Gly Leu Gly Glu Ile Thr Val Asp Val Ala Tyr Gly Gly Asn Tyr
                165                 170                 175

Tyr Val Ile Val Asp Pro Gln Glu Asn Tyr Ala Gly Leu Glu His Tyr
                180                 185                 190

Ser Pro Asp Glu Ile Leu Met Leu Ser Pro Lys Val Arg Thr Ala Val
            195                 200                 205

Ser Lys Ala Val Glu Cys Ile His Pro Asn Asp Pro Thr Val Cys Gly
            210                 215                 220

Val Ser His Val Leu Trp Thr Gly Lys Pro Thr Gln Glu Gly Ala Thr
225                 230                 235                 240

Ala Arg Asn Ala Val Phe Tyr Gly Asp Lys Ala Leu Asp Arg Ser Pro
                245                 250                 255

Cys Gly Thr Gly Thr Ser Ala Arg Met Ala Gln Trp His Ala Lys Gly
            260                 265                 270

Lys Leu Lys Ser Gly Glu Asp Phe Val His Glu Ser Ile Ile Gly Ser
            275                 280                 285

Leu Phe Asn Gly Arg Ile Glu Gly Ile Thr Glu Val Asn Gly Gln Thr
            290                 295                 300

Ala Ile Leu Pro Ser Ile Glu Gly Trp Ala Gln Val Tyr Gly His Asn
305                 310                 315                 320

Thr Ile Trp Val Asp Glu Asp Pro Tyr Ala Tyr Gly Phe Glu Val
                325                 330                 335

Lys

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 127

Asp Arg Ser Pro Cys Gly Thr Gly Thr Ser Ala Lys Met Ala
  1               5                  10
```

```
<210> SEQ ID NO 128
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 128

Asn Met Cys Gly His
 1               5

<210> SEQ ID NO 129
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 129

His His His His His His
 1               5
```

What is claimed is:

1. A purified nucleic acid molecule encoding a polypeptide consisting of the amino acid SEQ ID NO:4.

2. A recombinant vector that directs the expression of a nucleic acid molecule encoding a polypeptide consisting of the amino acid sequence SEQ ID NO:4.

3. A isolated host cell transfected or transduced with the recombinant vector of claim 2.

4. A method for the production of a polypeptide consisting of an amino acid sequence SEQ ID NO:4, comprising culturing the host cell of claim 3 under conditions promoting expression, and recovering the polypeptide from the host cell or the culture medium.

5. The method of claim 4, wherein the host cell is selected from the group consisting of bacterial cells, parasite cells, and eukaryotic cells.

6. A kit for detecting a proline racemase encoded by a nucleotide sequence containing a subsequence encoding a peptide selected from SEQ ID NO:4, said kit comprising:
   (a) a polynucleotide primer or probe consisting of the polynucleotide sequence of claim 1; and
   (b) reagents to perform a nucleic acid hybridization reaction.

7. A purified nucleic acid molecule consisting of nucleotides encoding a polypeptide consisting of the amino acid sequence SEQ ID NO:4.

8. A kit for detecting a proline racemase encoded by a nucleotide sequence containing a subsequence encoding the peptide SEQ ID NO:4, said kit comprising:
   (a) a polynucleotide primer or probe consisting of the polynucleotide sequence of claim 7; and
   (b) reagents to perform a nucleic acid hybridization reaction.

* * * * *

UNITED STATES PATENT AND TRADEMARK OFFICE
CERTIFICATE OF CORRECTION

PATENT NO. : 7,556,939 B2  
APPLICATION NO. : 10/545149  
DATED : January 13, 2009  
INVENTOR(S) : Paola Minoprio et al.

It is certified that error appears in the above-identified patent and that said Letters Patent is hereby corrected as shown below:

Title page, item (75) ("Inventors"), line 3, "Paris cedex" should read --Paris Cedex--.

Claim 3, col. 183, line 36, "recombinant vector of claim 2" should read --recombinant vector as claimed in claim 2--.

Claim 6, col. 184, lines 30-31, "encoding a peptide selected from SEQ ID NO: 4" should read --encoding the peptide SEQ ID NO: 4--.

Signed and Sealed this

First Day of September, 2009

David J. Kappos  
*Director of the United States Patent and Trademark Office*